United States Patent
Jeong et al.

(10) Patent No.: US 11,692,160 B2
(45) Date of Patent: Jul. 4, 2023

(54) MICROFLUIDIC CHIP, THREE-DIMENSIONAL CHANNEL STRUCTURE, CELL CULTURE METHOD USING SAME, AND ACTIVITY EVALUATION METHOD OF BIOACTIVE SUBSTANCE USING SAME

(71) Applicants: THE ASAN FOUNDATION, Seoul (KR); UNIVERSITY OF ULSAN FOUNDATION FOR INDUSTRY COOPERATION, Ulsan (KR)

(72) Inventors: Gi Seok Jeong, Seoul (KR); Changmo Hwang, Seoul (KR); Se-Jin Jang, Gyeonggi-do (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 1090 days.

(21) Appl. No.: 16/349,217

(22) PCT Filed: Nov. 10, 2017

(86) PCT No.: PCT/KR2017/012763
§ 371 (c)(1),
(2) Date: May 10, 2019

(87) PCT Pub. No.: WO2018/088856
PCT Pub. Date: May 17, 2018

(65) Prior Publication Data
US 2019/0284517 A1    Sep. 19, 2019

(30) Foreign Application Priority Data
Nov. 10, 2016 (KR) .................. 10-2016-0149798

(51) Int. Cl.
C12M 3/06 (2006.01)
B01L 3/00 (2006.01)
(Continued)

(52) U.S. Cl.
CPC ....... *C12M 23/16* (2013.01); *B01L 3/502761* (2013.01); *C12M 1/26* (2013.01);
(Continued)

(58) Field of Classification Search
CPC ...... C12M 23/16; C12M 23/12; C12M 23/50; C12M 1/26; C12M 1/32; C12M 3/06;
(Continued)

(56) References Cited

U.S. PATENT DOCUMENTS 5,942,443 A * 8/1999 Parce ................ G01N 33/5011
436/514
2002/0106786 A1    8/2002 Carvalho et al.
(Continued)

FOREIGN PATENT DOCUMENTS

EP          2165764       3/2010
KR    10-2007-0033685     3/2007
(Continued)

OTHER PUBLICATIONS

International Searching Authority, International Search Report, issued in connection with International Patent Application No. PCT/KR2017/012763 dated Feb. 19, 2018, 7 pages.
(Continued)

*Primary Examiner* — Michael L Hobbs
(74) *Attorney, Agent, or Firm* — Bridgeway IP Law Group, PLLC; Jihun Kim

(57) ABSTRACT

The microfluidic chip according to an embodiment of the present invention may include a plate, a bridge channel formed in intaglio on one side of the plate, an inlet formed through the plate to communicate with one end of the bridge
(Continued)

channel, an outlet formed through the plate to communicate with the other end of the bridge channel, and at least one well extending in an outward direction of the plate from the bridge channel to provide a space, wherein the bridge channel may be in the form of a curved line, a bent line, an arc, a circle, a spiral, or a polygon.

14 Claims, 52 Drawing Sheets

(51) Int. Cl.
| | | |
|---|---|---|
| *C12M 3/00* | (2006.01) | |
| *C12M 1/32* | (2006.01) | |
| *C12M 1/00* | (2006.01) | |
| *C12M 1/12* | (2006.01) | |
| *C12N 5/00* | (2006.01) | |
| *C12N 5/09* | (2010.01) | |
| *C12Q 1/02* | (2006.01) | |
| *C12M 1/26* | (2006.01) | |

(52) U.S. Cl.
CPC ............... *C12M 1/32* (2013.01); *C12M 3/06* (2013.01); *C12M 21/08* (2013.01); *C12M 23/12* (2013.01); *C12M 23/50* (2013.01); *C12M 25/00* (2013.01); *C12N 5/0062* (2013.01); *C12N 5/0693* (2013.01); *C12Q 1/025* (2013.01); *B01L 2300/0864* (2013.01); *B01L 2300/0874* (2013.01); *C12N 2513/00* (2013.01)

(58) Field of Classification Search
CPC ...... C12M 21/08; C12M 25/00; C12M 33/22; C12N 5/0062; C12N 5/0693; C12N 2501/80; C12N 2501/999; C12Q 1/025; B01L 2200/0605; B01L 2200/0668; B01L 2300/0803; B01L 2300/0809; B01L 2300/0861; B01L 2400/0409; G01N 33/5011; G01N 33/54366
See application file for complete search history.

(56) References Cited

U.S. PATENT DOCUMENTS

| | | | |
|---|---|---|---|
| 2009/0050538 A1* | 2/2009 | Lean | B01D 21/265 209/155 |
| 2014/0141514 A1 | 5/2014 | Yoon et al. | |
| 2015/0284668 A1 | 10/2015 | Hsu et al. | |
| 2016/0038939 A1 | 2/2016 | Min et al. | |

FOREIGN PATENT DOCUMENTS

| | | |
|---|---|---|
| KR | 10-2013-0011101 | 1/2013 |
| KR | 10-2016-0006167 | 1/2016 |
| KR | 10-2016-0008842 | 1/2016 |
| KR | 10-2016-0018200 | 2/2016 |
| WO | 2009146911 | 12/2009 |
| WO | 2013012188 | 1/2013 |
| WO | 2014159356 | 10/2014 |

OTHER PUBLICATIONS

International Searching Authority, "Written Opinion," issued in connection with International Patent Application No. PCT/KR2017/012763 dated Feb. 19, 2018, with English translation, 41 pages.

International Searching Authority, "International Preliminary Report on Patentability," issued in connection with International Patent Application No. PCT/KR2017/012763 dated May 14, 2019, with English translation, 43 pages.

European Patent Office, "Extended European Search Report," issued in connection with European Patent Application No. 17870128.0, dated Jun. 17, 2020, 9 pages.

Korean Intellectual Property Office, "Request for the Submission of an Opinion," issued in connection with Korean Patent Application No. 10-2017-0149888, dated Jan. 24, 2019, with English Translation, 11 pages.

Korean Intellectual Property Office, "Written Decision on Registration," issued in connection with Korean Patent Application No. 10-2017-0149888, dated Aug. 21, 2019, with English Translation, 4 pages.

Korean Intellectual Property Office, "Request for the Submission of an Opinion," issued in connection with Korean Patent Application No. 10-2017-0149887, dated Jan. 24, 2019, with English Translation, 13 pages.

Korean Intellectual Property Office, "Written Decision on Registration," issued in connection with Korean Patent Application No. 10-2017-0149887, dated Aug. 21, 2019, with English Translation, 4 pages.

Korean Intellectual Property Office, "Request for the Submission of an Opinion," issued in connection with Korean Patent Application No. 10-2017-0149886, dated Jan. 22, 2019, with English Translation, 15 pages.

Korean Intellectual Property Office, "Written Decision on Registration," issued in connection with Korean Patent Application No. 10-2017-0149886, dated Jul. 25, 2019, with English Translation, 4 pages.

Korean Intellectual Property Office, "Request for the Submission of an Opinion," issued in connection with Korean Patent Application No. 10-2017-0149889, dated Jan. 31, 2019, with English Translation, 9 pages.

Korean Intellectual Property Office, "Written Decision on Registration," issued in connection with Korean Patent Application No. 10-2017-0149889, dated Aug. 21, 2019, with English Translation, 4 pages.

Temiz et al., "Lab-on-a-chip devices: How to close and plug the lab?," Microelectronic Engineering 132, pp. 156-175,http://dx.doi.org/10.1016/j.mee.2014.10.013, 2015, 20 pages.

\* cited by examiner iii. Centrifuge to trap the cells into the microwell iv. Remove the fibrin in the main channel    suction Collagen

MICROFLUIDIC CHIP, THREE-DIMENSIONAL CHANNEL STRUCTURE, CELL CULTURE METHOD USING SAME, AND ACTIVITY EVALUATION METHOD OF BIOACTIVE SUBSTANCE USING SAME

TECHNICAL FIELD

The present invention relates to a microfluidic chip, a three-dimensional channel structure, a cell culture method using the same, and an activity evaluation method of a bioactive substance using the same.

BACKGROUND ART

Evaluation of a drug that contains an anticancer medicine is carried out by assessing the efficacy and toxicity of the drug for about 10 years. Thereafter, the drug is finally available to the patients. In general, in order to evaluate the efficacy and toxicity of a base drug candidate, a method of culturing cancer cells in a cell culture dish, administering the drug candidate thereto, and measuring the death or gene expression of the cancer cells is used. Once the efficacy and toxicity of a drug have been evaluated at the cellular level as described above, animal testing is carried out. Clinical trials are conducted on the drug that has undergone animal testing. After all of these assessments have been completed, the drug becomes commercially available.

As described above, the evaluation of such a drug generally takes a period of 10 years or more. The process of developing a new drug is also called the valley of death since a huge amount of expenses is required in this process.

Although a drug is confirmed to be effective when administered at the cellular level, it may not be effective when the drug is subjected to animal testing or clinical trials. It has been known that the main reason of the above is attributed to the fact that the system for evaluating a drug by administering it to a two-dimensional culture at the cellular level cannot reflect the environment in which the cells actually operate in a stereoscopic manner, so that the efficacy of the drug cannot be accurately measured. Multicellular tumor spheroids are composed of vascular tissues, fibroblasts, immune cells, and extracellular matrices, together with cancer cells.

These tumor spheroids act organically and secrete various biomaterials including growth factors and grow together with the cancer cells in a complementary manner. If an anticancer medicine is administered to such multicellular tumor spheroids, the cancer cells can be temporarily killed. However, since the method of delivering the drug to the cancer cells utilizes the diffusion of the drug molecule, it is difficult for the administered drug to reach the cancer cells inside the tissues of the multicellular tumor spheroids. In addition, there is a problem that the effect of the drug cannot be maintained as in the initial state because the drug is resistant to the genetic mutation of the cancer cells.

Until recently, the evaluation of a drug at the cellular level did not reflect the interactions between the tissues of multicellular tumor spheroids that surround cancer cells, and the response of the drug to the cancer cells cultured on a two-dimensional plane was measured. Thus, when a drug with a good effect at the cellular level was subjected to animal testing or clinical trials, the results of the former were often different from those of the latter. Due to these problems, the development of a new drug such as an anticancer medicine has required a long period of time and incurred a huge amount of expenses. In addition, unexpected toxicity and side effects stopped the drug development itself.

Thus, in order to solve these problems, thereby evaluating the efficacy of drugs and applying it to the development of a new drug, studies are required to develop a system that simulates the stereoscopic environment in the body.

Meanwhile, an organoid is referred to as an "organ analog" or a "pseudo-organ," which is an organ-specific cell aggregate prepared by aggregating and recombining the cells isolated from stem cells or organ-originated cells by a three-dimensional culturing method. The organoid includes cells of a specific organ to be modeled, reproduces the specific functions of the organ, and is capable of spatial organization in a form similar to that of the actual organ. It has been reported that a patient-derived tumor organoid represents the characteristics of cancer cells and cancer tissues in patients and that it can also reproduce the genetic mutation characteristics of cancer tissues of the patients. Therefore, it is possible to construct a patient-customized drug evaluation system by using the same.

In order to materialize such a system, techniques for co-culturing various cells and efficiently forming an organoid are indispensably required.

DETAILED DESCRIPTION OF THE INVENTION

Technical Problem

An object of the present invention is to provide a microfluidic chip and a three-dimensional channel structure, which include a plurality of wells.

In addition, another object of the present invention is to provide a method for culturing cells and a method for evaluating the activity of a bioactive substance using a microfluidic chip and a three-dimensional channel structure, which comprise a plurality of wells.

Technical Solution to the Problem

The microfluidic chip according to an embodiment of the present invention may include a plate, a bridge channel formed in intaglio on one side of the plate, an inlet formed through the plate to communicate with one end of the bridge channel, an outlet formed through the plate to communicate with the other end of the bridge channel, and one or more wells extending in an outward direction of the plate from the bridge channel to provide a space, wherein the bridge channel may be in the form of a curved line, a bent line, an arc, a circle, a spiral, or a polygon.

In the microfluidic chip according to an embodiment of the present invention, the inlet may include a first passage formed through the plate and a first connection groove that connects the first passage and said one end of the bridge channel.

In the microfluidic chip according to an embodiment of the present invention, the outlet may include a second passage formed through the plate and a second connection groove that connects the second passage and said other end of the bridge channel.

In the microfluidic chip according to an embodiment of the present invention, the inlet and the outlet may be formed in one of an inner region and an outer region of the bridge channel.

In the microfluidic chip according to an embodiment of the present invention, one of an inlet and an outlet may be formed in the inner region of the bridge channel, and the other of the inlet and the outlet may be formed in an outer region of the bridge channel.

In the microfluidic chip according to an embodiment of the present invention, a first part connected to the inlet of the bridge channel and a second part connected to the outlet thereof may be formed in a symmetrical shape.

In the microfluidic chip according to an embodiment of the present invention, the bridge channel may be in the form with a plurality of bends.

In the microfluidic chip according to an embodiment of the present invention, the bridge channel may be in the form of an atypical curve.

In the microfluidic chip according to an embodiment of the present invention, the bridge channel may be in the form of a plurality of arcs, circles, or polygons, which have different sizes from, and are connected to, each other.

In the microfluidic chip according to an embodiment of the present invention, the one or more wells may include a plurality of wells, and the plurality of wells may be spaced apart from each other along the bridge channel.

In the microfluidic chip according to an embodiment of the present invention, the well may include an inclined part formed in a way in which an entrance diameter of the well increases or decreases toward the bridge channel.

In the microfluidic chip according to an embodiment of the present invention, the plate may be formed of glass or a curable polymer.

The microfluidic chip according to an embodiment of the present invention may further include a substrate coupled to one side of the plate.

In the microfluidic chip according to an embodiment of the present invention, the substrate may be a transparent substrate.

In the microfluidic chip according to an embodiment of the present invention, an open part of the bridge channel may be closed by the substrate.

The microfluidic chip according to an embodiment of the present invention may include: a plate; a plurality of bridge channels formed in intaglio on one side of the plate; a plurality of inlets formed by penetrating through the plate, the inlets respectively communicating with one ends of the plurality of bridge channels; a plurality of outlets formed by penetrating through the plate, the outlets respectively communicating with the other ends of the bridge channels; and one or more wells extending in an outward direction of the plate from each of the plurality of bridge channels to provide a space, wherein each of the plurality of bridge channels may be in the form of a curved line, a bent line, an arc, a circle, a spiral, or a polygon.

In the microfluidic chip according to an embodiment of the present invention, the bridge channel may be in the form of a plurality of arcs or circles that have different sizes from each other, and the bridge channel having the smallest diameter among the plurality of bridge channels may be disposed inside and the bridge channel having the largest diameter may be disposed outside.

In the microfluidic chip according to an embodiment of the present invention, the bridge channel may be in the form of a plurality of polygons, which are closed or partially opened and have different dimensions from each other, and the bridge channel having the smallest dimension among the plurality of bridge channels may be disposed inside and the bridge channel having the largest dimension may be disposed outside.

In the microfluidic chip according to an embodiment of the present invention, at least one of the plurality of bridge channels may not be superposed with the other of the plurality of bridge channels.

In the microfluidic chip according to an embodiment of the present invention, at least two of the plurality of bridge channels may be connected to each other.

The microfluidic chip according to an embodiment of the present invention may include a plate, at least one bridge channel formed inside the plate, an inlet formed in the plate to communicate with one end of the bridge channel, an outlet formed in the plate to communicate with the other end of the bridge channel, and at least one well extending in an outward direction of the plate from the bridge channel to provide a space, wherein the bridge channel may be in the form of a curved line, a bent line, an arc, a circle, a spiral, or a polygon.

In the microfluidic chip according to an embodiment of the present invention, the bridge channel may include a plurality of bridge channels, and the plurality of bridge channels may be spaced apart from each other in a vertical direction of the plate.

In the microfluidic chip according to an embodiment of the present invention, the inlet may include a plurality of inlets and the outlet includes a plurality of outlets, the plurality of inlets may be spaced apart from each other to form independent passages, and the plurality of outlets may be spaced apart from each other to form independent passages.

In the microfluidic chip according to an embodiment of the present invention, the plurality of bridge channels may be formed to share the inlet and the outlet.

In the microfluidic chip according to an embodiment of the present invention, the plate may be formed by stacking a plurality of blocks, and at least one bridge channel is formed in each of the plurality of the blocks.

In the microfluidic chip according to an embodiment of the present invention, the inlet may include a first passage formed through the plate and a first connection passage that connects the first passage and said one end of the bridge channel.

In the microfluidic chip according to an embodiment of the present invention, the outlet may include a second passage formed through the plate and a second connection passage that connects the second passage and said the other end of the bridge channel.

In the microfluidic chip according to an embodiment of the present invention, the inlet and the outlet may be formed in one of an inner region and an outer region of the bridge channel.

In the microfluidic chip according to an embodiment of the present invention, any one of the inlet and the outlet may be formed in the inner region of the bridge channel, and the other may be formed in the outer region of the bridge channel.

In the microfluidic chip according to an embodiment of the present invention, the bridge channel may be in the form bent a plurality of times.

In the microfluidic chip according to an embodiment of the present invention, the bridge channel may be in the form of a plurality of circles or polygons, which have different sizes from, and are connected to, each other.

In the microfluidic chip according to an embodiment of the present invention, the bridge channel may be formed in a spiral shape extending in a vertical direction of the plate.

In the microfluidic chip according to an embodiment of the present invention, said at least one well may include a plurality of wells, and the plurality of wells may be spaced apart from each other along the bridge channel.

In the microfluidic chip according to an embodiment of the present invention, the well may be formed in a way in which an entrance diameter of the well increases or decreases toward the bridge channel.

In the microfluidic chip according to an embodiment of the present invention, the plate may be formed of glass or a curable polymer.

In the microfluidic chip according to an embodiment of the present invention, a substrate may be coupled to one surface of the plate.

The three-dimensional channel structure according to an embodiment of the present invention may include a bridge channel having a passage formed therein, at least one well protruding in an outward direction of the bridge channel and being formed along the bridge channel, wherein the inner space thereof communicates with the passage, an inlet channel connected to one end of the bridge channel, and an outlet channel connected to the other end of the bridge channel.

In the three-dimensional channel structure according to an embodiment of the present invention, the bridge channel may be in the form of a curved line, a bent line, an arc, a circle, a spiral, or a polygon.

In the three-dimensional channel structure according to an embodiment of the present invention, the inlet channel may include a first communication part that communicates with one end of the bridge channel and a first extension part that bends at, and extends from, the first communication part, and the outlet channel may include a second communication part that communicates with the other end of the bridge channel and a second extension part that bends at, and extends from, the second communication part.

In the three-dimensional channel structure according to an embodiment of the present invention, the bridge channel may be in the form with a plurality of bends.

In the three-dimensional channel structure according to an embodiment of the present invention, the well may be formed in a way in which an entrance diameter of the well increases or decreases toward the bridge channel.

In the three-dimensional channel structure according to an embodiment of the present invention, the bridge channel, the inlet channel, and the outlet channel may be integrally formed of a curable polymer.

The method for culturing cells according to an embodiment of the present invention may include injecting cells into a microfluidic chip; rotating the microfluidic chip; and culturing the cells in the microfluidic chip, wherein the microfluidic chip may be provided with an inlet, an outlet, a bridge channel connecting the inlet and the outlet, and at least one well formed in an outward direction of the bridge channel, and the cells may be cultured in the well.

The method for culturing cells according to an embodiment of the present invention may further include, after the step of rotating the microfluidic chip, injecting a biomimetic cell support into the microfluidic chip.

In the method for culturing cells according to an embodiment of the present invention, the biomimetic cell support may be at least one selected from the group consisting of collagen, matrigel, fibrin, gelatin, and hyaluronic acid hydrogel.

In the method for culturing cells according to an embodiment of the present invention, the microfluidic chip may include a plate, a bridge channel formed in intaglio on one side of the plate, an inlet formed through the plate to communicate with one end of the bridge channel, an outlet formed through the plate to communicate with the other end of the bridge channel, and at least one well extending in an outward direction of the plate from the bridge channel to provide a space, wherein the bridge channel may be in the form of a curved line, a bent line, an arc, a circle, a spiral, or a polygon.

In the method for culturing cells according to an embodiment of the present invention, the microfluidic chip may include a plate, at least one bridge channel formed inside the plate, an inlet formed in the plate to communicate with one end of the bridge channel, an outlet formed in the plate to communicate with the other end of the bridge channel, and at least one well extending in an outward direction of the plate from the bridge channel to provide a space, wherein the bridge channel may be in the form of a curved line, a bent line, an arc, a circle, a spiral, or a polygon.

The method for evaluating the activity of a physiologically active substance according to an embodiment of the present invention may include injecting cells into a microfluidic chip; rotating the microfluidic chip to supply the cells to a well of the microfluidic chip; injecting a biomimetic cell support into the microfluidic chip; and injecting a physiologically active candidate substance into the microfluidic chip, wherein the microfluidic chip may be provided with an inlet, an outlet, a bridge channel connecting the inlet and the outlet, and at least one well formed in an outward direction of the bridge channel.

In the method for evaluating the activity of a physiologically active substance according to an embodiment of the present invention, the physiologically active candidate substance may include at least one selected from the group consisting of a compound, an anticancer medicine, and a neurotransmitter.

In the method for evaluating the activity of a physiologically active substance according to an embodiment of the present invention, the microfluidic chip may include a plate, a bridge channel formed in intaglio on one side of the plate, an inlet formed through the plate to communicate with one end of the bridge channel, an outlet formed through the plate to communicate with the other end of the bridge channel, and at least one well extending in an outward direction of the plate from the bridge channel to provide a space, wherein the bridge channel may be in the form of a curved line, a bent line, an arc, a circle, a spiral, or a polygon.

In the method for evaluating the activity of a physiologically active substance according to an embodiment of the present invention, the microfluidic chip may include a plate, at least one bridge channel formed inside the plate, an inlet formed in the plate to communicate with one end of the bridge channel, an outlet formed in the plate to communicate with the other end of the bridge channel, and at least one well extending in an outward direction of the plate from the bridge channel to provide a space, wherein the bridge channel may be in the form of a curved line, a bent line, an arc, a circle, a spiral, or a polygon.

The method for preparing an organoid according to an embodiment of the present invention may include injecting cells into a microfluidic chip, rotating the microfluidic chip, and culturing the cells in the microfluidic chip, wherein the microfluidic chip may be provided with an inlet, an outlet, a bridge channel connecting the inlet and the outlet, and at least one well formed in an outward direction of the bridge channel, the cells may be any one selected from tumor cells, organ cells, stem cells, or a combination thereof, and the cells may be cultured in the well.

In the method for preparing an organoid according to an embodiment of the present invention, the tumor cells may be obtained from a cancer patient.

Advantageous Effects of the Invention

The microfluidic chip and the three-dimensional channel structure according to an embodiment of the present invention each include a plurality of wells. If cells are cultured in the wells, it is possible to easily prepare three-dimensional cell spheroids.

In the method for culturing cells according to an embodiment of the present invention, it is possible to culture cell spheroids in a three-dimensional shape.

In the method for evaluating the activity of a physiologically active substance according to an embodiment of the present invention, it is possible to test the pharmacological efficacy of a physiologically active substance.

BRIEF DESCRIPTION OF THE DRAWING

FIG. 16A is a schematic view illustrating the position of the respective cells and the flow direction of collagen and a culture fluid. FIG. 16B shows the result of observing a lung cancer cell line (A549) and fibroblasts with a fluorescence microscope. FIG. 16C shows the result of observing A549, fibroblasts, and vascular cells (HUVECs) with an optical microscope.

FIG. 19B shows the result of observation with an electron microscope after the tumor formation.

FIG. 20A shows the changes in the distribution areas of cancer cells, and FIG. 20B shows the changes in the rates at which the cancer cells reach the vascular structure. FIG. 20C shows the distribution of cancer cells before and after the treatment with gemcitabine as observed with a fluorescence microscope and an optical microscope.

FIG. 21A shows the result of observing the distribution of cells with an optical microscope after treating the cells with the MMP-1 inhibitor in an amount of 10 µM, 50 µM, and 100 µM. The upper figures show the results treated with the MMP-1 inhibitor, and the lower figures show the results treated with DMSO, without treatment with the MMP-1 inhibitor. FIG. 21B is a graph showing the distance traveled from the original location of the lung cancer cells positioned on the bottom after treatment with the MMP-1 inhibitor in various concentrations in FIG. 21A. FIG. 21C is a graph showing the area the lung cancer cells positioned on the bottom have migrated toward the vascular cells after treatment with the MMP-1 inhibitor in various concentrations in FIG. 21A.

FIG. 23 illustrates a culture reservoir for continuously supplying a culture fluid to the microfluidic chip and a flow control system connected to the microfluidic chip.

BEST MODE FOR CARRYING OUT THE INVENTION

Hereinafter, the detailed embodiments of the present invention will be described in detail with reference to the drawings. Here, it is noted that the drawings are not drawn at a specific proportion for convenience of explanation. In addition, in the following description of the present invention, a detailed description of known constitutions or functions related to the present invention will be omitted when it may make the gist of the present invention unclear.

Figure 1:
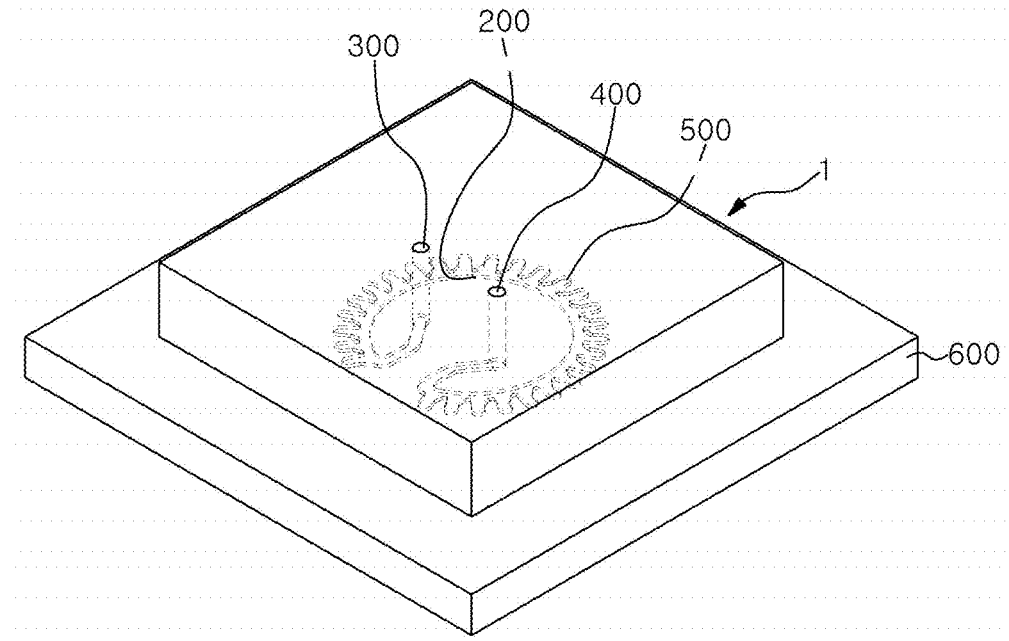
FIG. 1 is a schematic perspective view illustrating a microfluidic chip and a substrate coupled to the microfluidic chip according to an embodiment of the present invention.
Figure 2:
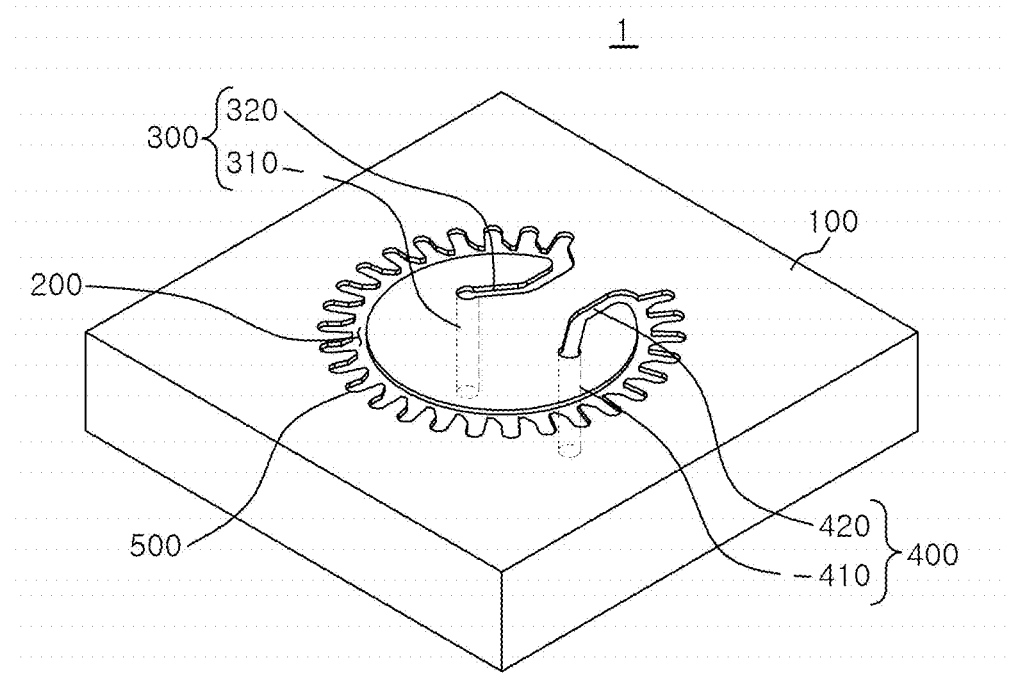
FIG. 2 is a bottom perspective view of the microfluidic chip according to the embodiment of the present invention.
Figure 3:
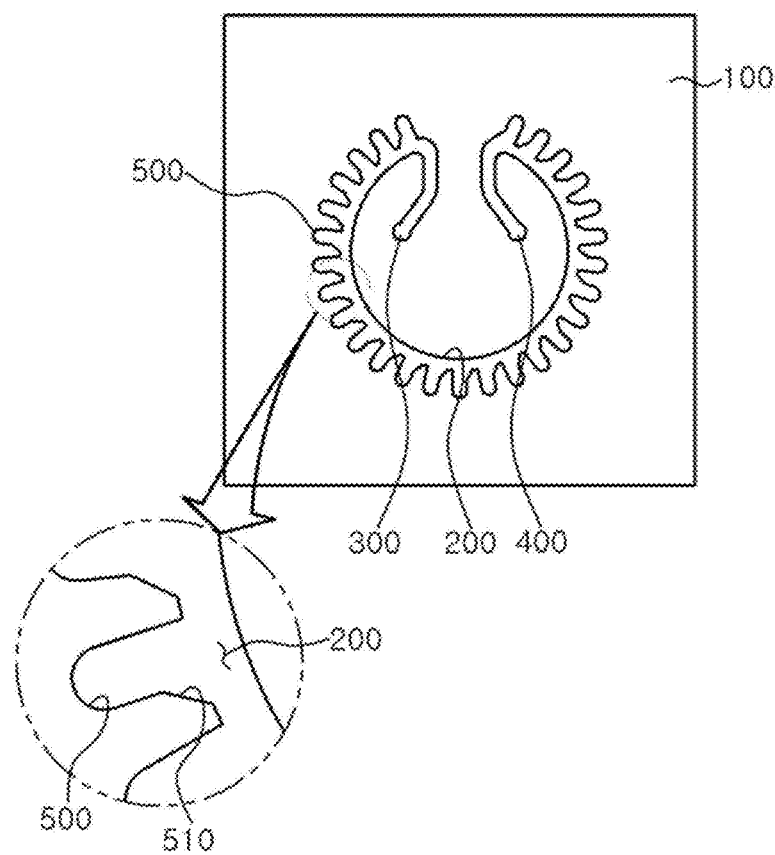
FIG. 3 is a bottom view of the microfluidic chip according to the embodiment of the present invention.

Hereinafter, the constitution of a microfluidic chip according to an embodiment of the present invention will be described with reference to FIGS. 1 to 4L. FIG. 1 is a schematic perspective view illustrating a microfluidic chip and a substrate coupled to the microfluidic chip according to an embodiment of the present invention. FIG. 2 is a bottom perspective view of the microfluidic chip according to the embodiment of the present invention. FIG. 3 is a bottom view of the microfluidic chip according to the embodiment of the present invention. FIGS. 4A to 4K are bottom views illustrating modified examples of the microfluidic chip according to the embodiment of the present invention.

A microfluidic chip 1 according to an embodiment of the present invention may include a plate 100, a bridge channel 200, an inlet 300, an outlet 400, and a well 500.

The plate 100 is a member that forms an outer appearance of the microfluidic chip 1 and may be formed of glass or a curable polymer. For example, the plate 100 may be formed of a silicon component.

A bridge channel 200 may be formed in intaglio on one side of the plate 100. The bridge channel 200 provides a passage through which a fluid that includes cells, a cell culture medium, or the like (hereinafter, collectively referred to as a "fluid") moves. It may be formed in intaglio at a predetermined depth on one side of the plate 100. Thus, when a substrate 600 is coupled to one side of the plate 100, the open part of the bridge channel 200 is closed such that the bridge channel 200 can provide a passage such as a hose or a pipe through which a fluid can move.

The bridge channel 200 may have various shapes. For example, the bridge channel 200 may be in such various forms as a curved line, a bent line, an arc, a circle, a spiral, or a polygon. The shape of the bridge channel 200 will be described later in detail.

The inlet 300 is a part through which a fluid is introduced by a driving member such as a pump. The inlet 300 may be formed through the plate 100, and an end thereof may be connected with the bridge channel 200. In other words, the inlet 300 may be formed through the plate 100 to communicate with one end of the bridge channel 200.

The inlet 300 may include a first passage 310 formed through the plate 100 and a first connection groove 320 that connects the first passage 310 and one end of the bridge channel 200. The first passage 310 is a region that passes through the plate 100. The entrance thereof may be exposed to the other side of the plate 100. The first connection groove 320 may be formed to be indented at a predetermined depth on one side of the plate 100. Here, if the first passage 310 is formed at a position corresponding to one end of the bridge channel 200, the first connection groove 320 may be omitted. In other words, if the first passage 310 is formed to be disposed on one end of the bridge channel 200, the first passage 310 may directly communicate with the bridge channel 200.

An outlet 400 is a part through which a fluid introduced into the bridge channel 200 via the inlet 300 and circulated through the bridge channel 200 and the well 500 is discharged. The outlet 400 may be formed through the plate 100, and an end thereof that passes through the plate 100 may be connected with the bridge channel 200. In other words, the outlet 400 may be formed through the plate 100 to communicate with the other end of the bridge channel 200.

The outlet 400 may include a second passage 410 formed through the plate 100 and a second connection groove 420 that connects the second passage 410 and the other end of the bridge channel 200. The second passage 410 is a region that passes through the plate 100. An entrance of the second passage 410 may be exposed to the other side of the plate 100. The second connection groove 420 may be formed to be indented at a predetermined depth on one side of the plate 100. Here, if the second passage 410 is formed at a position corresponding to the other end of the bridge channel 200, the second connection groove 420 may be omitted. In other words, if the second passage 410 is formed to be disposed on the other end of the bridge channel 200, the second passage 410 may directly communicate with the bridge channel 200.

Meanwhile, the positions of the inlet 300 and the outlet 400 connected to the bridge channel 200 may be variously changed. For example, the inlet 300 and the outlet 400 may be formed in any one of an inner region (S1, see FIG. 4A) and an outer region (S2, see FIG. 4B) of the bridge channel 200. As described above, the inlet 300 and the outlet 400 may be formed in the same region. In addition, the inlet 300 and the outlet 400 may be formed in different regions. In other words, any one of the inlet 300 and the outlet 400 may be formed in the inner region of the bridge channel 200, and the other may be formed in the outer region of the bridge channel 200 (see FIG. 4C). However, the configurations of the inlet 300 and the outlet 400 are not limited to the exemplified configurations. The configurations of the inlet 300 and the outlet 400 may be variously changed as long as the entrance thereof are formed on the other side of the plate 100 and connected to the bridge channel 200 on one side of the plate 100. Here, the part connected to the inlet 300 of the bridge channel 200 and the part connected to the outlet 400 thereof may be formed in a symmetrical shape. In other words, the bridge channel 200 may be formed in a shape symmetrical with respect to the center line (C1) between the inlet 300 and the outlet 400. Such change of the positional arrangement of the inlet 300 and the outlet 400 is not limited to the case where the bridge channel 200 is formed in a circular shape, but it may be applicable to the case where the bridge channel 200 is in the form of a curved line, a bent line, an arc, a spiral, or a polygon.

At least one well 500 may be formed in the bridge channel 200. The well 500 is to provide a space that can be utilized for various purposes such as a cell culture space. It may extend in an outward direction of the plate 100 from the bridge channel 200. As the well 500 extends in an outward direction of the plate 100, when the microfluidic chip 1 according to an embodiment of the present invention is mounted on a centrifugal separator and is rotated, the fluid located in the bridge channel 200 may be introduced into the well 500. The well 500 may be formed in the plural. If the well 500 is formed in the plural, the wells 500 may be formed spaced apart from each other along the bridge channel 200.

In addition, the well 500 may include an inclined part 510 formed in a way in which an entrance diameter D1 of the well 500 is increased or decreased toward the bridge channel 200.

The well 500 may be formed in a cylindrical shape as a whole. The other end of the well 500 that is not connected with the bridge channel 200 may be formed as a curved surface in an outward direction of the plate 100. However, the shape of the well 500 is not limited to the above-described shape. It may be formed in various shapes as long as it is a shape capable of providing a space. Meanwhile, when the well 500 serves as a cell culture space, cells to be cultured may be placed inside the well 500. Here, a fluid containing nutrients necessary for the cell culture may be introduced into the bridge channel 200 through the inlet 300. The fluid may be supplied to at least one well 500 formed to communicate with the bridge channel 200, while it is flowing through the bridge channel 200. The fluid supplied to the well 500 may finally be discharged to the outside via the outlet 400.

A substrate 600 may be coupled to one side of the plate 100. The substrate 600 coupled to one side of the plate 100 closes the open part of the bridge channel 200 such that the bridge channel 200 may serve as a passage for a fluid. As an example, the substrate 600 may be formed of a transparent material such as a slide glass or a cover glass.

Meanwhile, FIGS. 4D to 4K illustrate various configurations of the bridge channel 200 that can be provided to a microfluidic chip according to an embodiment of the present invention. Referring to FIGS. 4D to 4K, variously modified examples of the bridge channel 200 will be described below.

Referring to FIGS. 4D to 4K, the bridge channel 200 is to provide a passage for a fluid. It may be in the form of a curved line, a bent line, an arc, a spiral, or a polygon. In addition, the bridge channel 200 may be formed in the plural on one side of the plate 100.

Figure 4A:
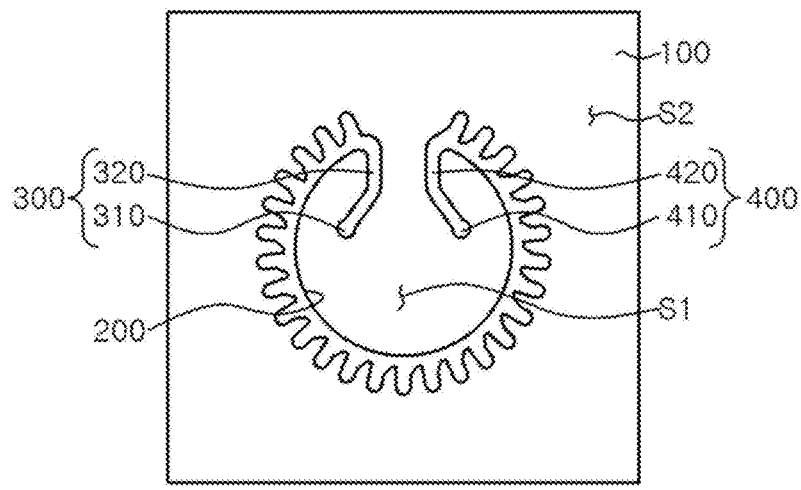
FIG. 4A to 4L are bottom views illustrating modified examples of the microfluidic chip according to the embodiment of the present invention.
Figure 4B:
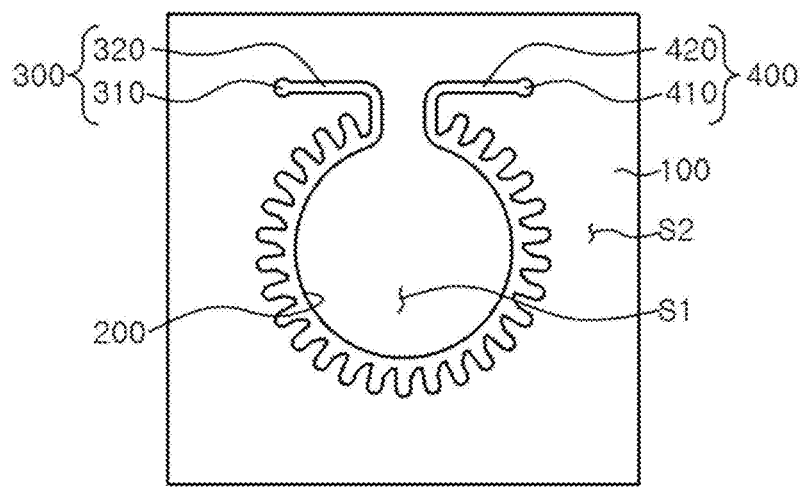
Figure 4C:
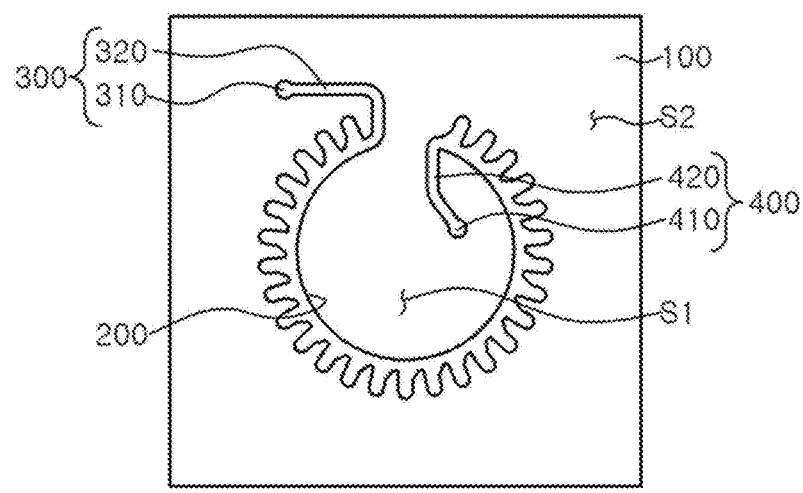
Figure 4D:
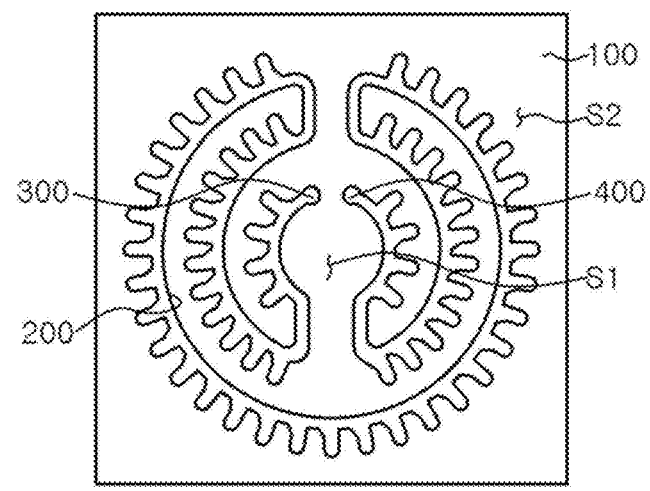
Figure 4E:
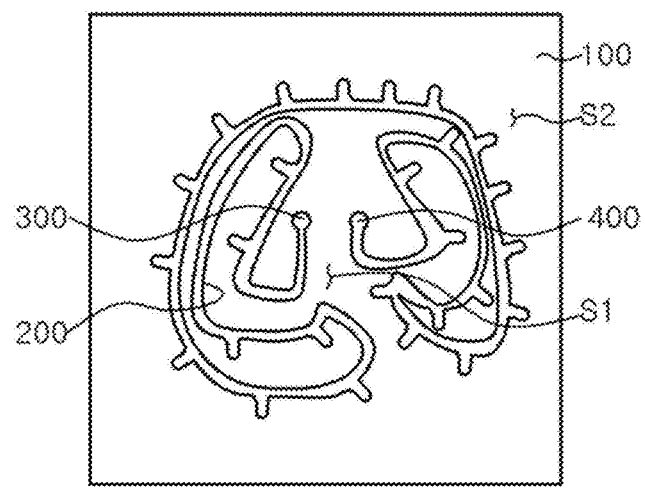
Figure 4F:
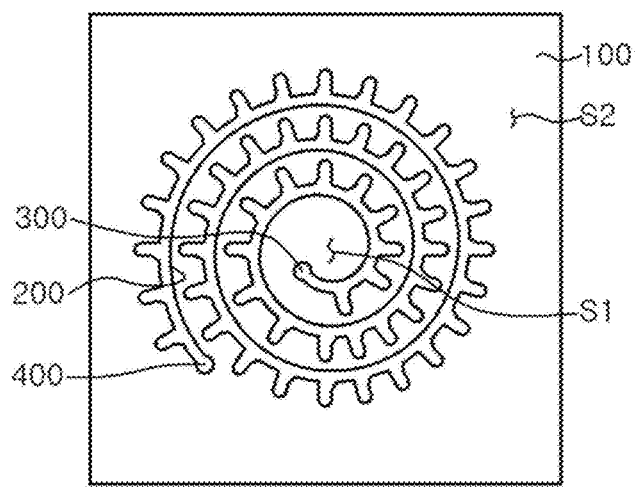
Figure 4G:
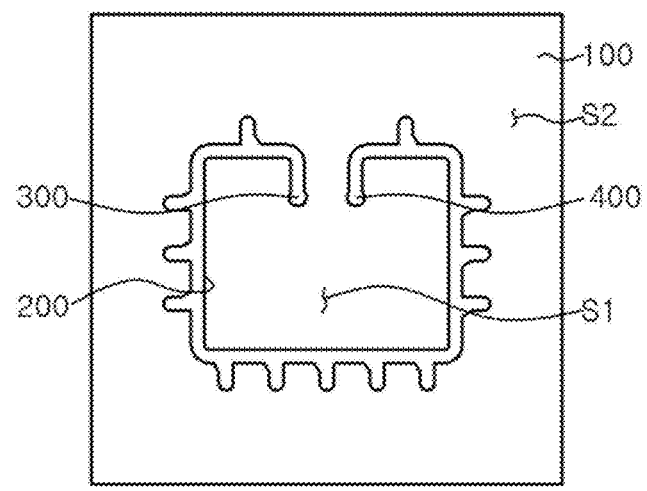
Figure 4H:
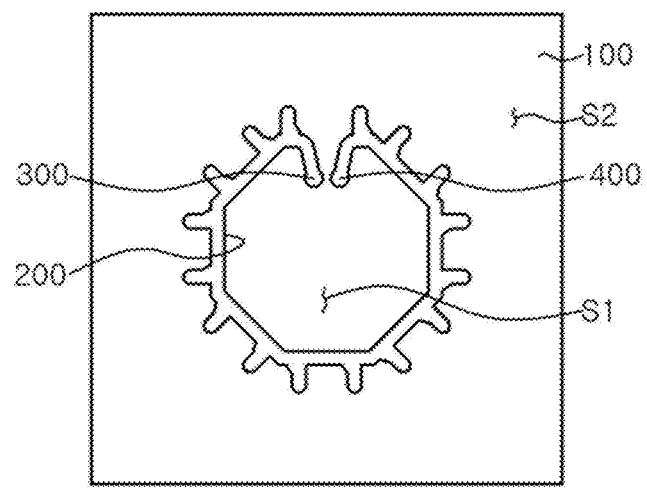
Figure 4I:
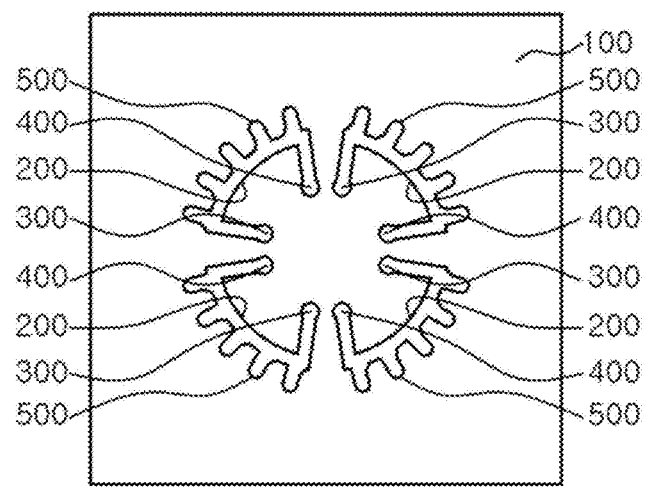
Figure 4J:
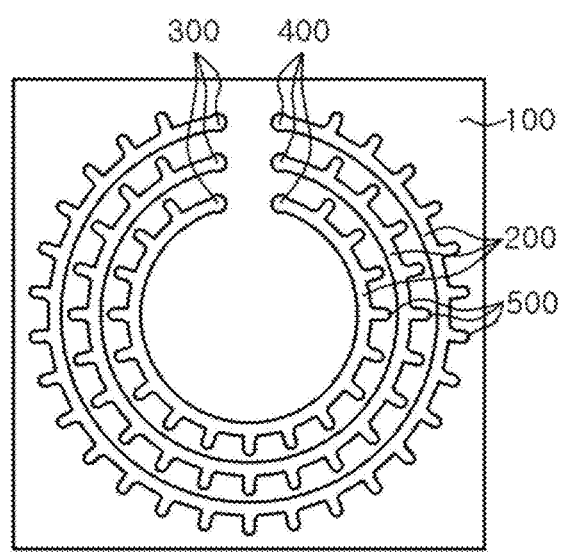
Figure 4K:
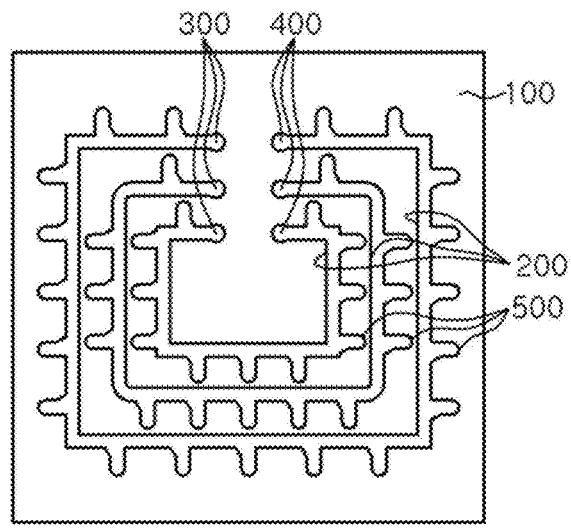
Figure 4L:
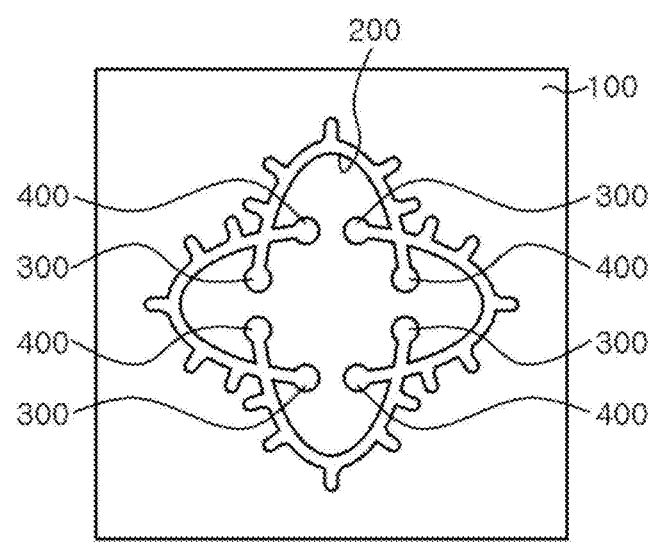

Referring to FIGS. 4D, 4E, and 4F, the bridge channel 200 may be bent in a plurality of times. For example, it may be in the form of a plurality of arcs, circles, or polygons, which have different sizes from, and are connected to, each other. In such event, the bridge channel 200 may be formed as a regular curve (see FIG. 4D) or spiral (see FIG. 4F) with a specific pattern. Alternatively, it may be formed as an irregular curve having no regularity (see FIG. 4E). In addition, referring to FIGS. 4G and 4H, the bridge channel 200 may also be formed as a polygon of various shapes such as a rectangle (see FIG. 4G) and an octagon (FIG. 4H).

Meanwhile, referring to FIGS. 4I to 4L, in the microfluidic chip 1 according to an embodiment of the present invention, the bridge channel 200 may be formed in the plural on one side of the plate 100. In other words, the bridge channel 200 may be formed in the plural in intaglio on one side of the plate 100, each of the inlets 300 may be formed through the plate 100 to communicate with each of one ends of the plurality of bridge channels 200, and each of the outlets 400 may be formed through the plate 100 to communicate with each of the other ends of the bridge channels 200 (see FIG. 4I).

The plurality of bridge channels 200 may be in the form of a plurality of arcs or circles, which have different sizes from each other. In such event, the bridge channel 200 having the smallest diameter among the plurality of bridge channels 200 may be disposed inside, and the bridge channel 200 having the largest diameter may be disposed outside (see FIG. 4J). In addition, the bridge channel 200 may be in the form of a plurality of polygons, which are closed or partially opened and have different widths from each other. In such event, the bridge channel 200 having the smallest width among the plurality of bridge channels 200 may be disposed inside, and the bridge channel 200 having the largest width may be disposed outside (see FIG. 4K). As described above, each of the bridge channels 200 may be independently formed such that at least one of the plurality of bridge channels 200 may not be superposed with another bridge channel 200 (see FIGS. 4I to 4K). Alternatively, the bridge channels 200 may be formed such that at least two of the plurality of bridge channels 200 may be connected to each other (see FIG. 4L). Various configurations of the bridge channel 200 formed in the microfluidic chip 1 according to an embodiment of the present invention have been described above. However, the configuration of the bridge channel 200 is not limited to the embodiments exemplified above. It may be modified in various ways as long as a fluid can move from the bridge channel 200 to the well 500 when the microfluidic chip 1 is mounted on a rotating device, e.g., a centrifugal separator, and is rotated.

Hereinafter, the constitution of a microfluidic chip 1 according to another embodiment of the present invention will be described with reference to FIGS. 5 to 7.

Figure 5:
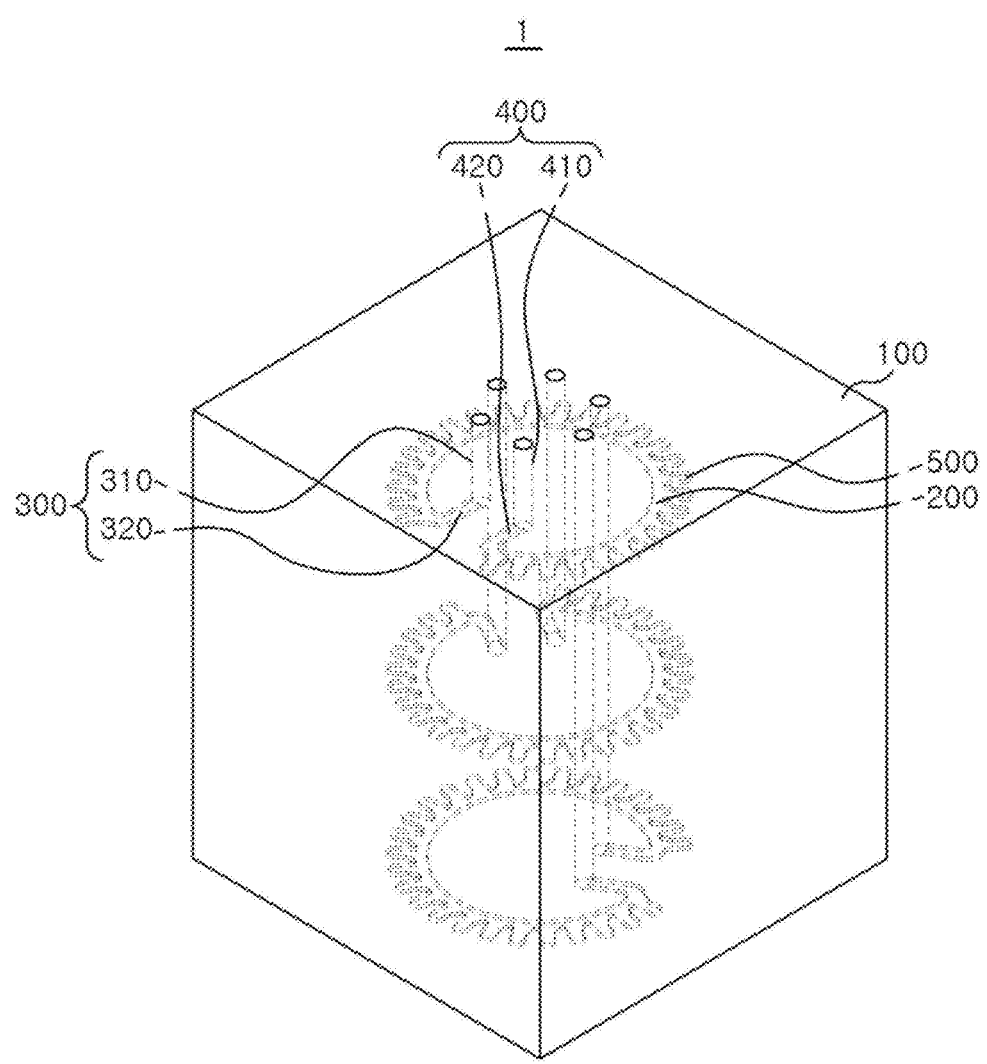
FIG. 5 is a perspective view of a microfluidic chip according to another embodiment of the present invention.
Figure 6:
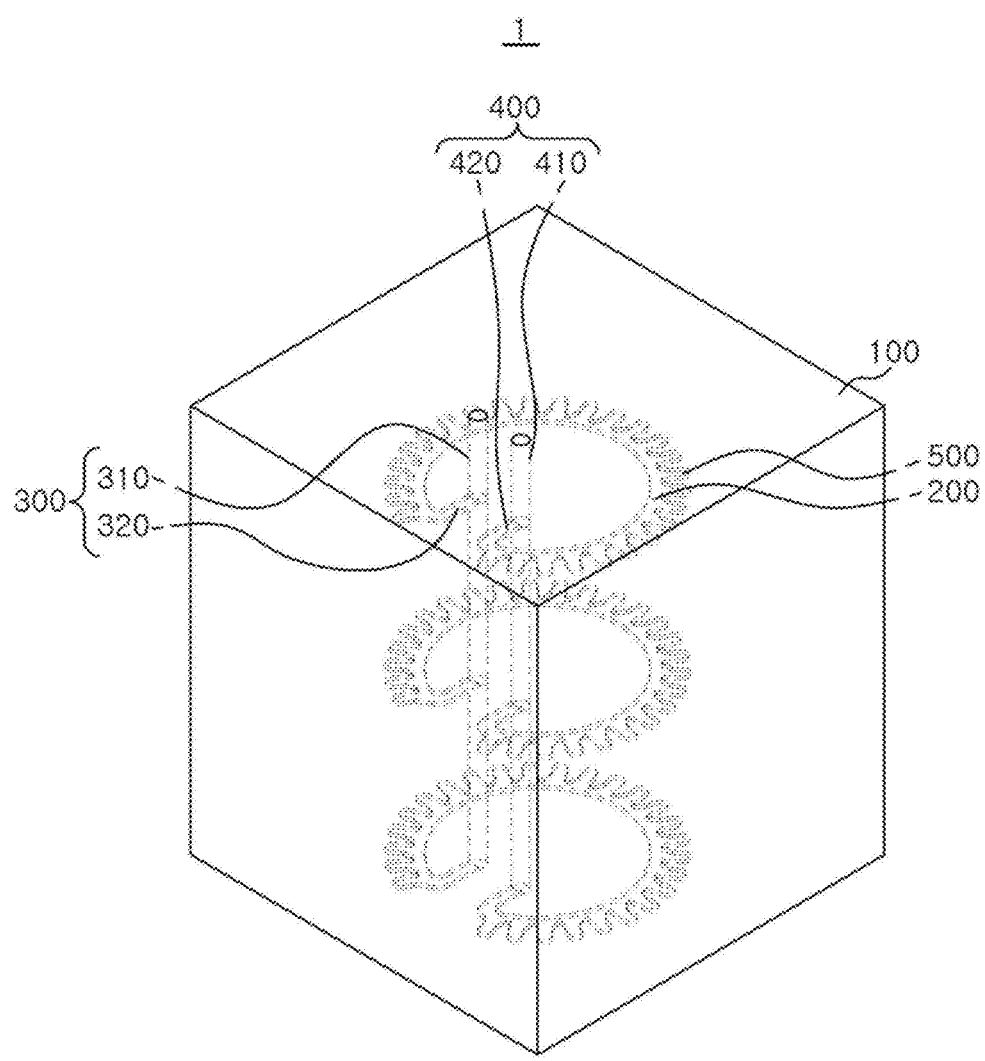
FIG. 6 is a perspective view of a microfluidic chip according to still another embodiment of the present invention.
Figure 7:
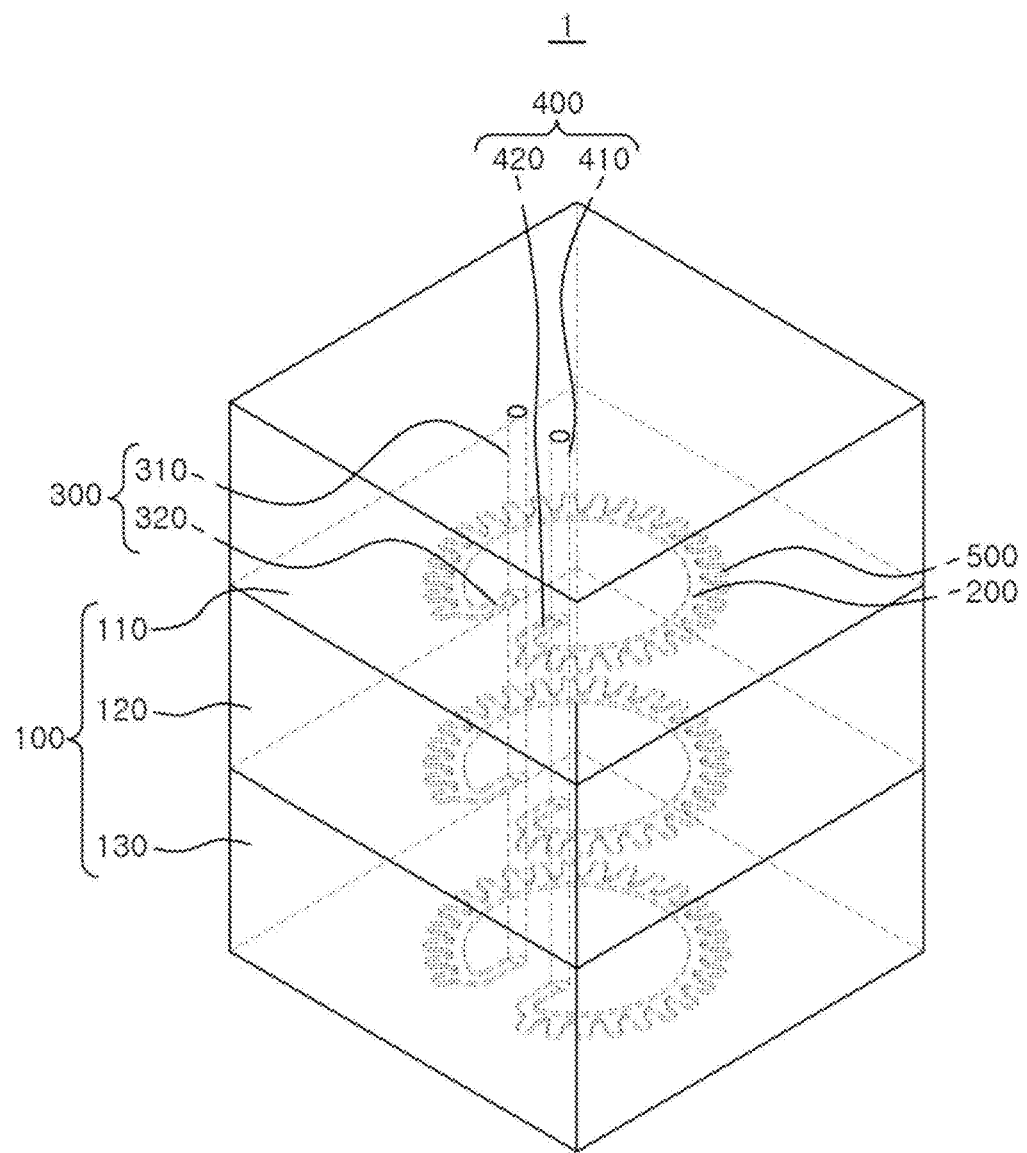
FIG. 7 is a perspective view of a microfluidic chip according to still another embodiment of the present invention.

Referring to FIGS. 5 to 7, the microfluidic chip 1 according to another embodiment of the present invention may include a plate 100, a bridge channel 200 formed inside the plate 100, an inlet 300 formed in the plate 100 to communicate with one end of the bridge channel 200, an outlet 400 formed in the plate 100 to communicate with the other end of the bridge channel 200, and at least one well 500 extending in an outward direction of the plate 100 from the bridge channel 200 to provide a space, wherein the bridge channel 200 may be in the form of a curved line, a bent line, an arc, a circle, a spiral, or a polygon.

Here, the microfluidic chip 1 according to another embodiment of the present invention is the same as the microfluidic chip 1 depicted in FIGS. 1 to 4L in terms of the configuration of the bridge channel 200, the arrangement of the inlet 300, the arrangement of the outlet 400, and the modified examples thereof, except that the bridge channel 200 is formed inside the plate 100. Therefore, a detailed description of the same configuration will be omitted and is referenced to the above description.

Referring to FIGS. 5 to 7, in the microfluidic chip 1 according to another embodiment of the present invention, the bridge channel 200 may be formed inside the plate 100.

Thus, the bridge channel 200 may provide a passage through which a fluid can move although a separate substrate is not coupled to the plate 100. In addition, FIGS. 5 to 7 show only a configuration in which the bridge channel 200 is formed in a circular shape. However, the shape of the bridge channel 200 may be variously changed as a curve, a bent line, an arc, a spiral, or a polygon. In other words, the shape of the bridge channel 200 may be changed in various ways as long as it is a shape capable of providing a passage through which a fluid can move.

One side of the bridge channel 200 may be connected to an inlet 300 through which a fluid may be introduced. The inlet 300 may include a first passage 310 formed through the plate 100 and a first connection passage 320 that connects the first passage 310 and one end of the bridge channel 200.

The other side of the bridge channel 200 may be connected to an outlet 400 through which a fluid may be discharged. The outlet 400 may include a second passage 410 formed through the plate 100 and a second connection passage 420 that connects the second passage 410 and the other end of the bridge channel 200.

Meanwhile, the bridge channel 200 may be formed in the plural. For example, the bridge channel 200 may be formed in the plural, and they may be formed spaced apart from each other in a vertical direction of the plate 100.

If the bridge channel 200 is formed in the plural, the inlet 300 and the outlet 400 may be formed in the plural corresponding with the plurality of bridge channels 200. For example, each of the inlets 300 may be provided to communicate with each of the plurality of bridge channels 200. The inlets 300 may be spaced apart from each other to form independent passages. In addition, each of the outlets 400 may be provided to communicate with each of the plurality of bridge channels 200. The plurality of outlets 400 may be spaced apart from each other to form independent passages (see FIG. 5).

In addition, if the bridge channel 200 is formed in the plural, the inlets 300 and the outlets 400 each may be formed as a single unit. If the inlets 300 and the outlets 400 each are formed as a single unit, the plurality of bridge channels 200 may be formed to share the inlet 300 and the outlet 400 (see FIG. 6).

Meanwhile, the plate 100 may be formed by staking a plurality of blocks 110, 120, and 130 in which a bridge channel 200 is formed. In other words, referring to FIG. 7, the plate 100 may be in a shape in which a plurality of blocks 110, 120, 130 are stacked, and at least one bridge channel 200 may be formed in each of the blocks 110, 120, and 130.

Figure 8:
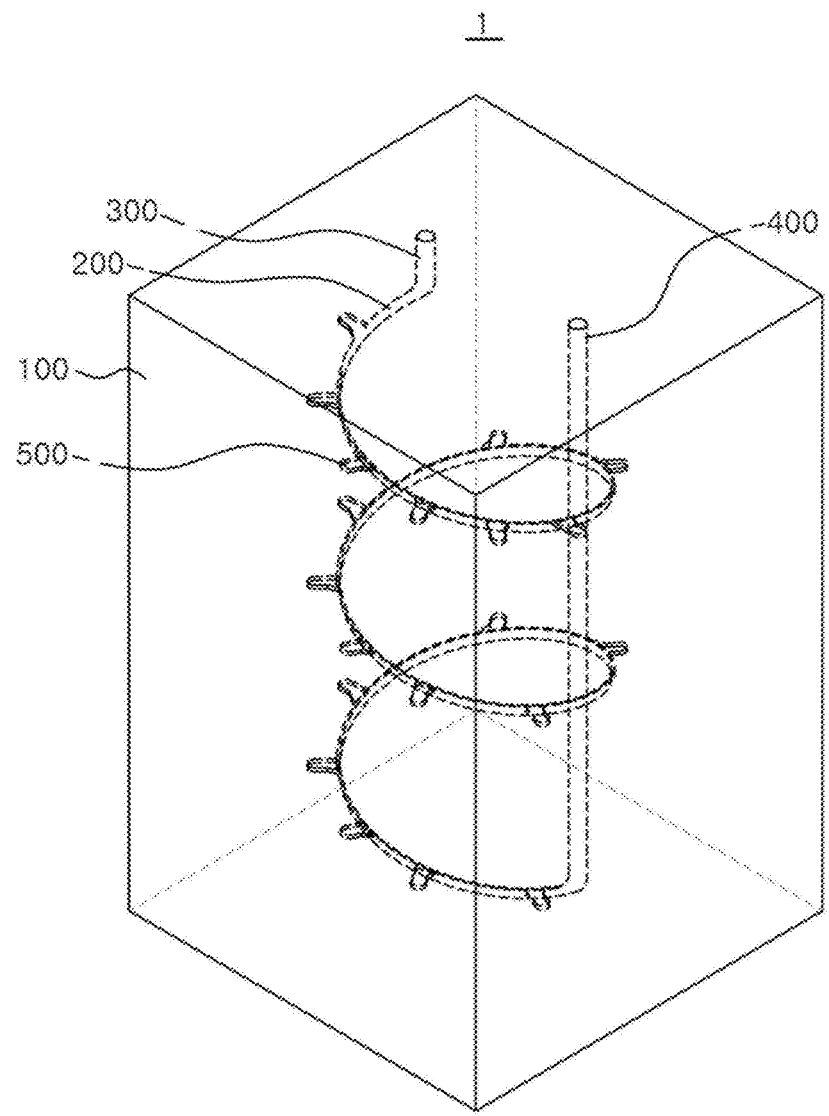
FIG. 8 is a perspective view of a microfluidic chip according to still another embodiment of the present invention.

Hereinafter, the constitution of a microfluidic chip 1 according to still another embodiment of the present invention will be described with reference to FIG. 8. Referring to FIG. 8, the microfluidic chip 1 according to still another embodiment of the present invention may include a plate 100, a bridge channel 200 formed inside the plate 100, an inlet 300 formed in the plate 100 to communicate with one end of the bridge channel 200, an outlet 400 formed in the plate to communicate with the other end of the bridge channel 200, and at least one well 500 extending in an outward direction of the plate 100 from the bridge channel 200 to provide a space, wherein the bridge channel 200 may be formed in a spiral shape extending in the vertical direction of the plate 100.

Here, the bridge channel 200 may be changed in part in various forms of a curved line, a bent line, an arc, or a polygon as long as the bridging channel 200 corresponds to a spiral extending in the vertical direction of the plate 100 as a whole.

Figure 9:
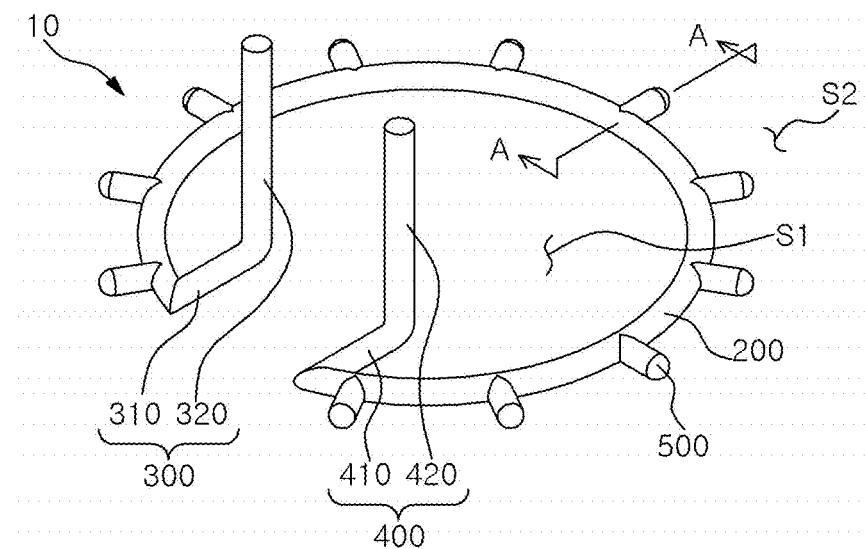
FIG. 9 is a perspective view of a three-dimensional tube structure according to still another embodiment of the present invention.
Figure 10:
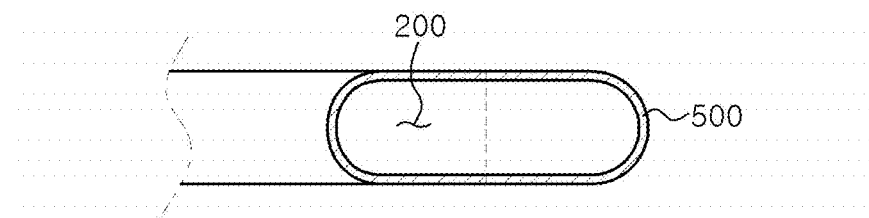
FIG. 10 is a cross-sectional view taken along line A-A shown in FIG. 9.
Figure 11:
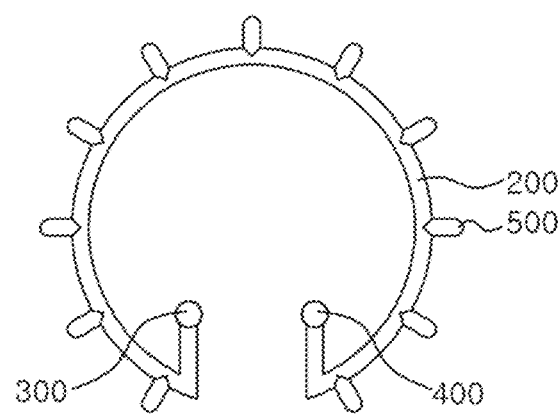
FIG. 11 is a plan view of a three-dimensional tube structure according to still another embodiment of the present invention.

Hereinafter, a three-dimensional tube structure according to still another embodiment of the present invention will be described with reference to FIGS. 9 to 12G. FIG. 9 is a perspective view of a three-dimensional tube structure according to still another embodiment of the present invention. FIG. 10 is a cross-sectional view taken along line A-A. FIG. 11 is a plan view of a three-dimensional tube structure according to still another embodiment of the present invention. FIG. 12 is a plan view illustrating modified examples of a bridge channel of a three-dimensional tube structure according to still another embodiment of the present invention.

Referring to FIGS. 9 to 12, a three-dimensional tube structure 10 according to still another embodiment of the present invention may include a bridge channel 200 having a passage formed therein, at least one well 500 extending in an outward direction of the bridge channel 200 and being formed along the bridge channel, wherein the inner space thereof communicates with the internal passage of the bridge channel 200, an inlet channel 300 connected to one end of the bridge channel 200, and an outlet channel 400 connected to the other end of the bridge channel 200.

In the three-dimensional tube structure 10 according to still another embodiment of the present invention, the internal space of the well 500 provided in the bridge channel 200 is utilized to perform the cell culture, cell tests, and the like. For example, the structure may be fabricated by using a curable polymer such as silicon, or it may be fabricated as an article injection-molded from a resin.

The inlet channel 300 may serve as a passage through which a fluid is introduced. The inlet channel 300 may be provided to communicate with one end of the bridge channel 200. The inlet channel 300 may include a first communication part 310 that communicates with one end of the bridge channel 200 and a first extension part 320 that bends at, and extends from, the first communication part 310. Here, the inlet channel 300 may be disposed in the inner region S1 or the outer region S2 of the bridge channel 200. In other words, the first communication part 310 may be formed so as to extend inward of the bridge channel 200 such that the inlet channel 300 is disposed in the inner region of the bridge channel 200 (see FIG. 9). Alternatively, the first communication part 310 may be formed so as to extend outward of the bridge channel 200 such that the inlet channel 300 is disposed in the outer region of the bridge channel 200 (see FIG. 12A).

The outlet channel 400 may serve as a passage through which a fluid introduced into the bridge channel 200 via the inlet channel 300 and circulated through the bridge channel 200 and the well 500 is discharged. The outlet channel 400 may be provided to communicate with the other end of the bridge channel 200. The outlet channel 400 may include a second communication part 410 that communicates with the other end of the bridge channel 200 and a second extension part 420 that bends at, and extends from, the second communication part 410. Like the inlet channel 300, the outlet channel 400 may be disposed in the inner region S1 or the outer region S2 of the bridge channel 200. In other words, the second communication part 410 may be formed so as to extend inward of the bridge channel 200 such that the outlet channel 400 is disposed in the inner region of the bridge channel 200. Alternatively, the second communication part 410 may be formed so as to extend outward of the bridge channel 200 such that the outlet channel 400 is disposed in the outer region of the bridge channel 200.

Figure 12A:
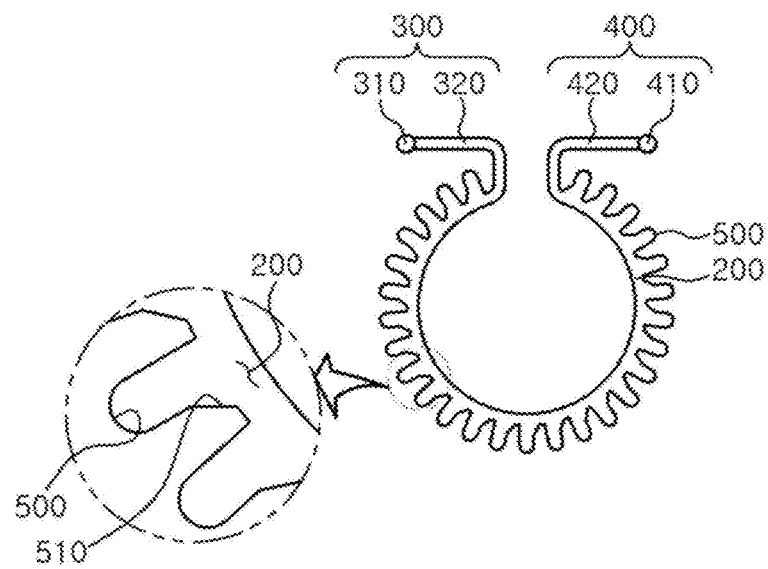
FIGS. 12A to 12G are plan views illustrating modified examples of a bridge channel of a three-dimensional tube structure according to the still another embodiment of the present invention.
Figure 12B:
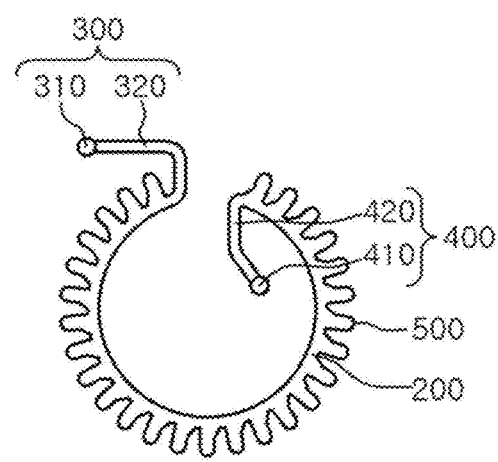
Figure 12C:
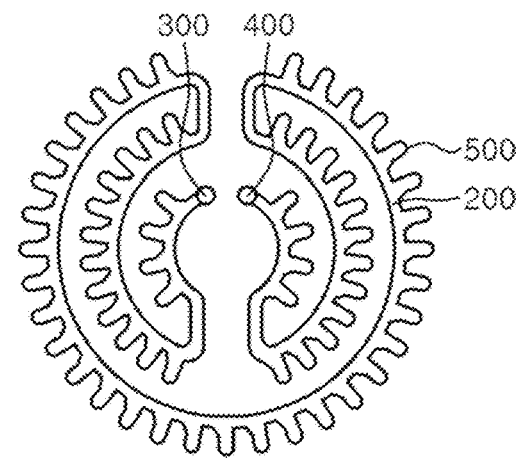
Figure 12D:
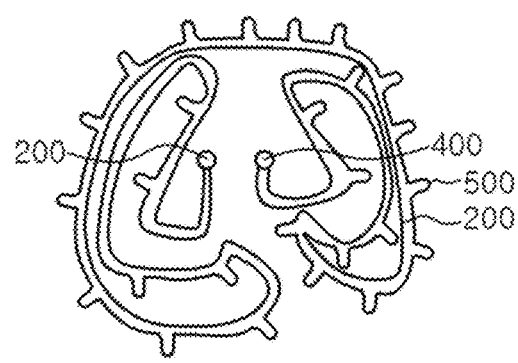
Figure 12E:
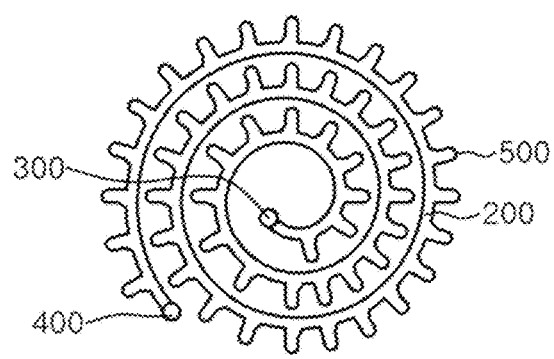
Figure 12F:
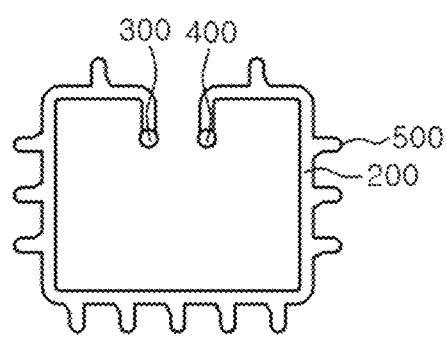
Figure 12G:
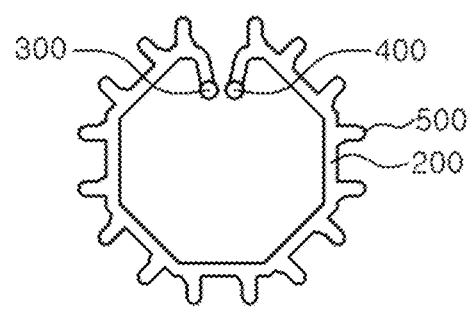

In addition, it is possible that any one of the inlet channel 300 and the outlet channel 400 is disposed in the inner region of the bridge channel 200, and the other is disposed in the outer region of the bridge channel 200 (see FIG. 12B).

The bridge channel 200 may have various shapes. For example, the bridge channel 200 may be in such various forms as a curved line, a bent line, an arc, a circle, a spiral, or a polygon. Here, the configuration of the modified examples of the bridge channel 200 according to still another embodiment of the present invention is the same as the configuration of the bridge channel 200 depicted in FIGS. 4A to 4I, except that the bridge channel 200 is formed in relievo. Therefore, a detailed description of the configuration will be omitted and is referenced to the above description.

At least one well 500 may be formed in the bridge channel 200. The well 500 is to provide a space that can be utilized for various purposes such as a cell culture space. It may extend in an outward direction from the bridge channel 200. As the well 500 extends in an outward direction, when the three-dimensional tube structure 10 according to an embodiment of the present invention is mounted on a centrifugal separator and is rotated, the fluid located in the bridge channel 200 may be introduced into the well 500. The well 500 may be formed in the plural. If the well 500 is formed in the plural, the wells 500 may be formed spaced apart from each other along the bridge channel 200.

In addition, the well 500 may include an inclined part 510 formed in a way in which the entrance diameter of the well 500 is increased or decreased toward the bridge channel 200. In other words, one end of the well 500 on the side of the bridge channel 200 may be formed into a funnel shape.

Hereinafter, the method for culturing cells and the method for evaluating the activity of a physiologically active substance using the microfluidic chip and the three-dimensional channel structure will be described.

Cells may be supplied to wells of the microfluidic chip and the three-dimensional channel structure. The cells may be supplied in a mixed state with a three-dimensional biomimetic cell support. But they are not limited thereto.

The "well" may be in the form of a curved surface. The depth thereof may be 20 to 20,000 µm, 100 to 10,000 µm, or 200 to 2,000 µm, and the average diameter thereof may be 10 to 10,000 µm, 50 to 5,000 µm, or 100 to 1,000 µm. But they are not limited thereto.

In addition, the well may be filled with a three-dimensional biomimetic cell support. The well may be in the plural, which depends on the outer diameter of the microfluidic chip. The size of the microfluidic chip may be 1 mm to 1,000 mm, preferably 10 mm to 100 mm.

The "three-dimensional biomimetic cell support" simulates the cell culture environment in the body and may include an extracellular matrix (ECM). The cell support is commonly used for culturing cancer cells in a three-dimensional environment similar to a living body. The cell support makes it possible to culture cancer cells in the most similar manner to a living body. Thus, if cells are cultured in the three-dimensional biomimetic cell support, they can be cultured in an environment similar to that in the body in terms of the intercellular interactions and metabolism activities. The three-dimensional biomimetic cell support may include at least one selected from the group consisting of collagen, matrigel, fibrin, gelatin, and hyaluronic acid hydrogel. The three-dimensional biomimetic cell support may be supplied to the microfluidic chip either in a mixed state with cells or alone.

Cells that may be additionally supplied to the microfluidic chip are cells to be cultured in the microfluidic chip, which are derived from mammals including primates, rodents, and the like. As an example, the cells may be human cells. For example, they may be at least one selected from the group consisting of normal cells and cancer cells of a human. The normal cells may refer to cells derived from various tissues that are not cancer cells. The normal cells or cancer cells may be stem cells or non-stem cells (cells without stemness). For example, the stem cells may be normal tissues, for example, stem cells (i.e., organ stem cells) of normal organs (e.g., stomach, small intestine, large intestine, heart, liver, kidney, lung, spleen, or the like), adult stem cells, or cancer stem cells. In addition, the normal cells or cancer cells may be derived from a patient. The cells may be mixed with a three-dimensional biomimetic cell support and then supplied.

The "adult stem cells" are stem cells extracted from umbilical cord blood or adult bone marrow, blood, nerves, or the like. The adult stem cells refer to primitive cells just before being differentiated into cells of a specific organ. The adult stem cells may be at least one selected from the group consisting of hematopoietic stem cells, mesenchymal stem cells, and neural stem cells. The adult stem cells may be adult stem cells of a mammal such as a human. Adult stem cells are difficult to proliferate and tend to be easily differentiated. In contrast, it is possible to reproduce various organs that are actually needed in medicine using various types of adult stem cells. In addition, since adult stem cells are characterized in that they can be differentiated according to the characteristics of each organ after transplantation, they may be advantageously applied to the treatment of intractable diseases/incurable diseases.

As an example, the "cancer cells" may refer to various kinds of cancer cells including those derived from a pancreatic cancer cell line (Mia Paca-2) or a lung cancer cell line (A549). The "patient-derived cells" may refer to cells collected from a patient suffering from a particular disease, such as a patient suffering from pancreatic cancer or lung cancer. The "patient-derived cancer cells" may refer to cancer cells collected from a patient suffering from a particular disease, such as pancreatic cancer and lung cancer.

In another embodiment, the microfluidic chip may further include a bridge channel connected to the entrance of the well. The connection between the entrance of the well and the bridge channel may be straight or curved. In addition, the width of the bridge channel connected to the entrance of the well may be 10 to 10,000 µm, 50 to 5,000 µm, or 100 to 5,000 µm, preferably 100 to 1,000 µm.

The bridge channel may further include a fluid including a cell culture medium. The cell culture medium may include a drug and particles that a drug is coated on or contained in. The drug may include an anticancer drug and an antiviral drug such as Gemcitabine (4-amino-1-(2-deoxy-2,2-difluoro-β-D-erythro-pentofuranosyl)pyrimidin-2(1H)-on), Paclitaxel (2α,4α,5β,7β,10β,13α)-4,10-Bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate), or an MMP-1 inhibitor.

The "fluid" is a material with a flowing nature and can be mixed with cells and then injected through the bridge channel connected to the entrance of the well. The fluid may be at least one selected from the group consisting of a cell culture medium and physiological saline. The fluid may further include at least one selected from the group consisting of vascular cells, fibroblasts, immune cells, cancer stem cells, cancer cells, organ stem cells (e.g., stem cells of stomach, small intestine, large intestine, heart, liver, kidney, lung, spleen, or the like), adult stem cells, and normal tissue cells (e.g., non-stem cells or stem cells of tissues other than blood vessels).

The "cancer stem cells (CSCs)" refer to cells having the ability to produce a tumor among cancer cells. They are also called tumor-initiating cells (TICs) because they have a tumorigenic ability, unlike tumor cells that do not form a tumor.

As an example, the "cancer cells" may refer to various kinds of cancer cells including those derived from a pancreatic cancer cell line (Mia Paca-2) or a lung cancer cell line (A549). The "patient-derived cells" may refer to cells collected from a patient suffering from a particular disease, such as a patient suffering from pancreatic cancer or lung cancer. The patient-derived cells may refer to cancer cells collected from a patient suffering from a particular disease, such as pancreatic cancer and lung cancer.

As described above, the "organ stem cells" may refer to stem cells of heart, lung, spleen, liver, kidney, and stomach and intestines (stomach, small intestine, large intestine).

The "tissue cells" refer to cells that constitute a tissue, such as an epithelial tissue, a supporting tissue, a muscle tissue, and a nervous tissue, which is an organism having functional and structural merits formed by cells having the same direction of differentiation. The tissue cells may refer to only a single type of cells or a variety of cell types that form a specific tissue.

The microfluidic chip may further include an inlet through which a fluid may be continuously supplied. A pump for supplying a fluid may be connected to the inlet. The inlet is a part to which a fluid is supplied. A pump is connected thereto to supply a fluid to the microfluidic chip.

In another embodiment, the microfluidic chip may include a bridge channel to which a well is connected; and a fluid that includes a physiologically active substance, cells, or a combination thereof, wherein the fluid may be supplied to the bridge channel, and the microfluidic chip may be used for evaluating the activity of the physiologically active substance on cells.

The "physiologically active substance" is a substance that regulates the gene expression and physiological functions of a living organism. It may refer to a substance that enhances or inhibits the function of the living body. The physiologically active substance may include at least one selected from the group consisting of a compound, an anticancer medicine, and a neurotransmitter. But it is not limited thereto.

The "cells" that may be additionally included in the microfluidic chip for evaluating the activity of a physiologically active substance on cells are those to be cultured in the microfluidic chip for evaluating the activity of a physiologically active substance on cells. The cells may be derived from mammals including primates, rodents, and the like. As an example, the cells may be human cells. For example, they may be at least one selected from the group consisting of human normal cells and cancer cells. The normal cells may refer to cells derived from various tissues that are not cancer cells. The normal cells or cancer cells may be stem cells or non-stem cells (cells without stemness). The stem cells may be normal tissues, for example, stem cells (i.e., organ stem cells) of normal organs (e.g., stomach, small intestine, large intestine, heart, liver, kidney, lung, spleen, or the like), adult stem cells, or cancer stem cells. In addition, the normal cells or cancer cells may be derived from a patient. The cells may be supplied through the well in a mixed state with a three-dimensional biomimetic cell support. They may be supplied through the bridge channel connected to the entrance of the well.

In another embodiment, the present invention provides a method for culturing cells, which includes 1-1) supplying a mixture of cells and a three-dimensional biomimetic cell support into a well in a microfluidic chip; 2-1) mounting the microfluidic chip on a rotating device; and 3) rotating the rotating device, or 1-2) mounting a microfluidic chip on a rotating device; 2-2) supplying a mixture of cells and a three-dimensional biomimetic cell support into a well in the microfluidic chip; and 3) rotating the rotating device.

The well may be in the plural, which may be positioned symmetrically, concentrically, or spirally about the axis of rotation.

The "rotating device" refers to one that rotates by centrifugal force about the rotating shaft. For example, it may be a centrifugal separator. In addition, the microfluidic chip mounted on the rotating device is applied by centrifugal force. The rotational speed of the rotating device is 500 to 6,000 rpm such that the cells injected into the well are not damaged. The cells injected into the microfluidic chip can be placed in the well by centrifugal force.

The microfluidic chip can be "mounted" on the rotating device. This may mean that the microfluidic chip is connected to the rotating device via a connecting device, that the microfluidic chip is attached to the rotating device through a mounting device, or the microfluidic chip is inserted to the inside of the rotating device. But it is not limited thereto.

The step of rotating the rotating device may be carried out for 3 to 60 seconds. But it is not limited thereto.

The "three-dimensional biomimetic cell support" simulates the cell culture environment in the body and may include an extracellular matrix (ECM). It is commonly used to culture cancer cells in a three-dimensional environment similar to a living body. It makes it possible to culture cancer cells in the most similar manner to a living body since several types of cells can be injected thereto. Thus, if cells are cultured in a three-dimensional biomimetic cell support, they can be cultured in an environment similar to that in the body in terms of the intercellular interactions and metabolism activities. The biomimetic cell support may include at least one selected from the group consisting of collagen, matrigel, fibrin, gelatin, and hyaluronic acid hydrogel. It may be supplied to the well either in a mixed state with cells or alone.

The "cells" that may be cultured by the method for culturing cells are cells to be cultured in the microfluidic chip, which may be derived from mammals including primates, rodents, and the like. As an example, the cells may be human cells. For example, they may be at least one selected from the group consisting of human normal cells and cancer cells. The normal cells may refer to cells derived from various tissues that are not cancer cells. The normal cells or cancer cells may be stem cells or non-stem cells (cells without stemness). For example, the stem cells may be normal tissues, for example, stem cells (i.e., organ stem cells) of normal organs (e.g., stomach, small intestine, large intestine, heart, liver, kidney, lung, spleen, or the like), adult stem cells, or cancer stem cells. In addition, the normal cells or cancer cells may be derived from a patient. The cells may be supplied through the well in a mixed state with a three-dimensional biomimetic cell support. They may be supplied through the bridge channel connected to the entrance of the well.

In the method for culturing cells, the well may further include a bridge channel connected to the entrance of the well. The step of supplying the mixture of the cells and the three-dimensional biomimetic cell support to the well of the microfluidic chip may be carried out through the bridge channel connected to the entrance of the well. The connection between the entrance of the well and the bridge channel may be straight or curved. In addition, the width of the bridge channel connected to the entrance of the well may be 100 to 5,000 μm. The bridge channel may further include a fluid including a cell culture medium. The cell culture medium may include a drug and particles that a drug is coated on or contained in. The drug may include an anticancer drug and an antiviral drug such as Gemcitabine (4-amino-1-(2-deoxy-2,2-difluoro-β-D-erythro-pentofuranosyl)pyrimidin-2(1H)-on), Paclitaxel (2α,4α,5β,7β,10β,13α)-4,10-Bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate), or an MMP-1 inhibitor.

The method for culturing cells may further include supplying a fluid including a cell culture medium through the bridge channel. The fluid may be at least one selected from the group consisting of a cell culture medium and physiological saline. But it is not limited thereto. In addition, the fluid may further include at least one selected from the group consisting of vascular cells, fibroblasts, immune cells, cancer stem cells, cancer cells, organ stem cells, adult stem cells, and normal tissue cells. The fluid and the physiologically active substance may be mixed and injected into the bridge channel connected to the entrance of the well.

In the step of supplying a fluid including a cell culture medium through the bridge channel, the step of supplying the fluid may take place for a certain period of time, persistently, intermittently, or continuously.

In the method for culturing cells, an inlet through which a fluid is continuously supplied may be further included. A pump for supplying a fluid may be connected to the inlet. The inlet is a part through which a fluid is supplied. A pump is connected thereto to supply a fluid to the microfluidic chip for a certain period of time, persistently, or continuously.

The method for culturing cells may further include culturing the cells obtained in the step 3 of rotating the rotating device.

In another embodiment, the present invention provides a method for evaluating the activity of a physiologically active substance, which includes 1-1) supplying a mixture of cells and a three-dimensional biomimetic cell support into a well in a microfluidic chip; 2-1) mounting the microfluidic chip on a rotating device; 3) rotating the rotating device; and 4) adding the physiologically active substance to a reaction product obtained in step 3; or 1-2) mounting a microfluidic chip on a rotating device; 2-2) supplying a mixture of cells and a three-dimensional biomimetic cell support into a well in the microfluidic chip; 3) rotating the rotating device; and 4) adding the physiologically active substance to a reaction product obtained in step 3.

The "physiologically active substance" in the method for evaluating the activity of a physiologically active substance is a substance that regulates the gene expression and physiological functions of a living organism. It may refer to a substance that enhances or inhibits the function of the living body. It may include a compound, an anticancer medicine, and a neurotransmitter. But it is not limited thereto. For example, the physiologically active substance may include an anticancer drug and an antiviral drug such as Gemcitabine (4-amino-1-(2-deoxy-2,2-difluoro-β-D-erythro-pentofuranosyl)pyrimidin-2(1H)-on), Paclitaxel (2α,4α, 5β,7β, 10β,13 α)-4,10-Bis(acetyloxy)-13-{[(2R,3 S)-3-(benzoylamino)-2-hydroxy-3-phenylpropanoyl] oxy}-1,7-dihydroxy-9-oxo-5,20-epoxytax-11-en-2-yl benzoate), or an MMP-1 inhibitor.

In the method for evaluating the activity of a physiologically active substance, the well may further include a bridge channel connected to the entrance of the well. The step of supplying the cells into the well in the microfluidic chip or the step of adding the physiologically active substance may be carried out through the bridge channel connected to the entrance of the well. But it is not limited thereto.

In the method for evaluating the activity of a physiologically active substance, the step of supplying the mixture of cells and a three-dimensional biomimetic cell support into the well in the microfluidic chip or the step of adding the physiologically active substance may be carried out through the bridge channel connected to the entrance of the well. The step of supplying the mixture of cells and a three-dimensional biomimetic cell support into the well or the step of adding the physiologically active substance may further include supplying a fluid including a cell culture medium through the bridge channel.

The step of supplying a fluid including a cell culture medium through the bridge channel may take place for a certain period of time, persistently, intermittently, or continuously.

The fluid may be selected from the group consisting of a cell culture medium and physiological saline. The fluid may further include at least one selected from the group consisting of vascular cells, fibroblasts, immune cells, cancer stem cells, cancer cells, organ stem cells, adult stem cells, and normal tissue cells.

In addition, the fluid may further include the physiologically active substance. The fluid including the physiologically active substance may be supplied through the well, preferably through the bridge channel connected to the entrance of the well.

In the method for evaluating the activity of a physiologically active substance, the step of supplying a fluid including a cell culture medium through the bridge channel may be carried out simultaneously with at least one step of the method for evaluating the activity of a physiologically active substance, carried out between any steps thereof, or carried out continuously through the entire steps thereof. But it is not limited thereto.

In another embodiment, multicellular tumor spheroids, which have an average diameter of 100 to 1,000 μm and include an extracellular matrix secreted from cells, may be cultured by the method for culturing cells.

The "extracellular matrix (ECM)" is a complex aggregate of biomolecules that fill the tissue or extracellular space. It is composed of molecules that are synthesized by cells and secreted and accumulated outside the cells. The extracellular matrix may include at least one selected from the group consisting of collagen, matrigel, fibrin, gelatin, and hyaluronic acid hydrogel.

The "multicellular tumor spheroids" may refer to cells to be cultured, endothelial cells (ECs), an extracellular matrix, and the like. They may further include at least one selected from the group consisting of vascular cells, fibroblasts, immune cells, cancer stem cells, cancer cells, organ stem cells, adult stem cells, and normal tissue cells.

The cells that constitute multicellular tumor spheroids may be various kinds of cancer cells including pancreatic cancer cells and lung cancer cells. The multicellular tumor spheroids may have a cancer stem cell function.

The term "organoid" as used herein collectively refer to a small artificial organ or a unit organ similar to the function and structure of a human organ. In addition, techniques for forming it by using stem cell differentiation methods and techniques for forming it by using in vitro culture methods using organ cells are also known. In addition, an organoid may be referred to as an in vitro patient, an in vitro human, or an in vitro laboratory animal due to its biomimetic features. However, scientists who specialize in stem cells recognize only those formed through stem cell differentiation as an organoid. Those formed using in vitro culture methods using organ cells are referred to as an organ spheroid. The organoid a small artificial organ formed similarly to that in the body. The organoid enables the evaluation process, which incurs a huge amount of expenses in the drug development process up to the present, to be performed precisely before the clinical trials. Thus, it is one of the newest drug development approaches that is trusted to improve the accuracy of drug development and reduce costs significantly.

Meanwhile, the microfluidic chip or the three-dimensional tube structure according to an embodiment of the present invention as described above may be fabricated by injection-molding a resin that includes a silicon component into a mold having a structure capable of forming a bridge channel, an inlet, and an outlet. Alternatively, the microfluidic chip and the three-dimensional tube structure may be disassembled into arbitrary parts. The respective parts that constitute the microfluidic chip and the three-dimensional tube structure may be separately injection-molded, which are then bonded to each other to fabricate the microfluidic chip and the three-dimensional tube structure.

Preparation Example 1: Preparation of a Microfluidic Chip

Figure 13:
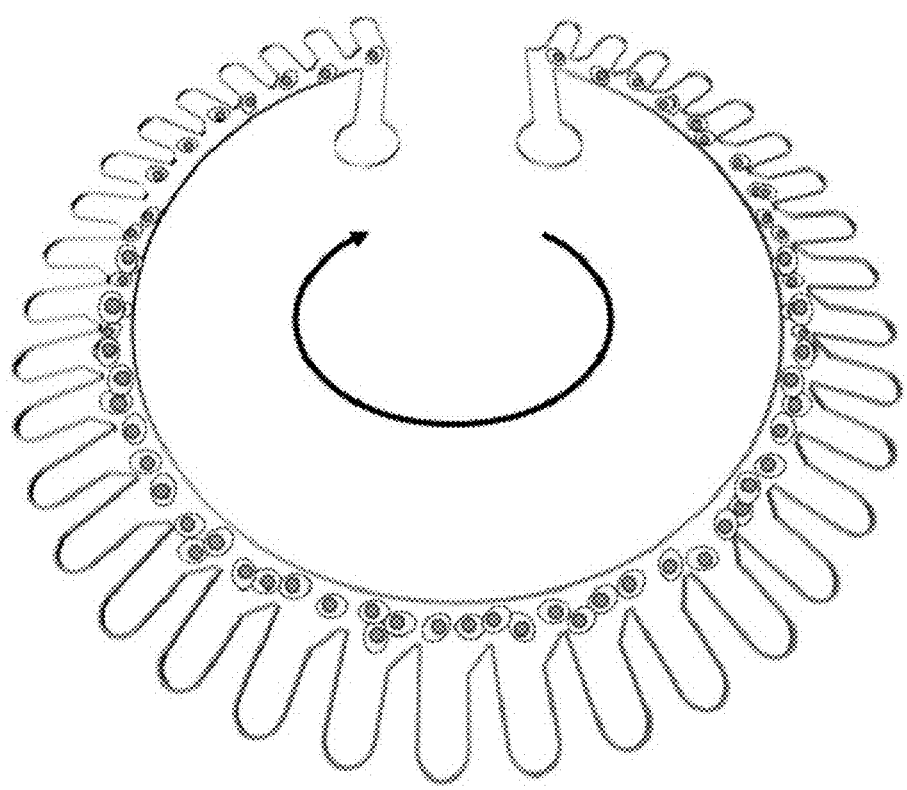
FIG. 13 shows a three-dimensional channel structure having a bridge channel in a circular shape and capable of positioning cells.
Figure 14A:
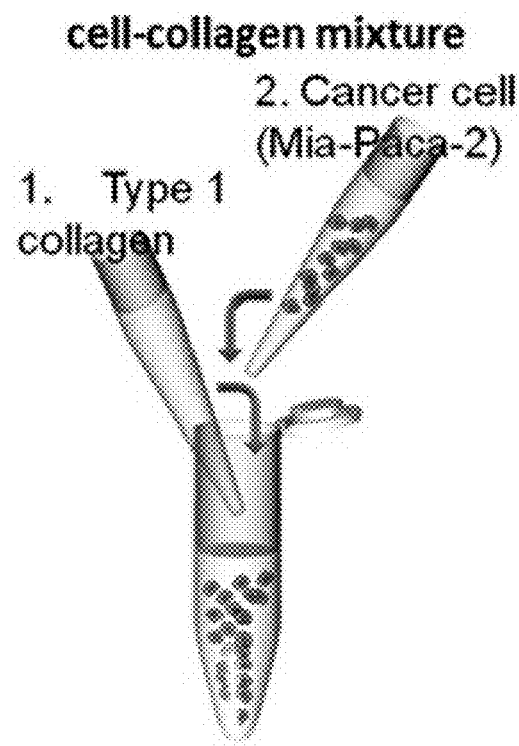
FIGS. 14A to 14F show a method of seeding cancer cells to a microfluidic chip.
Figure 14B:
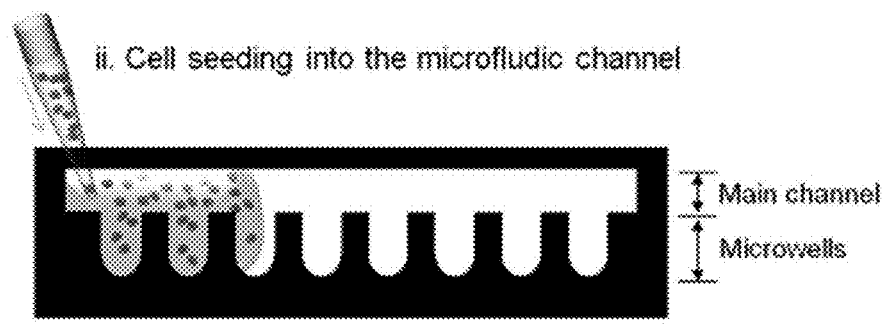
Figure 14C:
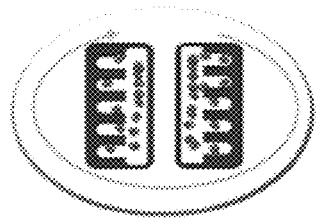
Figure 14D:
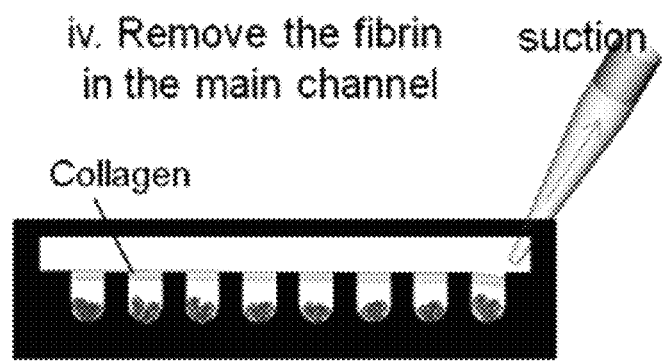
Figure 14E:
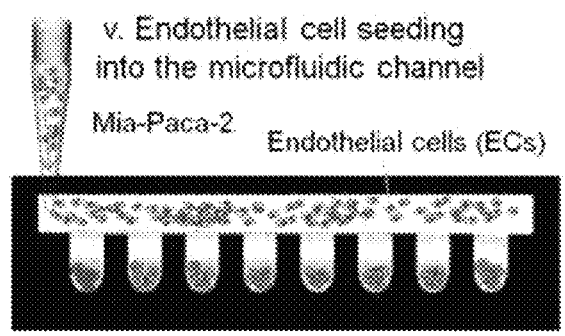
Figure 14F:
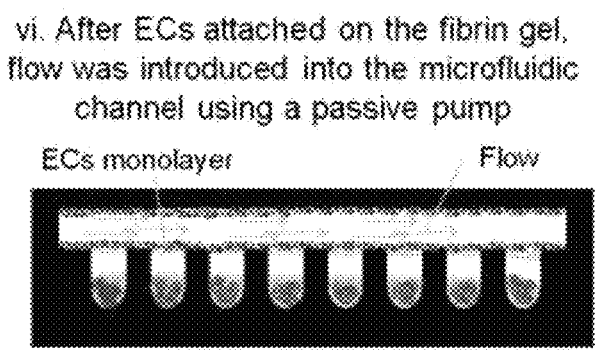

As shown in FIG. 13, a microfluidic chip was prepared, which had a structure including a bridge channel for injecting cells and collagen and a number of wells connected thereto. When the entire microfluidic chip was rotated using a centrifugal separator, the cells in the bridge channel before rotation moved to the bottom of the well in a short time. The centrifugal separation was carried out at a speed of 1,000 to 6,000 rpm for 10 seconds.

Example 1: Seeding of Cancer Cells into a Microfluidic Chip

Cancer cells were seeded into a microfluidic chip in the following manner.

First, a mixture of cells and liquid collagen was prepared. The cancer cells were mixed well with the liquid collagen (Type 1 collagen), so that the cancer cells were evenly distributed in the liquid collagen.

Second, a microfluidic chip made of silicone rubber was bonded to a substrate such as a cover glass or a slide glass. The collagen solution containing the cancer cells was then injected into the bridge channel of the microfluidic chip while preventing the formation of bubbles. The concentration of cells injected was $10^5$ to $10^6$ cells/ml.

Third, the cancer cells mixed with collagen, which existed in both of the bridge channel and the well, were subjected to centrifugal separation at room temperature at a speed of 2,000 rpm to allow the cancer cells to be located on the bottom of the well. Since it is difficult to inject cancer cells or other cells into the wells if collagen or matrix is gelated and becomes solid, the temperature of the microfluidic chip was maintained at 1° C. to 4° C. before the gelation in order to prevent collagen or matrix from becoming a gel. In addition, by repeating the first to third steps, various cells could be sequentially injected into the wells.

Fourth, any residual collagen or matrix remaining in the bridge channel was suctioned through the outlet or inlet connected to the bridge channel to be removed. In such event, the collagen, matrix, and other cells including the cancer cells injected into the well would remain in the well.

Fifth, in order to form a vascular structure, the microfluidic chip was put into a cell incubator at 37° C. after the suction step (i.e., the fourth step) to gelate the collagen and matrix. Thereafter, endothelial cells (ECs) were injected into the bridge channel using the methods of the first and second steps. After 2 to 3 hours of the injection into the bridge channel, the vascular cells attached to the matrix existing in the bridge channel and the well, thereby forming a vascular structure.

Sixth, after the vascular cells attached to the gel, a cell culture fluid was flowed using a manual pump to the bridge channel of the microfluidic chip.

This procedure is illustrated in FIG. 14A to FIG. 14F in that order.

Figure 15A:
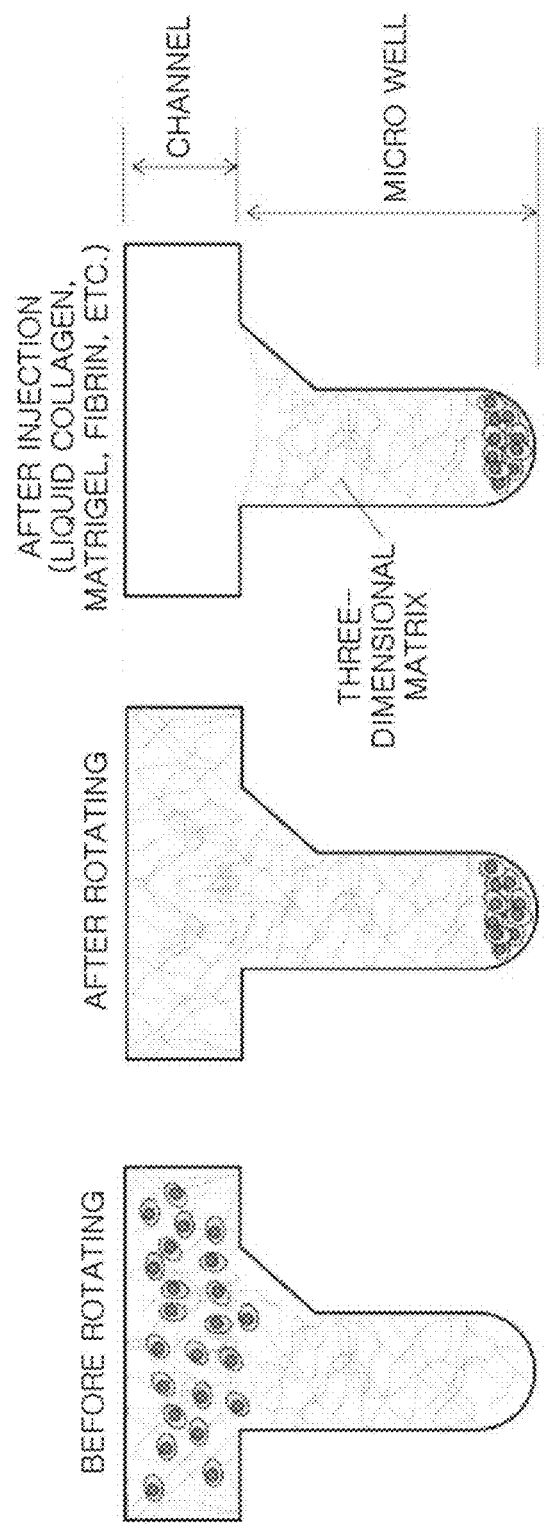
FIG. 15A schematically shows a state that cells are migrating to the inside of a well by centrifugal force.
Figure 15B:
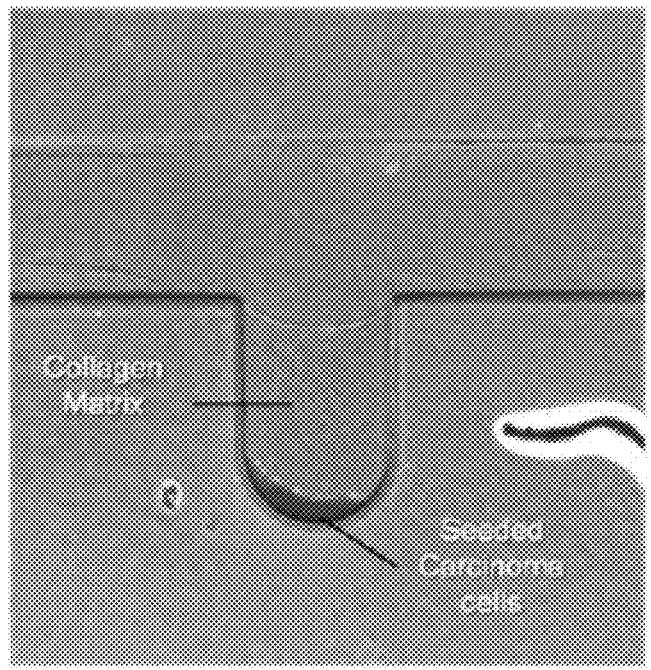
FIG. 15B is a photograph illustrating that the cells are positioned on the bottom of a well by centrifugal force.

In addition, FIGS. 15A and 15B show the state in which the residue of the bridge channel is suctioned after the cells were seeded into the fluid bridge channel of the microfluidic chip, followed by centrifugal separation to place the cells on the bottom of the well. FIG. 15B shows the result of observation of cells located in the wells with an optical microscope (EVOS, LifeScience, 40 magnification).

Example 2: Second Seeding of Fibroblasts (NIH-3T3) after First Seeding of Lung Cancer Cells (A549)

Figure 16A:
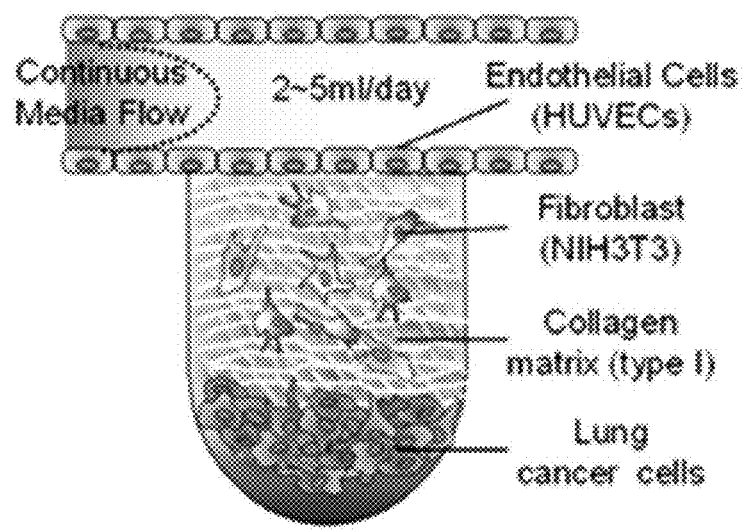
FIGS. 16A to 16C show the results obtained by injecting a lung cancer cell line (A549) as a primary seeding, injecting fibroblasts as a secondary seeding, and observing them with a fluorescence microscope and an optical microscope.

Lung cancer cells (A549) were placed on the bottom of the wells using the method depicted in FIG. 14A to FIG. 14F of Example 1. Thereafter, fibroblasts (NIH-3T3, ATCC) were secondly seeded. A cell culture fluid containing HUVEC cells was flowed in the direction of the arrow as shown in FIG. 16A to seed the vascular cells in the fluid bridge channel.

Here, the lung cancer (A549) cell line (ATCC, CCL-185, Manassas, Va., USA) and the fibroblast (NIH-3T3) cell line (ATCC, mouse fetal fibroblast cell line, CRL-1658, Manassas, Va., USA) were cultured using RPMI-1640 (Thermo Fisher Scientific, MA, USA) containing 10% fetal bovine serum (FBS, Biowest, MO, USA) and 1% antibiotic (Thermo Fisher Scientific) and Dulbecco's modified Eagle Medium (Thermo Fisher Scientific). Human umbilical vein endothelial cells (HUVECs, ATCC, CRL-1730, Manassas, Va., USA) were cultured in a medium containing EGM2 (Lonza, Basel, Swiss) and 1% antibiotics. In such event, in order to prepare an in vitro tumor model, collagen premixed with lung cancer cells (A549) to fill the well was injected through the inlet into the microfluidic chip, which was subjected to centrifugal separation (KA.MC-01, Korea Ace Scientific, Seoul) at 6,000 rpm for 30 seconds, through which the cancer cells could be injected into the wells of the microfluidic chip.

Figure 16B:
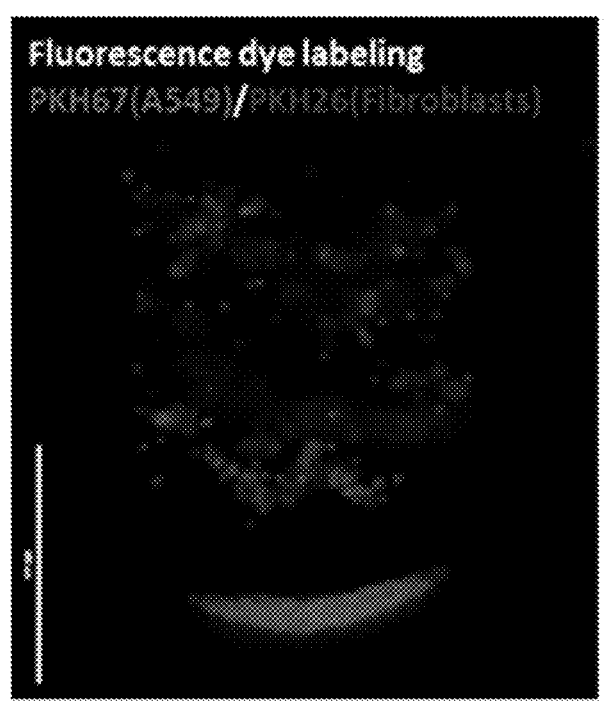
Figure 16C:
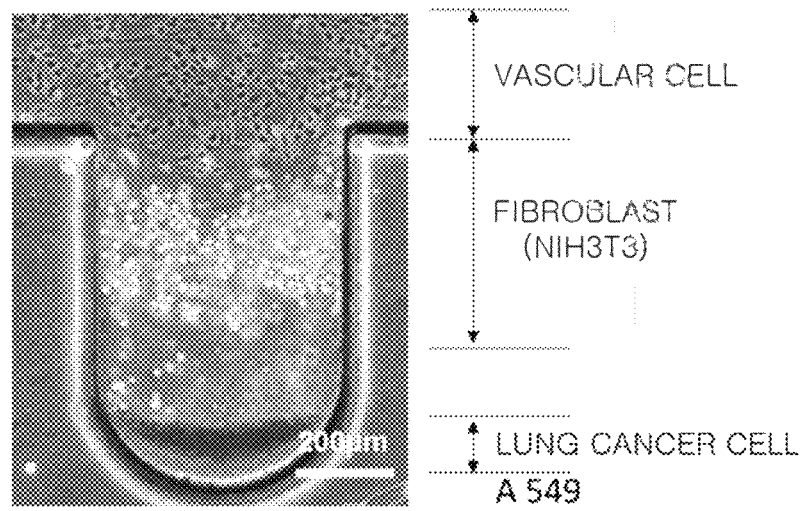

FIG. 16B shows the result of observing lung cancers (A549) and fibroblasts (Fibroblast, NIH-3T3) with a fluorescence microscope (EVOS, LifeScience, 100 magnification). FIG. 16C shows the result of observation of lung cancer cells (A549), fibroblasts, and vascular cells (HUVECs) with an optical microscope (EVOS, LifeScience, 100 magnification). The lung cancer cells (A549) were fluorescence stained with PKH67 (Sigma-Aldrich), and the fibroblasts were fluorescence stained with PKH26 (Sigma-Aldrich) using the method provided by the supplier. They were then seeded into the microfluidic chip in the same manner as in Example 1. The seeded cells were observed using a fluorescence microscope (EVOS, LifeScience, 100 magnification).

It was confirmed from the results of these experiments that the first-seeded lung cancer cells (A549) were located on the bottom of the well in the microfluidic chip of the present invention, that the second-seeded fibroblasts were layered on the lung cancer cells (A549), and that a vascular structure was formed around the bridge channel, thereby simulating the environment in the body.

Example 3: Seeding of Pancreatic Cancer Cells into a Microfluidic Chip

In order to observe the migration of pancreatic cancer cells, growth through proliferation, and infiltration into surrounding tissues, as shown in FIGS. 17A to 17D, pancreatic cancer cells (Mia Paca-2, ATCC) were first seeded into a microfluidic chip, and vascular cells were secondly seeded, using the same method as in Example 2.

Cancer cells develop through the processes of infiltration into the surrounding tissues, growth, passage through the blood vessels, intravascular migration, and then metastasis to other organs. Thus, the migration of cancer cells in the direction of the bridge channel (upwards) indicates that infiltration and growth were occurring in the early stages during the metastasis process.

Figure 17A:
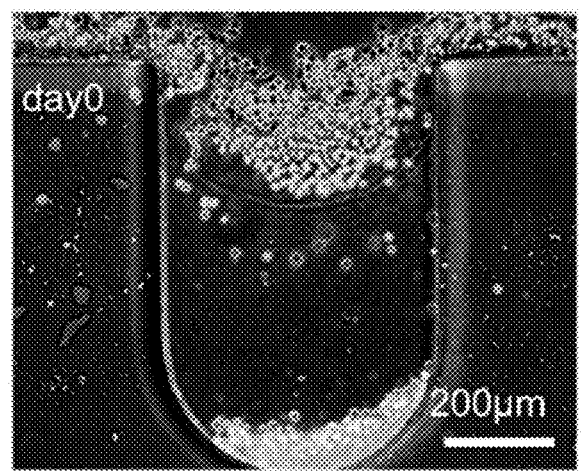
FIGS. 17A to 17D show that pancreatic cancer cells that have been injected into a microfluidic chip have grown and are migrating toward the vascular structure.
Figure 17B:
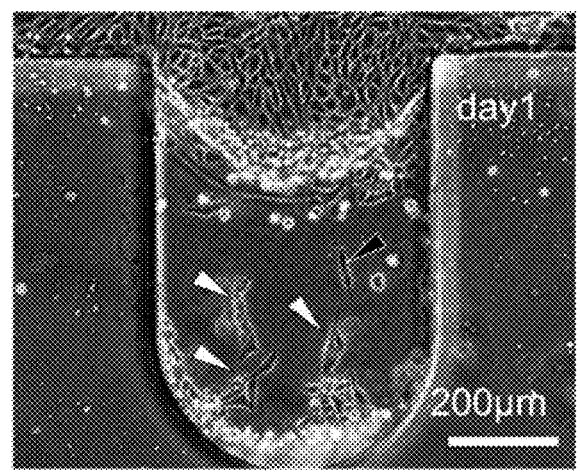
Figure 17C:
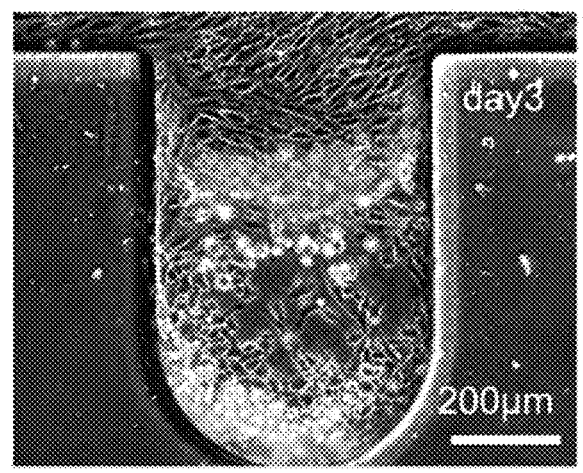
Figure 17D:
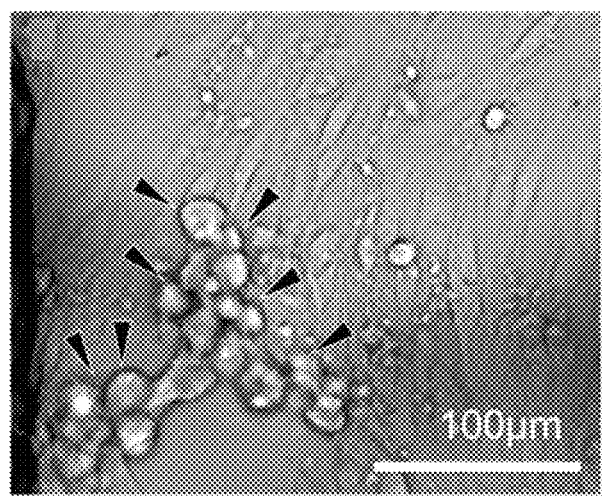

FIG. 17A shows an initial seeding of pancreatic cancer cells, FIG. 17B shows that the cells migrated after one day, FIG. 17C shows the growth of the cells by proliferation, and FIG. 17D shows a phenomenon in which the vascular tissue was destroyed by the pancreatic cancer cells as observed through a fluorescence microscope in the same manner as in Example 2.

Example 4: Formation of Multicellular Tumor Spheroids

In many cases, lung cancer is observed in large tissue forms such as multicellular tumor spheroids. Thus, experiments were conducted to see whether cells cultured in a microfluidic chip according to an embodiment of the present invention would develop to form multicellular tumor spheroids.

Figure 18:
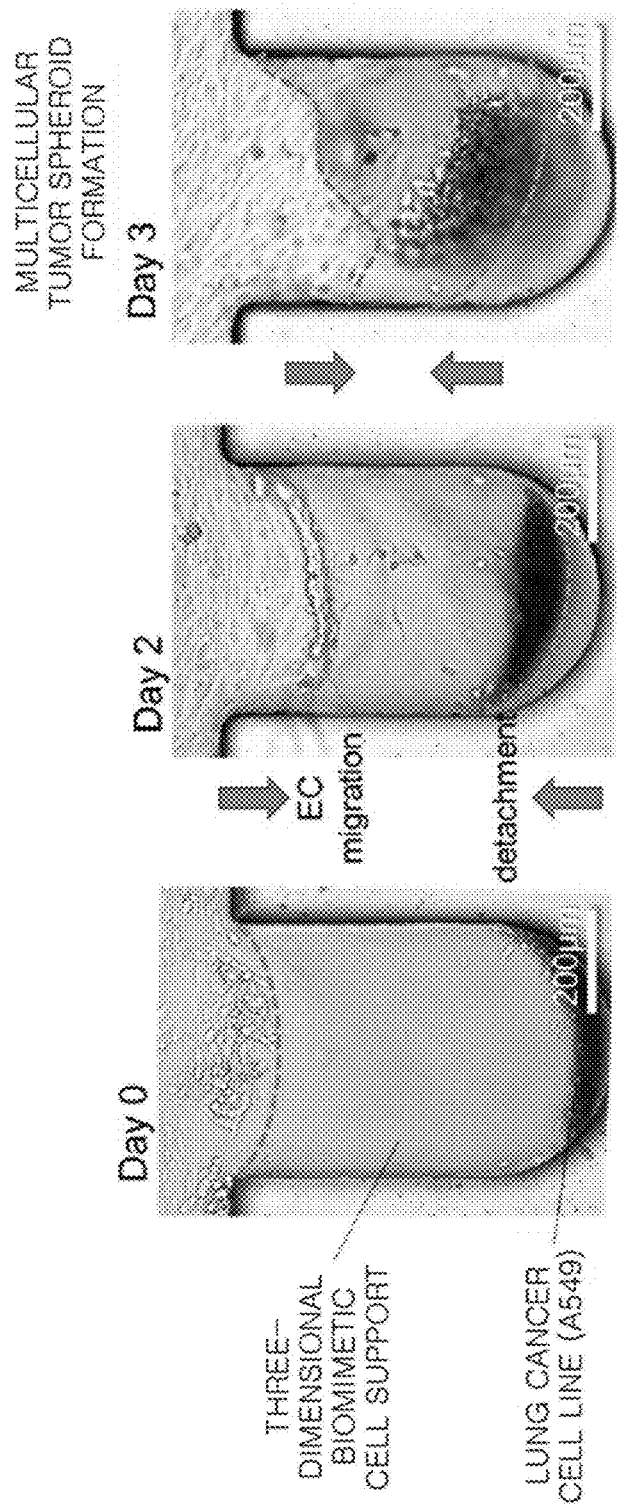
FIG. 18 shows that lung cancer cells that have been injected into a microfluidic chip have grown to become multicellular tumor spheroids.

In order to observe the formation of multicellular tumor spheroids by lung cancer cells, as shown in FIG. 18, lung cancer cells (A549) were seeded into a microfluidic chip using the same method as in Example 2, and the developmental process of the cancer cells was observed using an optical microscope (EVOS, LifeScience, 100 magnification).

As a result, as shown in FIG. 18, one day after seeding the lung cancer cells, the lung cancer cells migrated towards the channel (upper, green arrow direction), and vascular cells migrated towards the bottom of the well (lower, blue arrow direction). After 3 days of the seeding the lung cancer cells, the lung cancer cells and vascular cells migrated further and formed multicellular tumor spheroids.

In order to observe the process by which tumor cells form multicellular tumor spheroids through interaction with the surrounding tissues, as shown in FIG. 19, multicellular tumor spheroids were formed in a microfluidic chip using the same method as in Example 1. They were observed using an electron microscope (CeronTech, AIS 2100C) and a fluorescence microscope in the following manner.

The multicellular tumor spheroids were fixed for 10 minutes at room temperature by 4% paraformaldehyde diluted in a PBS buffer. Thereafter, 100% methanol refrigerated at −20° C. was added at room temperature for 5 minutes. After incubation, the fluid path was washed five times with a chilled PBS buffer. The tumor spheroids were permeated with a PBS buffer containing 0.1% Triton X-100 by incubation at room temperature for 40 minutes, followed by blocking with a 2% bovine serum albumin solution added to a PBST buffer (containing 0.1% Tween 20) for 45 minutes. Then, a primary antibody was added to a PBST buffer containing 1% bovine serum albumin at 4° C. to incubate. Thereafter, the cells were washed with a PBS buffer for 5 minutes, followed by addition of secondary antibodies (Alexa Fluor 488 and Alexa Fluor 647 from Abcam, Cambridge, UK; CFL 488 from Santa Cruz, Dallas, Tex., USA) and incubation for 4 hours.

Then, they were washed again with a PBS buffer solution. The cell nuclei were stained with 4,6-diamidino-2-phenylindole dihydrochloride (DAPI; Invitrogen, Waltham, Mass., USA) for comparison. The primary antibodies against Ki-67 (Abcam), von Willebrand factor (vWF; Santa Cruz), and vascular endothelial growth factor (VEGF; Abcam) were used to observe the tumor formation. Matrix metalloproteinase-1 (MMP-1; Abcam) was used to observe the migration of endothelial cells (ECs) and the separation of the extracellular matrix (ECM). Fluorescence images were obtained using a fluorescence microscope (EVOS; Life Technologies) and a confocal microscope (Zeiss LSM780; Carl Zeiss AG, Oberkochen, Germany).

The results are shown in FIGS. 19A to 19D. The proliferation of cancer cells was confirmed by staining with KI-67 in FIG. 19A, which was obtained by using a microscope.

Figure 19A:
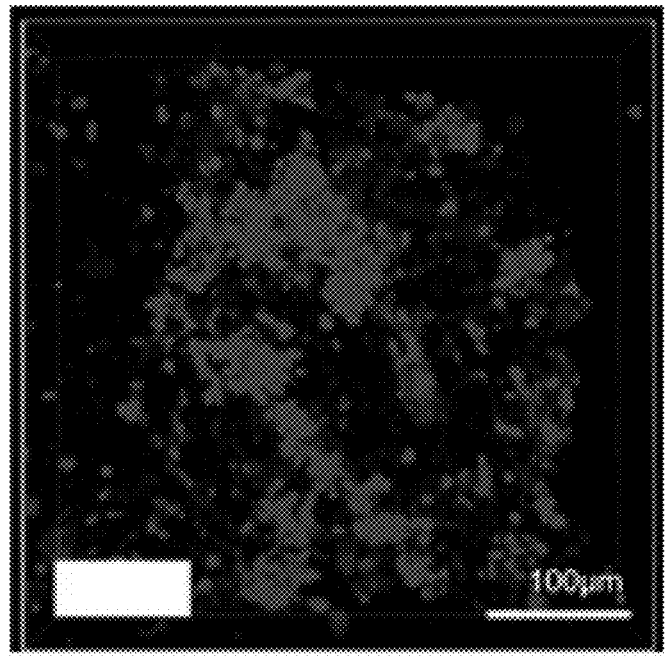
FIGS. 19A to 19D show the results of observing the lung cancer cells injected in FIG. 18, a collagen matrix, and vascular cells formed as one tissue with a fluorescence microscope "a", a confocal microscope "b", and electron microscopes "c" and "d".
Figure 19B:
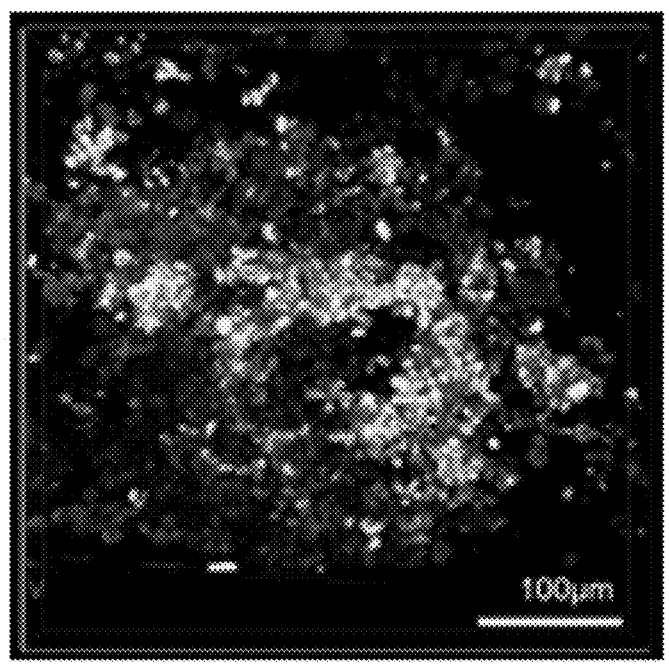
Figure 19C:
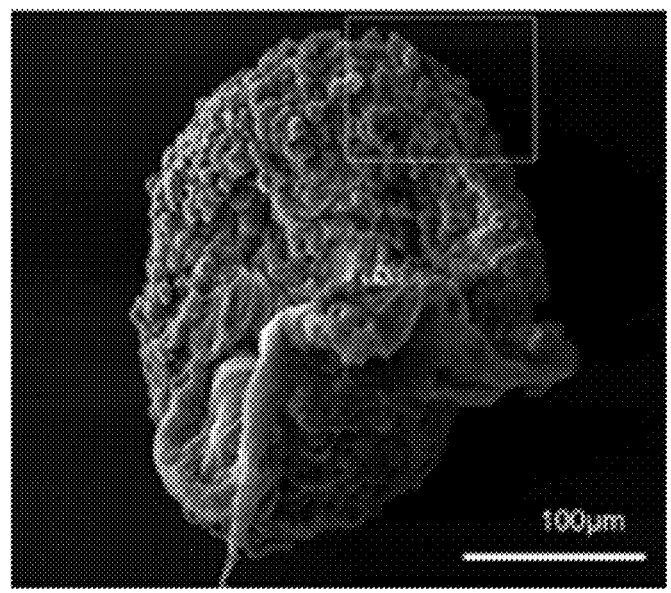
Figure 19D:
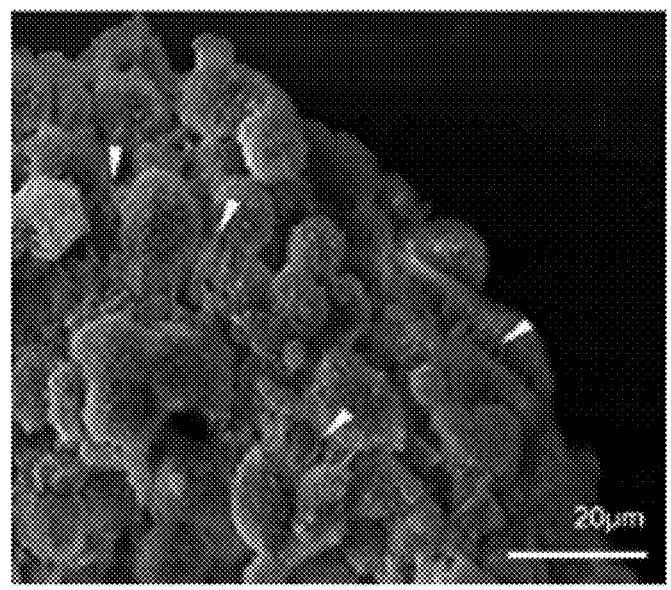

The structure of the surface of the multicellular tumor spheroids was specifically observed using the results of electron microscopic observation of FIGS. 19C to 19D. FIG. 19C shows the results of observation of the multicellular tumor spheroids by an electron microscope, and FIG. 19D is an enlarged view of the white box region of FIG. 19C. The white wedge represents the extracellular matrix produced by the cells.

The results of observation with an electron microscope and a fluorescence microscope of FIGS. 19A to 19D indicate the intercellular location, the degree of proliferation of cancer cells, and the intercellular connectivity.

Example 5: Evaluation of the Pharmacological Efficacy of Gemcitabine Using a Microfluidic Chip In order to evaluate the efficacy of an anticancer medicine using a microfluidic chip, pancreatic cancer cells (Mia Paca-2, ATCC) were seeded into a microfluidic chip using the same method as in Example 2. Secondarily, vascular cells (HUVEC, purchased from ATCC) were seeded. Once the cells were confirmed to be attached (day 0: cell seeding date), gemcitabine (Eli Lilly and Company, USA) was administered 3 days later to measure the spread range of the cancer cells.

Figure 20A:
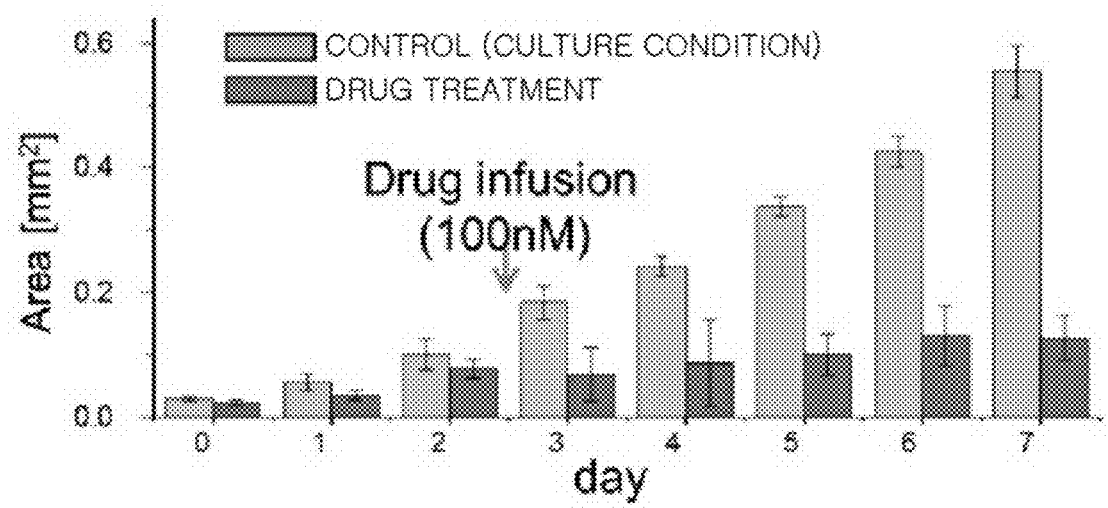
FIGS. 20A to 20C show the results of measuring the distribution areas of cancer cells and the rates at which the cancer cells reach the vascular structure after treating the pancreatic cancer cells seeded in FIGS. 17A to 17D with gemcitabine.
Figure 20B:
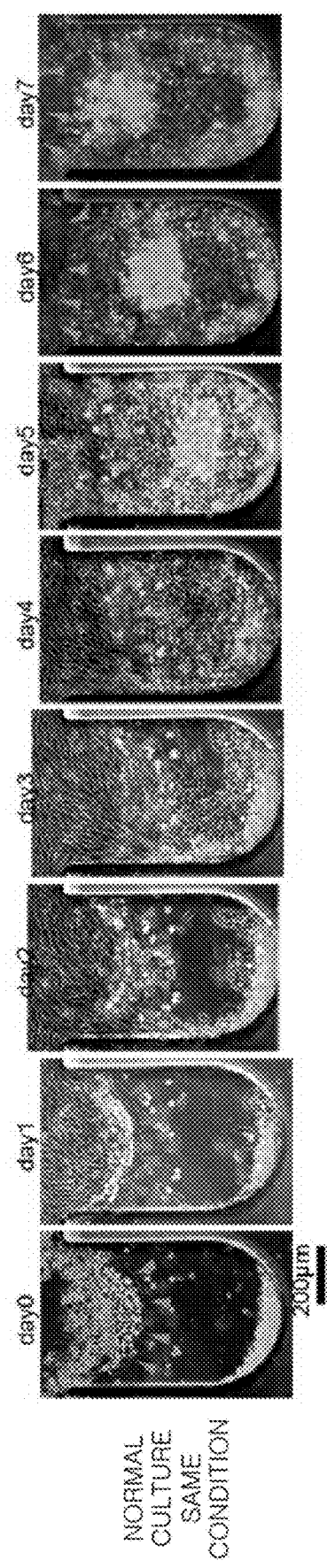
Figure 20C:
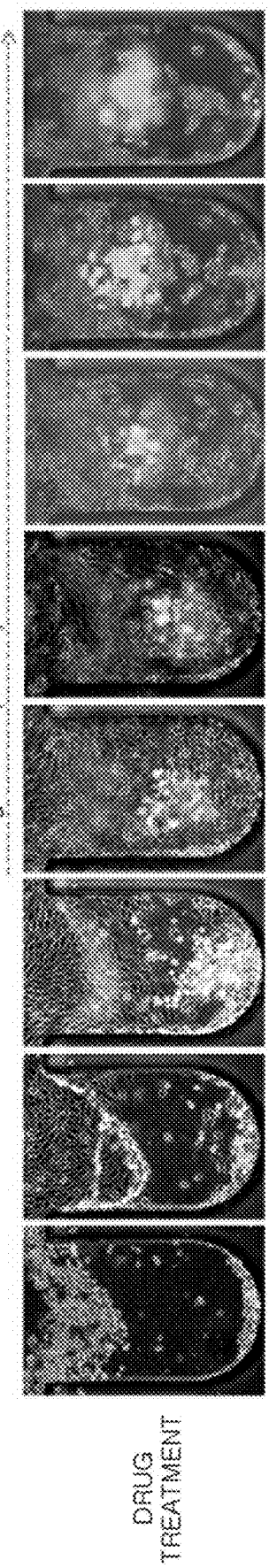

As shown in FIGS. 20A to 20C, the growth and development of cells were observed from the time of cell seeding (day 0) to the 7th day after the drug treatment (day 3). For observation of the cells, an optical microscope image (EVOS, LifeScience, 100 magnification) and a fluorescence microscope image (EVOS, LifeScience, 100 magnification) were superposed.

FIGS. 20B and 20C show the results of observation of the cell development using an optical microscope and a fluorescence microscope. The eight images of FIG. 20B, labeled as normal cultures, were those treated with DMSO at day 3 and observed up to day 7. The eight pictures of FIG. 20C, labeled drug treatment, were those treated with gemcitabine on day 3 and observed up to day 7. FIG. 20A is a graph in which the growth width of the cancer cells was statistically quantified from FIGS. 20B and 20C using an Origin Pro 8 (Origin Lab, Northampton, Mass., USA., ±5%, significance: 0.001).

As shown in FIGS. 20A to 20C, the distribution area of the cancer cells was decreased when the cells were treated with gemcitabine as compared with when the cells were not treated with gemcitabine. These results show that treatment with gemcitabine inhibits the growth of pancreatic cancer cells.

Example 6: Evaluation of the Pharmacological Efficacy of an MMP-1 Inhibitor Using a Microfluidic Chip In order to evaluate the efficacy of an anticancer medicine using a microfluidic chip, lung cancer cells (A549, ATCC) were seeded into a microfluidic chip using the same method as in Example 1. Secondarily, vascular cells were seeded (day 0). An MMP-1 inhibitor (MMP-1 inhibitor GM6001 (Santa Cruz, Dallas, Tex., USA)) was administered 1 day later to observe the changes in the proliferation of cancer cells with an optical microscope (EVOS, LifeScience, 100 magnification) as shown in FIG. 21A.

Figure 21A:
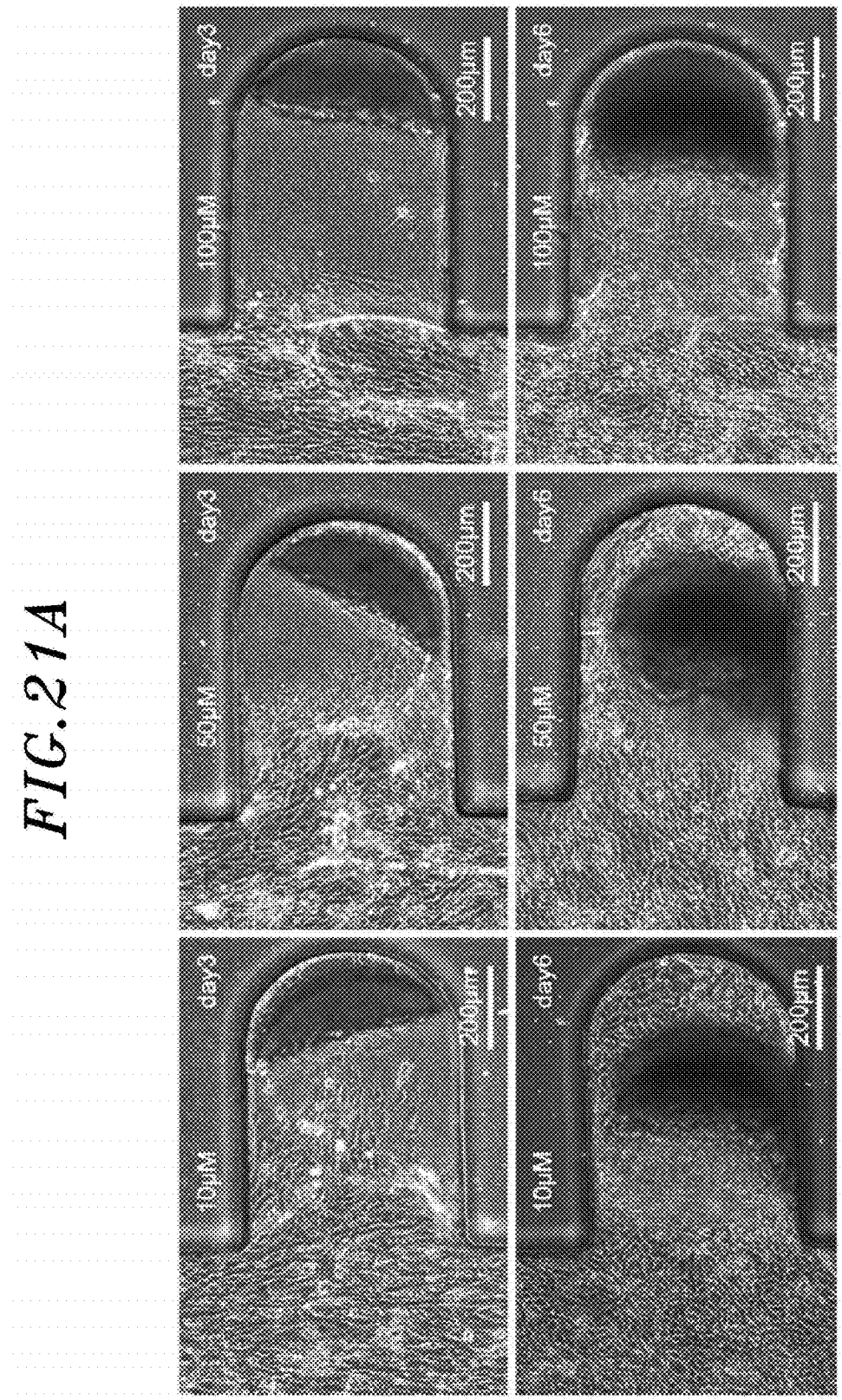
FIGS. 21A to 21C show the results of observing cells with an optical microscope after treating the lung cancer cells seeded in FIG. 18 with an MMP-1 inhibitor (Matrix metalloproteinase-1 inhibitor).
Figure 21B:
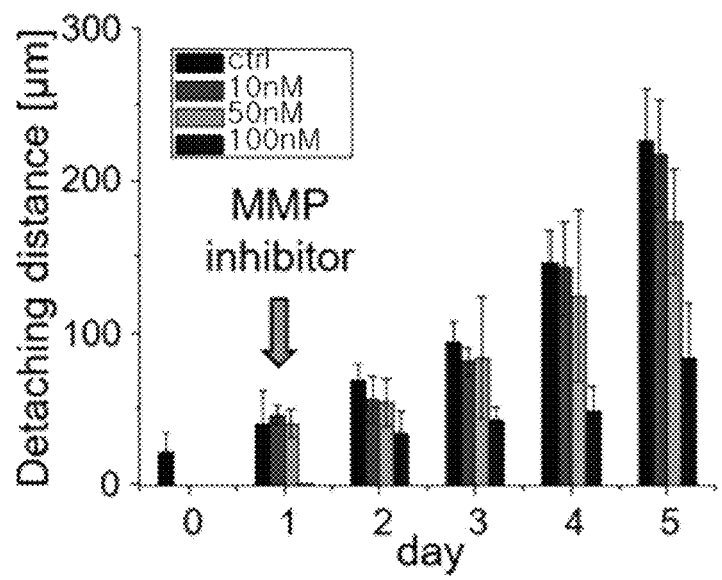
Figure 21C:
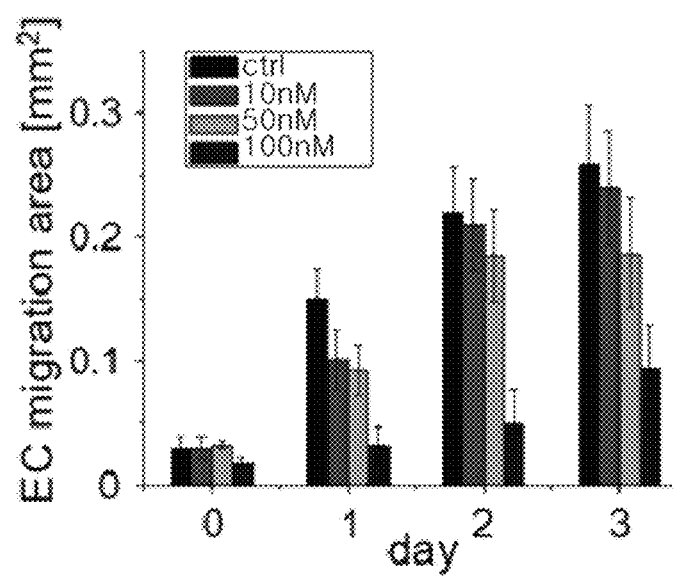

In addition, as shown in FIGS. 21B and 21C, the cells were treated with the MMP-1 inhibitor at increased concentrations to observe the travel distances of cancer cells, the migration area of vascular cells from the results of FIG. 21A, which statistically quantified using the same method as in Example 5. As a result, it was confirmed that as the concentration of the MMP-1 inhibitor was increased for the treatment and culture, the travel distance of the lung cancer cells was gradually reduced and that the migration area of the vascular cells was reduced. These results indicate that the treatment of an MMP-1 inhibitor drug inhibits the metastatic process of lung cancer cells cultured in the cell culture device of the present invention.

Example 7: Formation of a Patient-Derived Lung Cancer Organoid

In many cases, lung cancer is observed in large tissue forms such as multicellular tumor spheroids. Thus, experiments were conducted to see whether patient-derived lung cancer cells cultured in a microfluidic chip of the present invention would develop to form a tumor organoid.

The term "organoid" refers to an organization of cells formed in vitro, which has the features of an organ. Since organs are formed from one cell similarly to stem cells, it is used to study organogenesis and drug efficacy. In addition, a tumor organoid is an organization, which is formed by the continuous growth of tissue cells developed into tumor cells. The tumor organoid has the features of the original tissue and the features of the tumor.

Cancer tissues of the patients allowed for research for tissue examination were isolated, and the patient-derived cancer cells were seeded into a microfluidic chip in a cell culture device using the same method as in Example 2. Once a culture fluid was continuously injected through the bridge channel for 2 weeks, the developmental process of tumor organoids was observed by date using an optical microscope (EVOS, LifeScience, 100 magnification).

Figure 22:
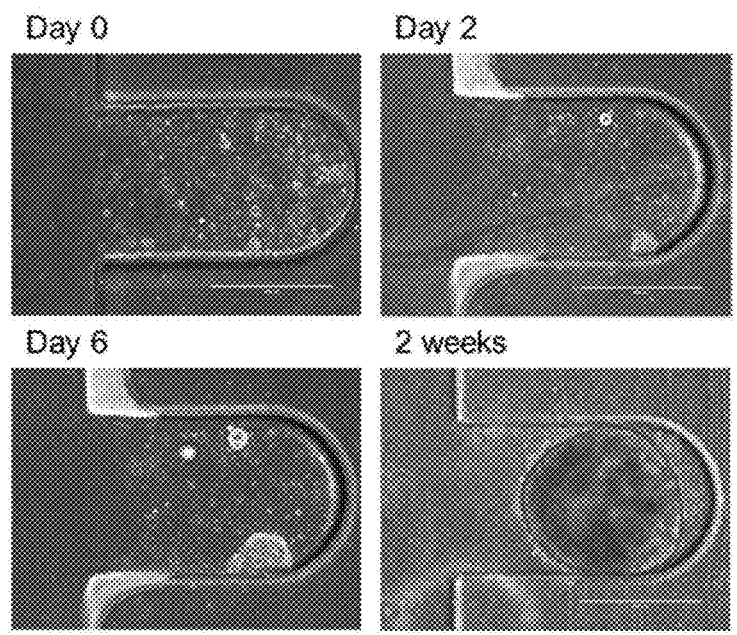
FIG. 22 shows the developmental process of a tumor organoid by date observed with an optical microscope.
Figure 23:
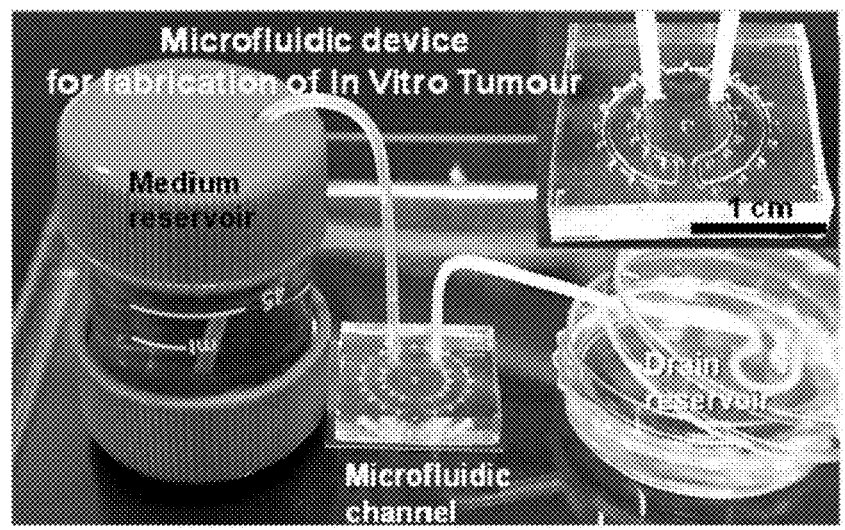
FIG. 23 is a photograph illustrating the configuration of supplying a fluid to a microfluidic chip according to an embodiment of the present invention.
Figure 24:
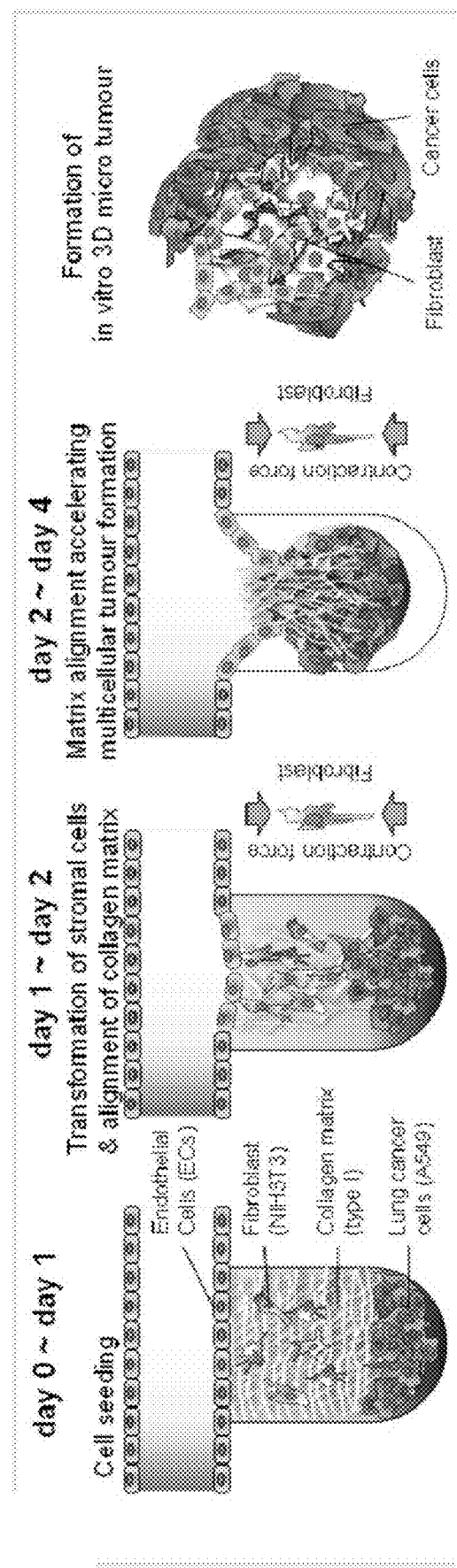
FIG. 24 shows the process in which a tumor is formed by interaction between tumor cells and surrounding tissues.
Figure 25:
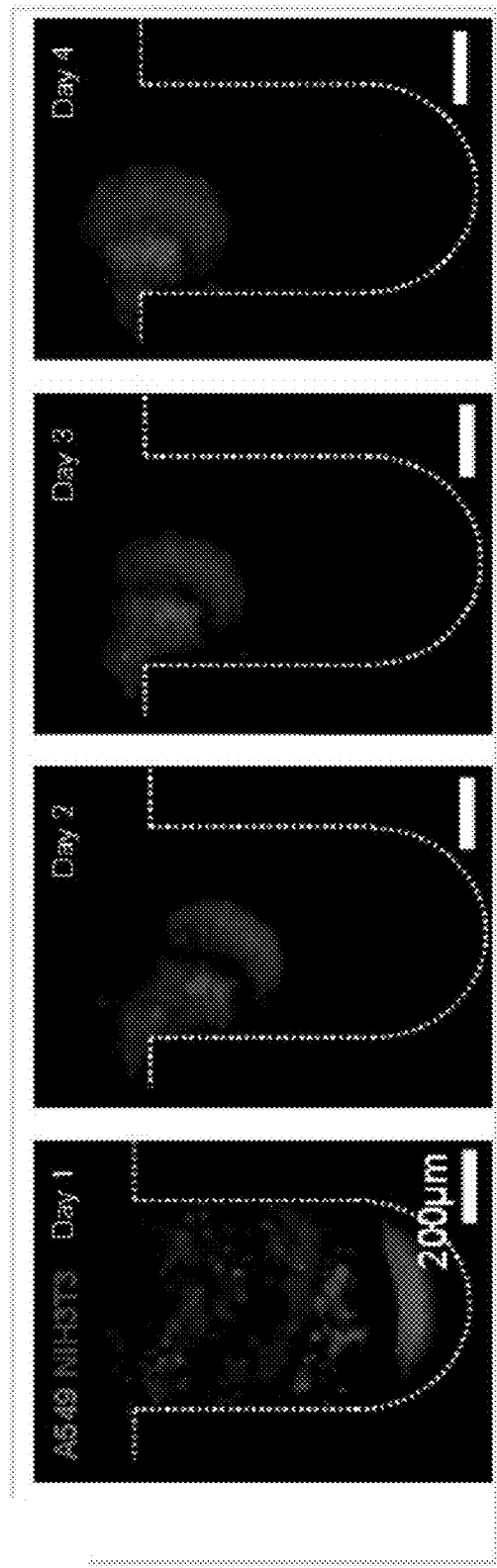
FIG. 25 shows the process in which a tumor is formed by date.
Figure 26:
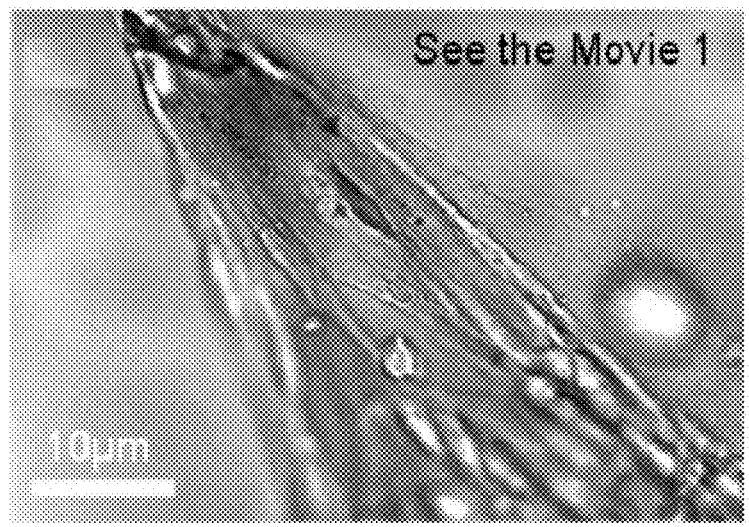
FIG. 26 shows that vascular cells and fibroblasts are aligned and pull up tumor cells while a tumor tissue is being formed.
Figure 27:
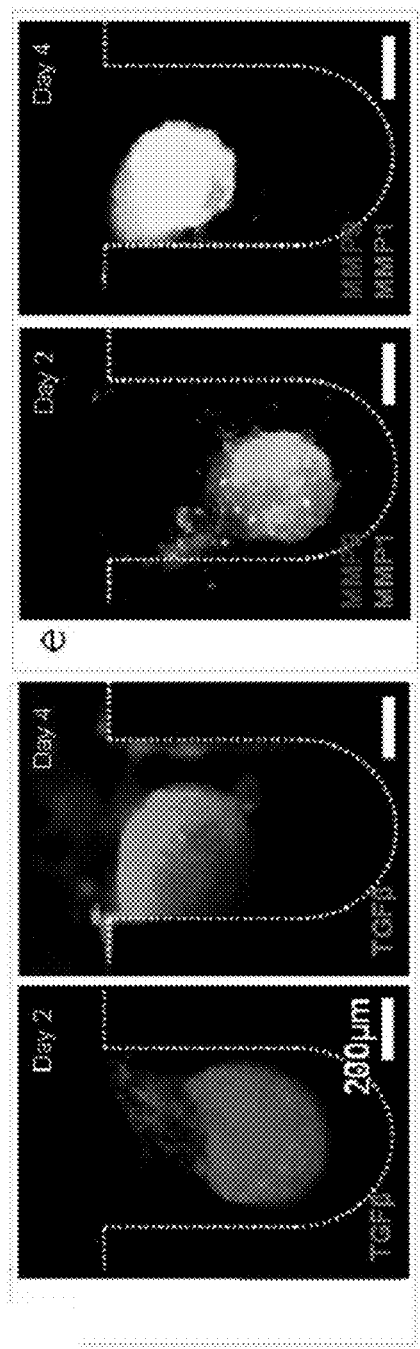
FIG. 27 shows that a shape regulating factor (TGFβ) is expressed in a tumor formation process, and a substrate proteolytic enzyme (MMP1, 9) is expressed to accelerate the tumor formation.
Figure 28:
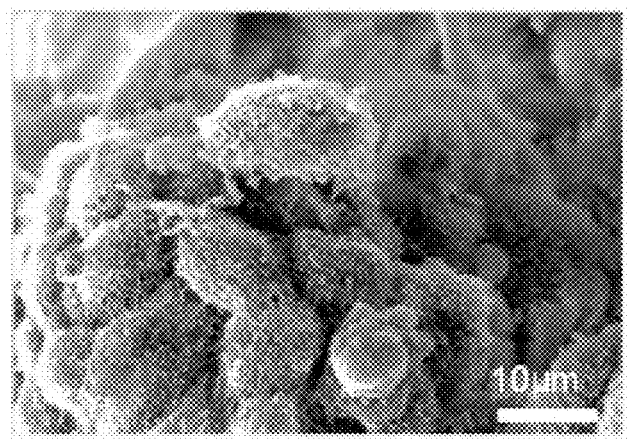
FIG. 28 is a photograph showing the surface of a cultured tumor tissue.
Figure 29:
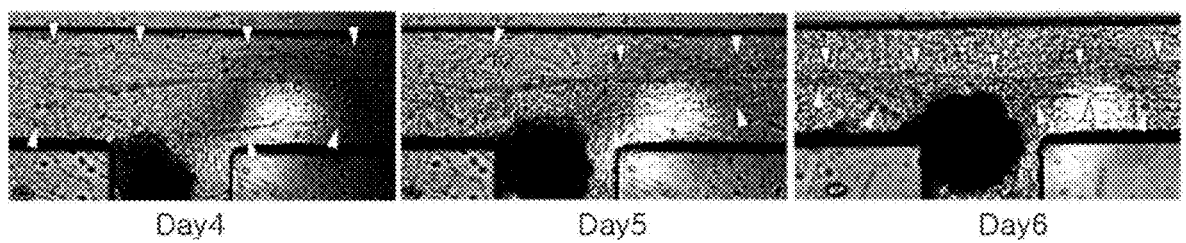
FIG. 29 is a photograph showing a process in which blood vessels are formed in a channel in the process of forming an in vitro tumor model.
Figure 30:
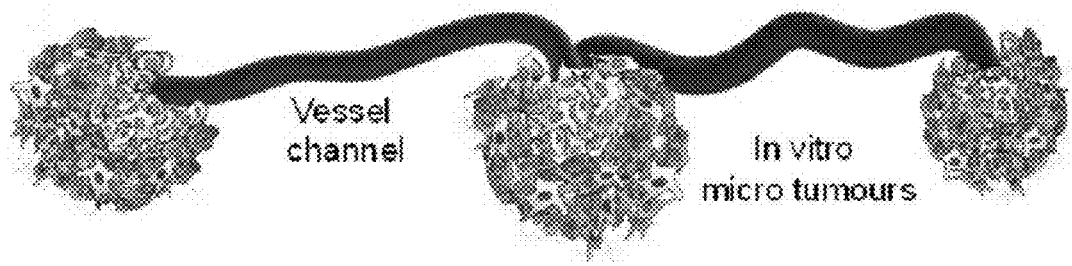
FIG. 30 shows modeling of the formation of a tumor in a channel.
Figure 31:
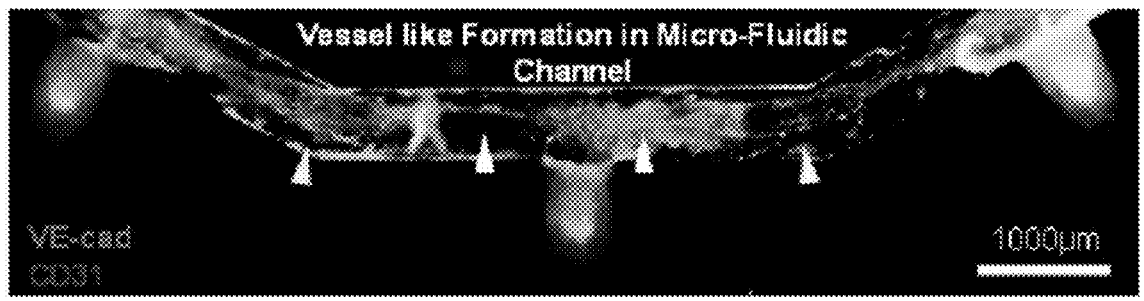
FIG. 31 is a fluorescence image showing that a tumor is formed in a channel.
Figure 32:
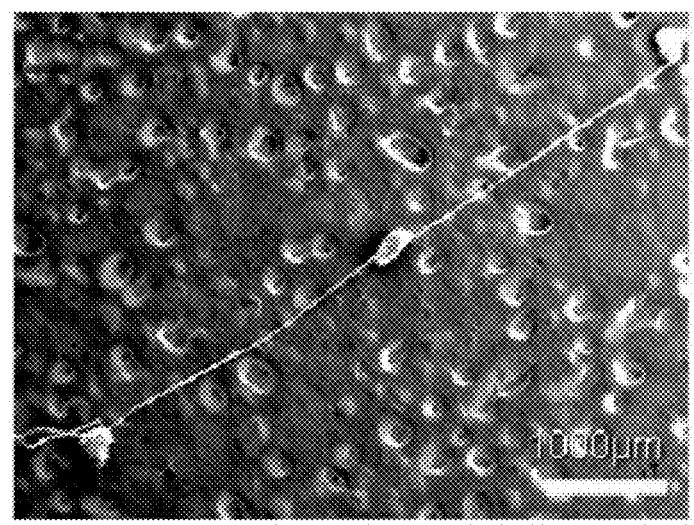
FIG. 32 is an electronic scanning microscope photograph of a tumor model in which a vascular network is formed.
Figure 33:
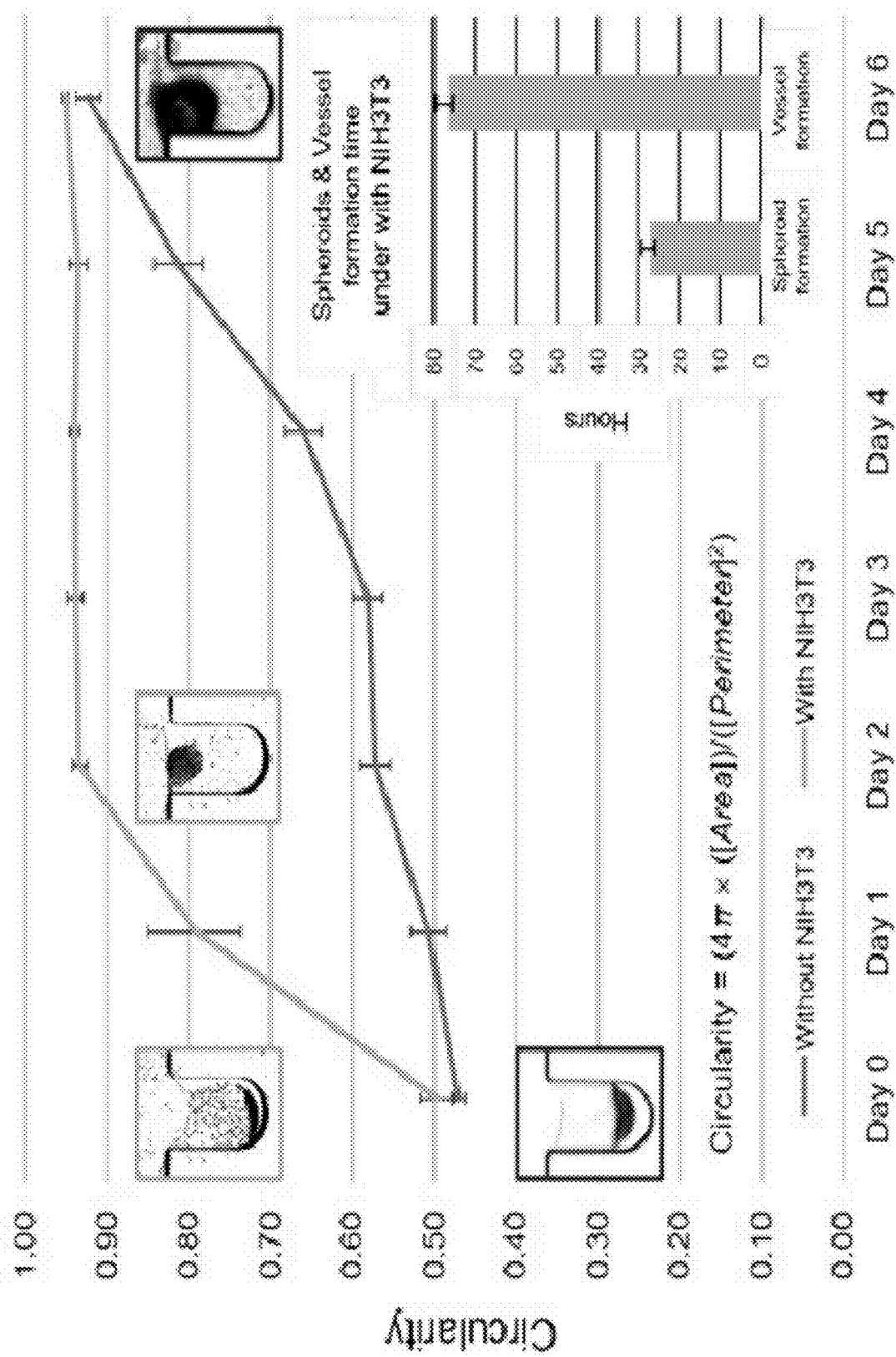
FIG. 33 is a graph showing the period of time when a tumor is formed.
Figure 34A:
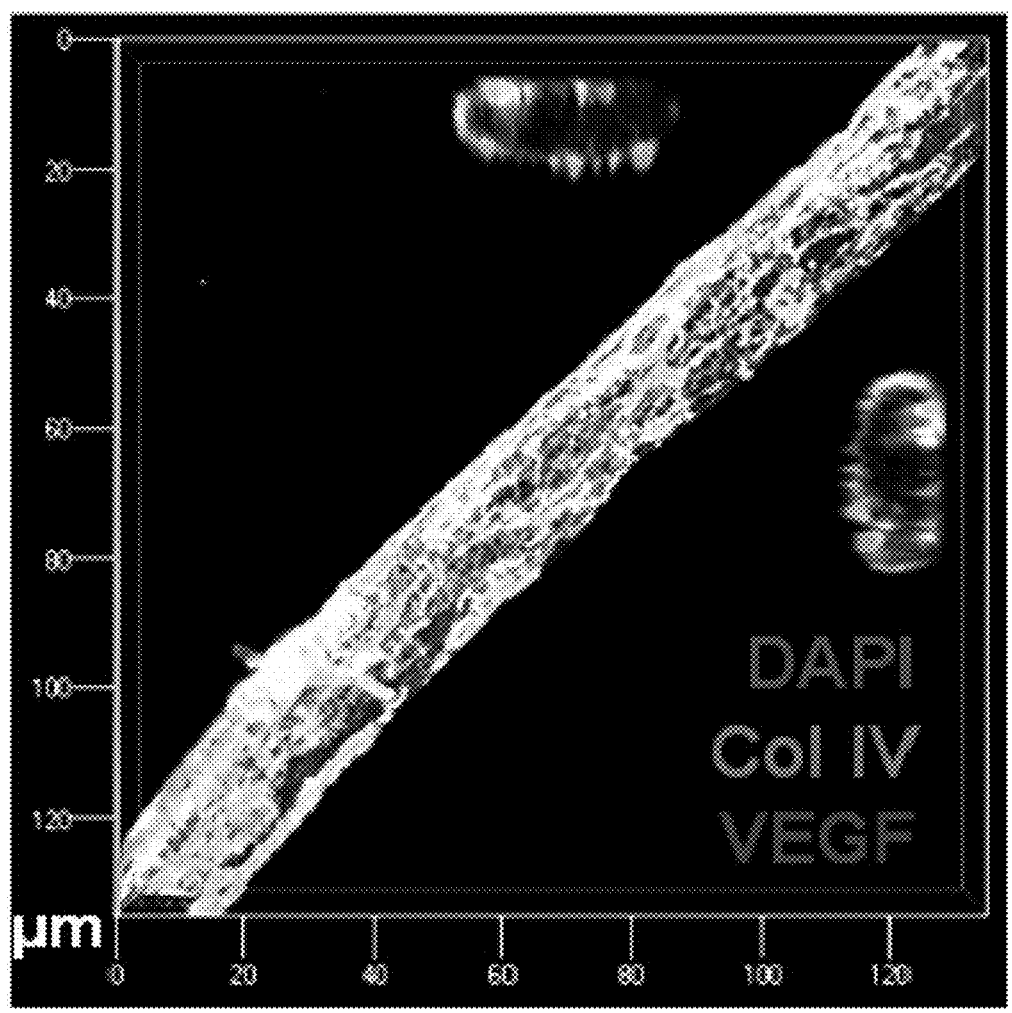
FIGS. 34A to 34D are photographs taken by tomography and three-dimensional analysis using confocal microscope photographs.
Figure 34B:
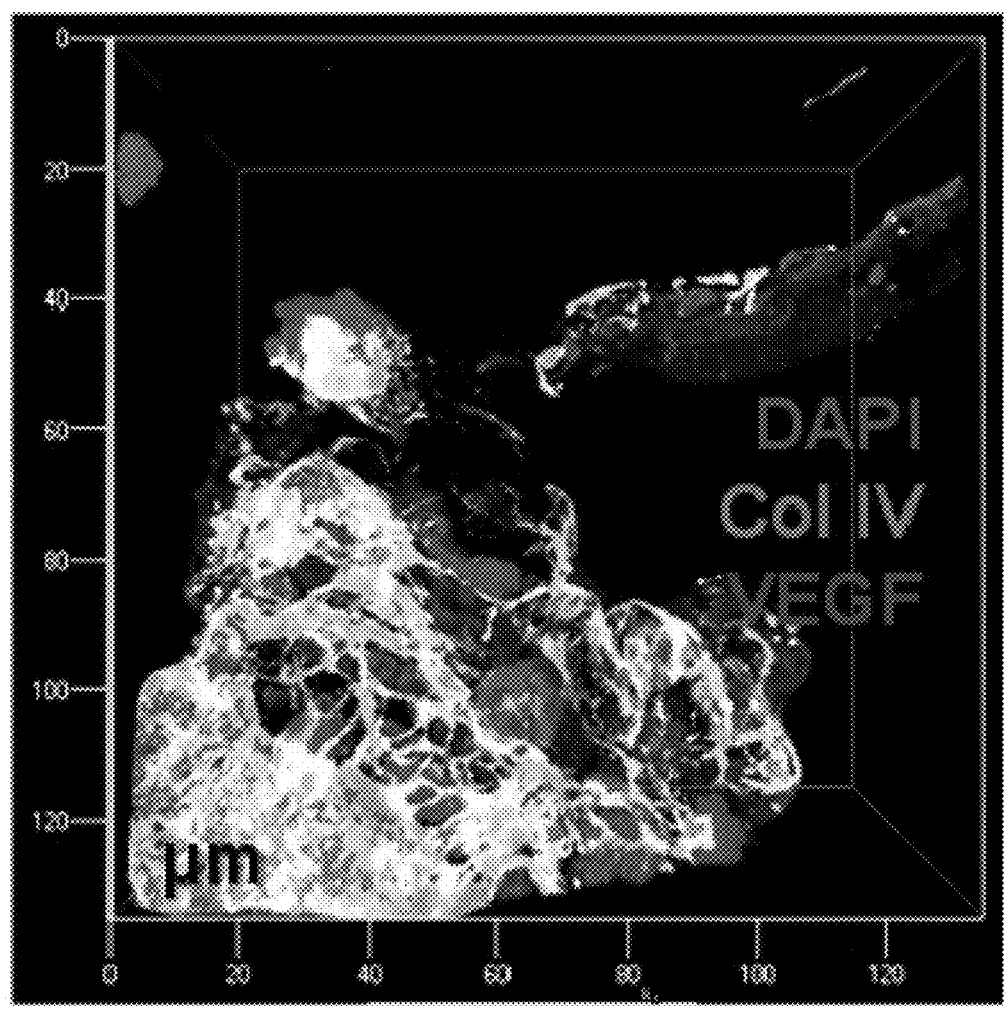
Figure 34C:
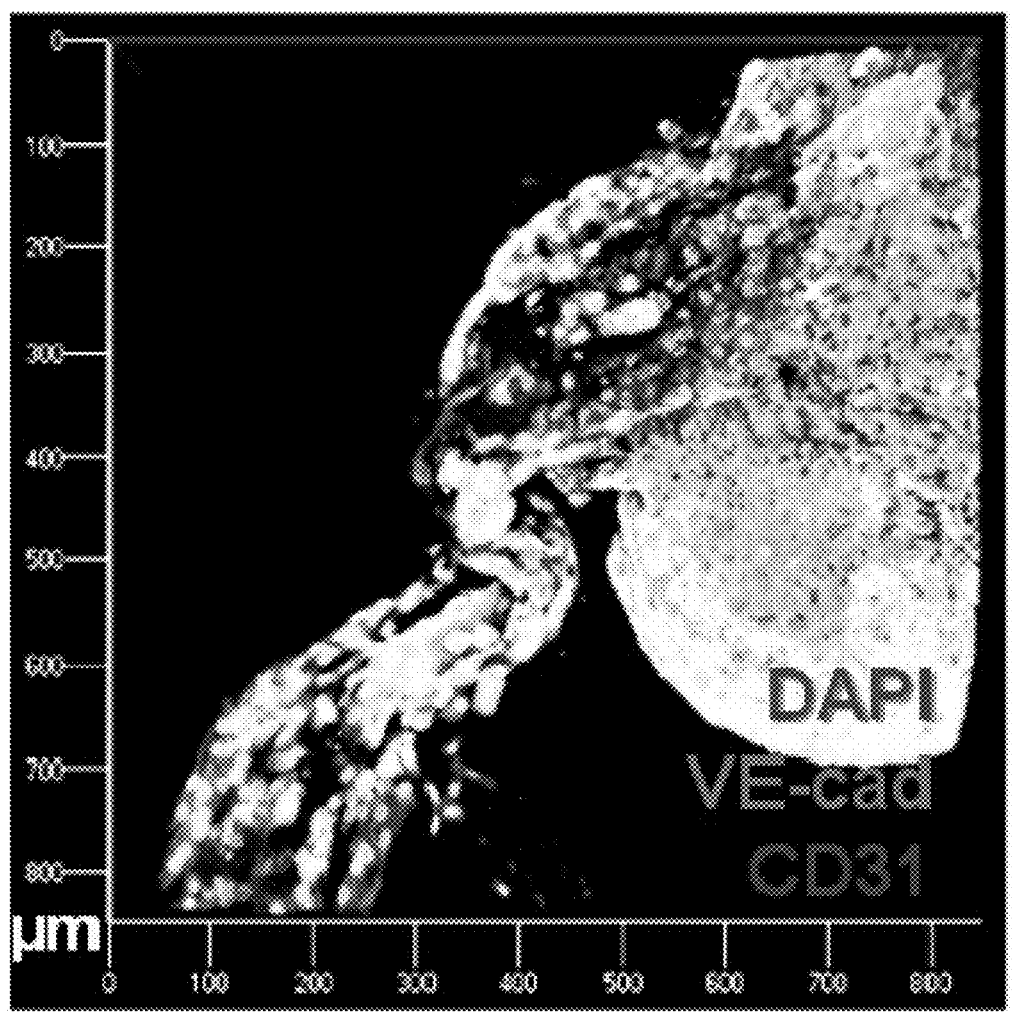
Figure 34D:
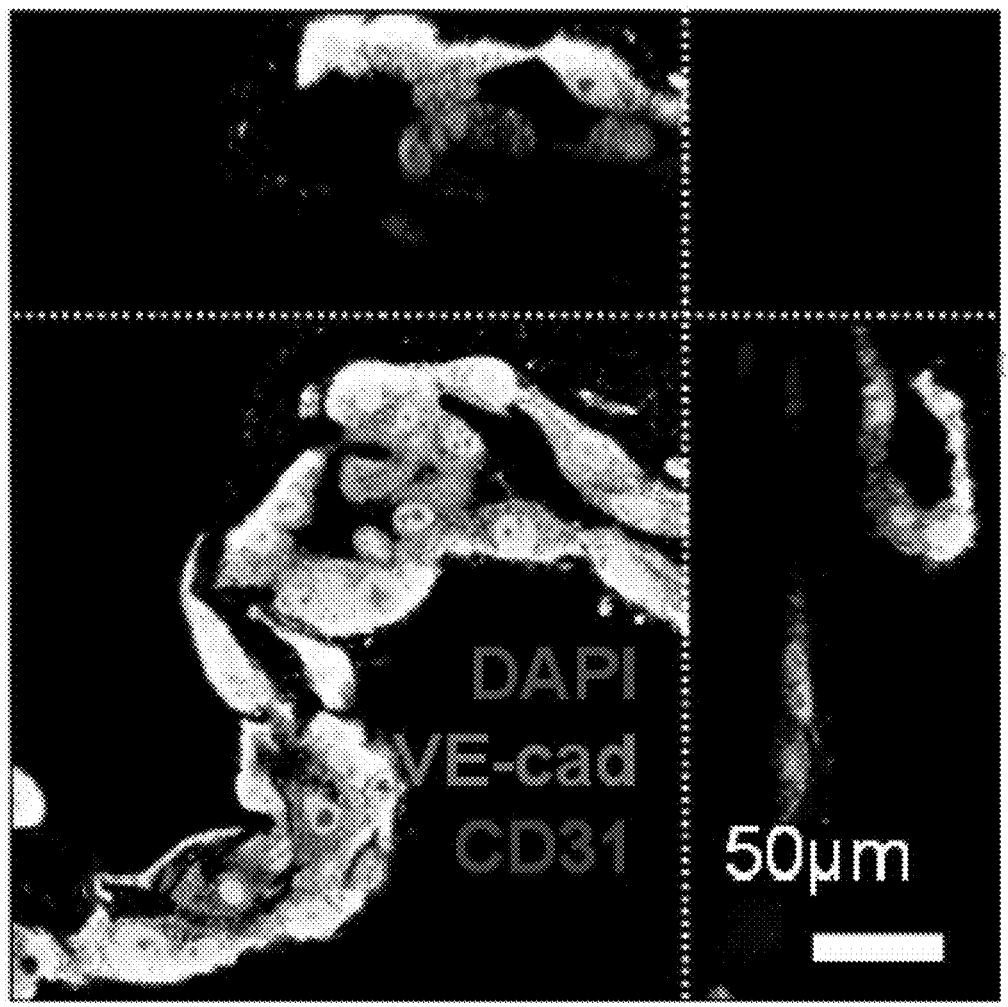
Figure 35A:
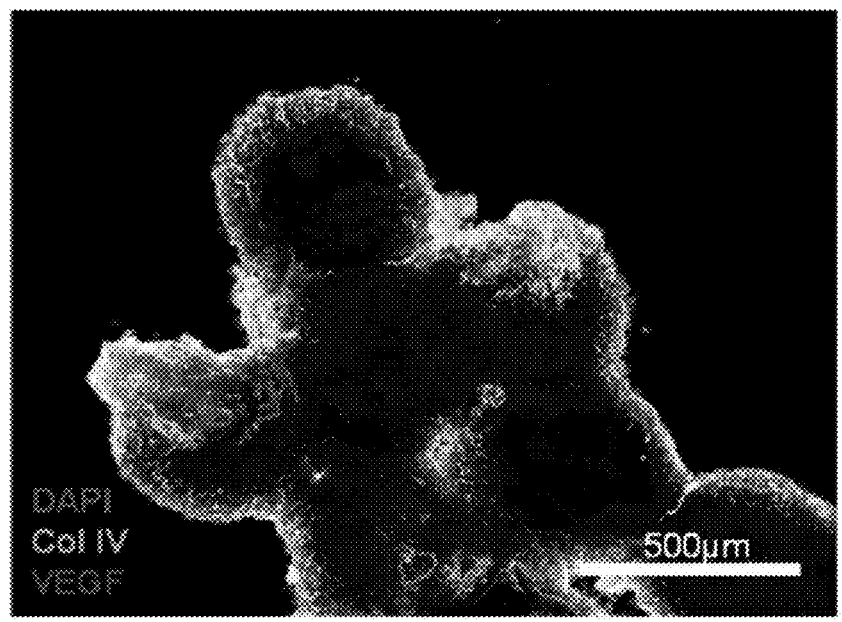
FIGS. 35A and 35B show that the formed tumors can be combined together to a larger tumor. They are confocal microscope photographs showing the formation of blood vessels therein.
Figure 35B:
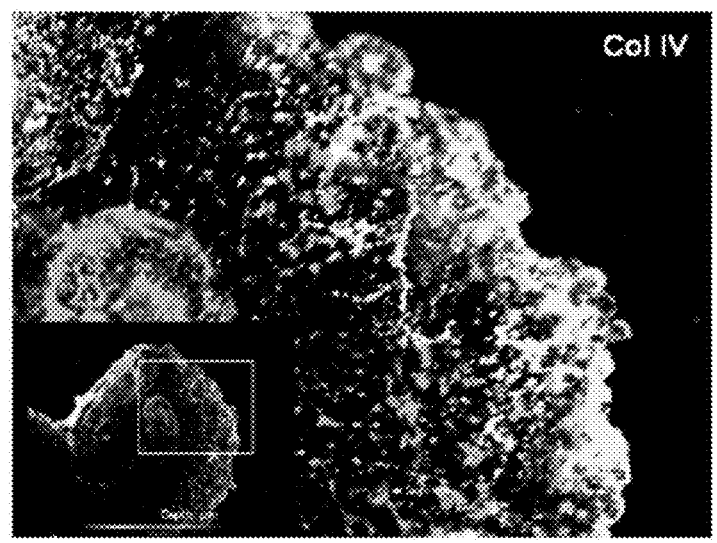
Figure 36A:
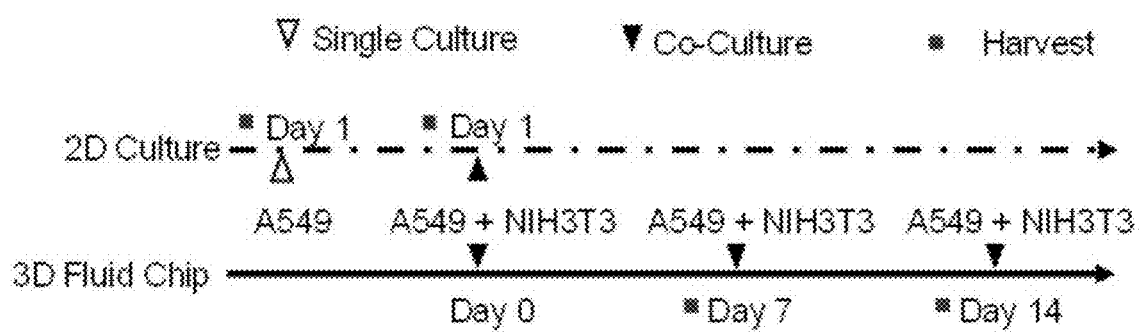
FIGS. 36A to 36F show that intracellular genetic transformation occurs due to the action of fibroblasts in the process of tumor formation.
Figure 36B:
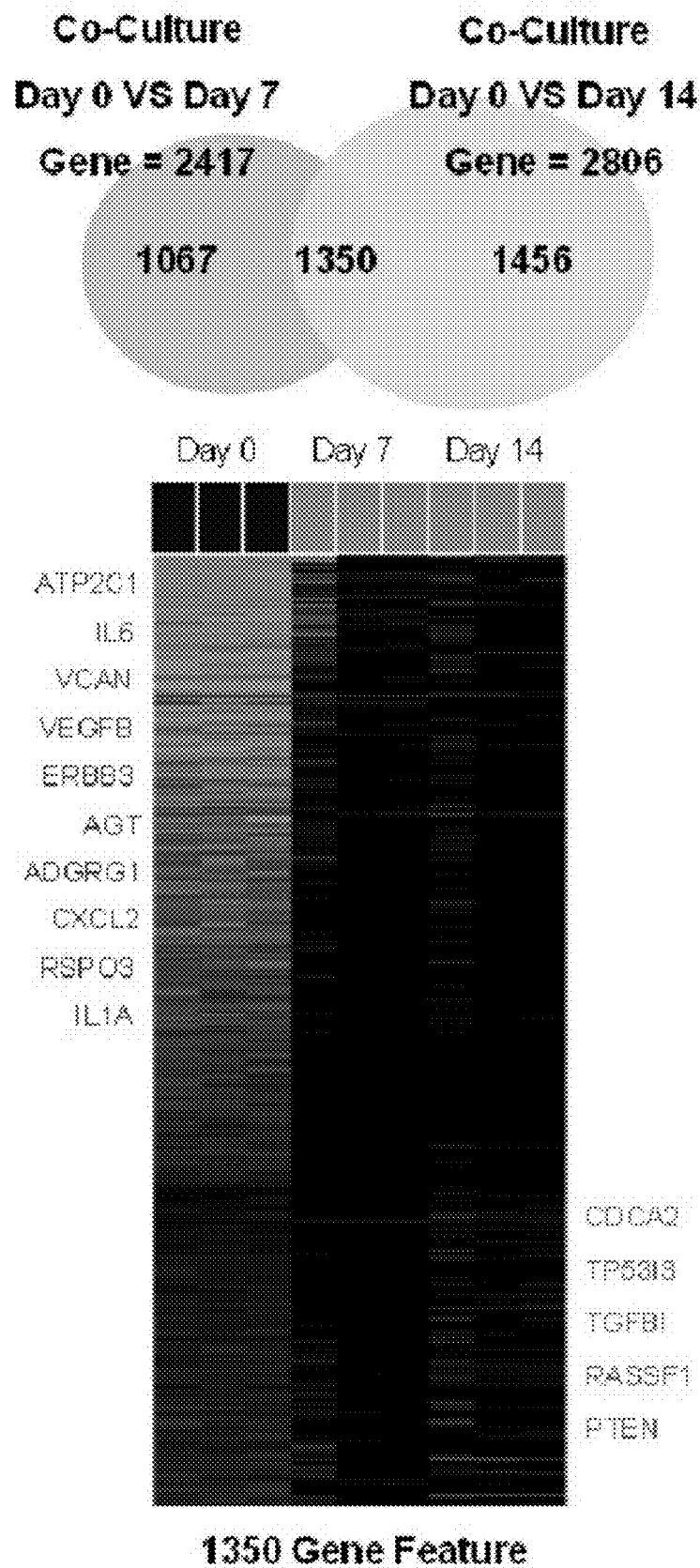
Figure 36C:
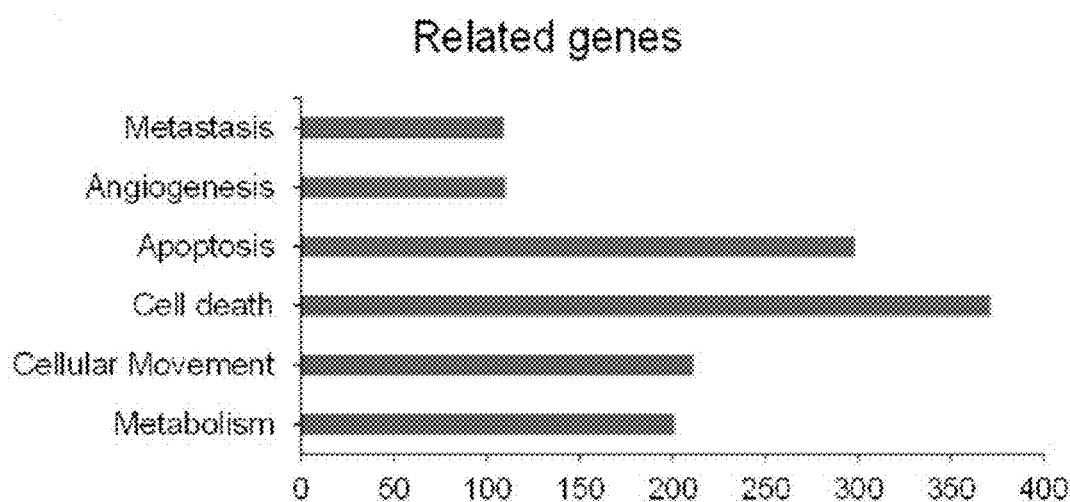
Figure 36D:
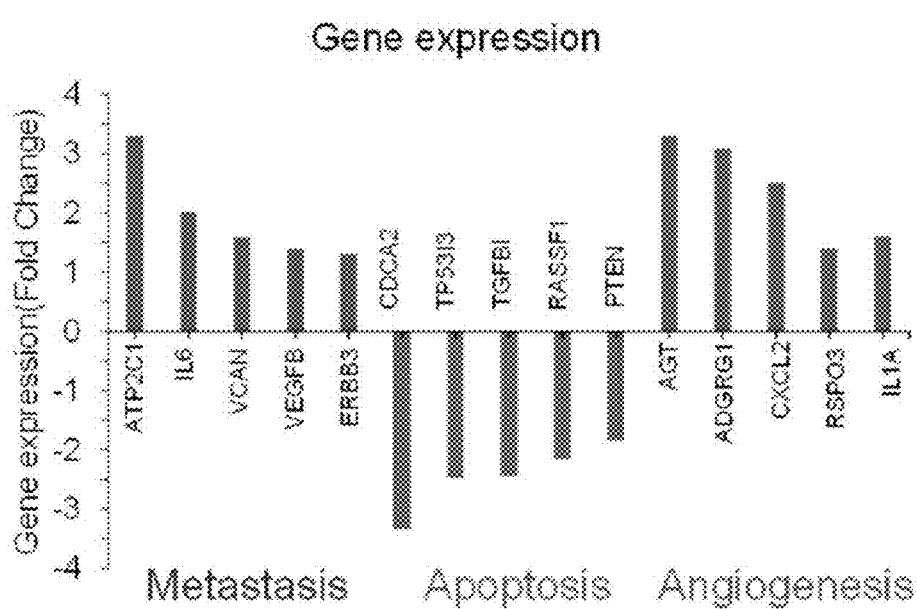
Figure 36E:
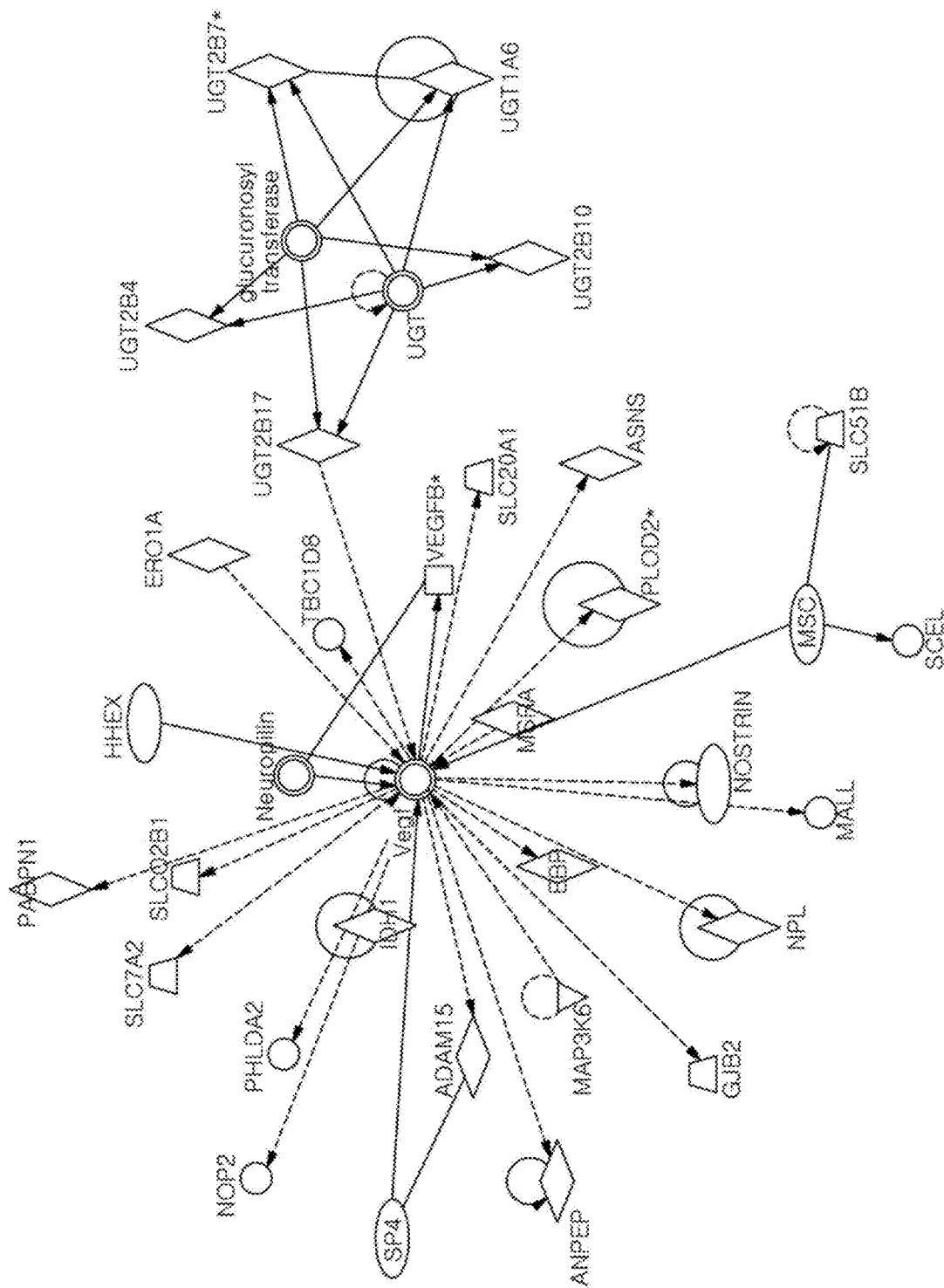
Figure 36F:
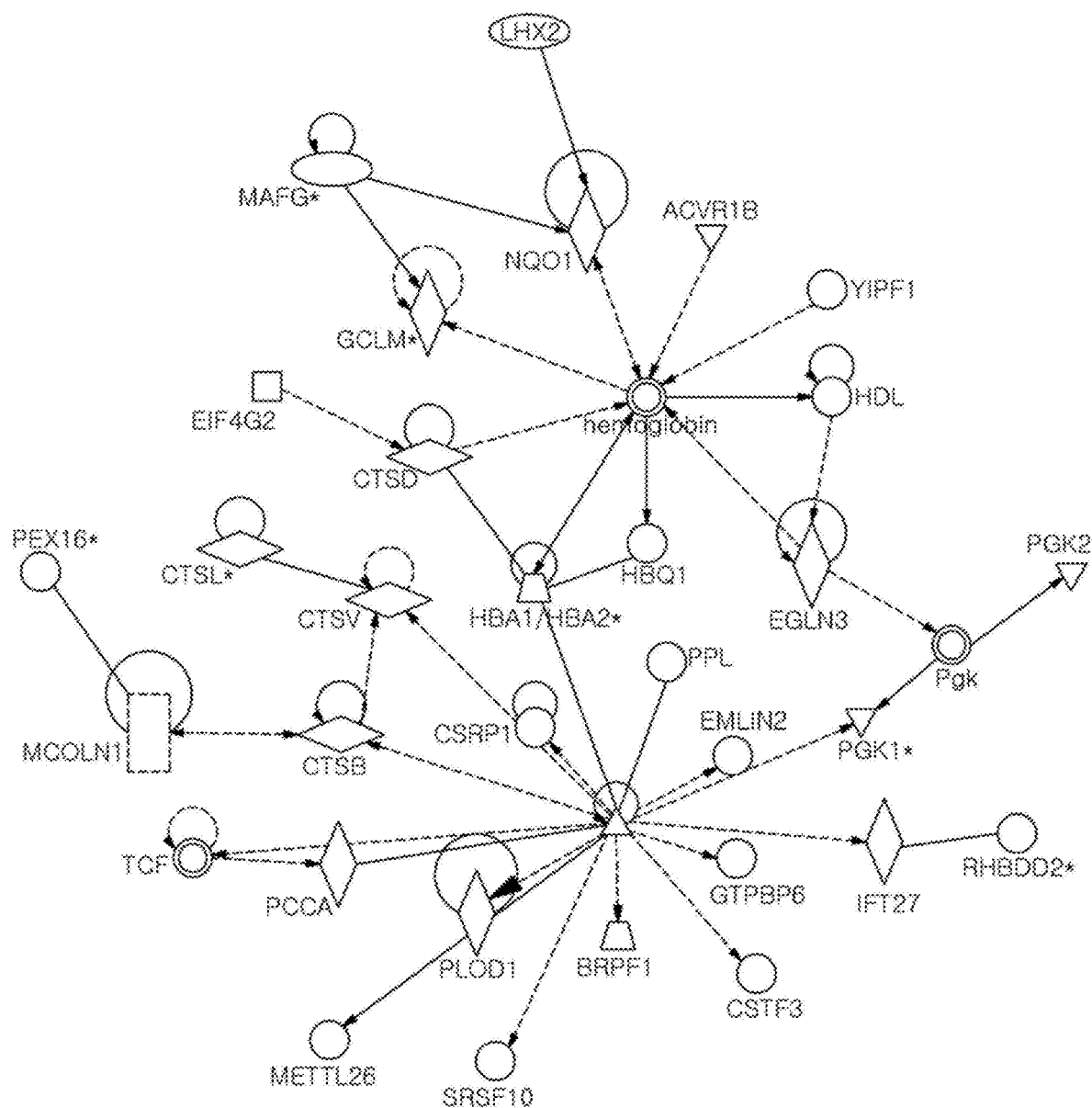

As a result, as shown in FIG. 22, the cancer tissue cells cultured in the microfluidic chip according to an embodiment of the present invention grew to a large tissue to form an organoid.

The microfluidic chip, the three-dimensional tube structure, and the method for culturing cells using the same according to the present invention have been described above as specific embodiments. But these embodiments are given for the purpose of illustration, and the present invention is not limited thereto. It is to be construed that the present invention has the broadest scope according to the basic idea disclosed in this specification. A person skilled in the art may implement a pattern of configurations that are not disclosed by combination and/or replacement of the disclosed embodiments, but this does not fall outside of the scope of the present invention. In addition, a person skilled in the art can easily change or modify the disclosed embodiments based on the present specification. It is evident that such changes or modifications fall within the scope of the present invention.

The invention claimed is:

1. A microfluidic chip comprising:
a plate;
a bridge channel formed in intaglio on one side of the plate;
an inlet formed through the plate to communicate with one end of the bridge channel;
an outlet formed through the plate to communicate with another end of the bridge channel; and
a plurality of wells extending in an outward direction of the plate from the bridge channel to provide a space,
wherein a portion between said one end of the bridge channel and said the other end of the bridge channel has a circular shape, and
wherein the plurality of wells extend radially outward from the circular shaped portion of the bridge channel and are disposed opposite side of a center of the circular shaped portion with respect to the bridge channel, and each of the plurality of wells has a largest width at a radial inner edge thereof so that different types of cells injected into the microfluidic chip are placed in the plurality of wells when a centrifugal force is generated by a rotation of the microfluidic chip.

2. The microfluidic chip of claim 1, wherein a first part connected to the inlet of the bridge channel and a second part connected to the outlet thereof are formed in a symmetrical shape.

3. The microfluidic chip of claim 1, wherein the bridge channel has other portions which are in a form of a plurality of arcs, or circles, which have different sizes from, and are connected to, each other.

4. The microfluidic chip of claim 1, wherein the plurality of wells are spaced apart from each other along the bridge channel.

5. A microfluidic chip comprising:
a plate;
a plurality of bridge channels formed in intaglio on one side of the plate;
a plurality of inlets formed by penetrating through the plate, the inlets respectively communicating with one ends of the plurality of bridge channels;
a plurality of outlets formed by penetrating through the plate, the outlets respectively communicating with other ends of the bridge channels; and
a plurality of wells extending in an outward direction of the plate from each of the plurality of bridge channels to provide a space, wherein a portion between said one end of each of the bridge channels and said the other end of each of the bridge channels has a circular shape, and wherein the plurality of wells extend radially outward from the circular shaped portion of each of the bridge channels and are disposed opposite side of a center of the circular shaped portion with respect to each of the bridge channels, and each of the plurality of wells has a largest width at a radial inner edge thereof so that different types of cells injected into the microfluidic chip are placed in the plurality of wells when a centrifugal force is generated by a rotation of the microfluidic chip.

6. The microfluidic chip of claim 5, wherein the plurality of bridge channels have different sizes from each other, and
the bridge channel having the smallest diameter among the plurality of bridge channels is disposed inside, and the bridge channel having the largest diameter among the plurality of bridge channels is disposed outside.

7. The microfluidic chip of claim 5, wherein at least one of the plurality of bridge channels is not superposed with the others of the plurality of bridge channels.

8. The microfluidic chip of claim 5, wherein at least two of the plurality of bridge channels are connected to each other.

9. A method for culturing cells, comprising:
injecting cells into a microfluidic chip;
rotating the microfluidic chip; and
culturing the cells in the microfluidic chip,
wherein the microfluidic chip is provided with an inlet, an outlet, a bridge channel connecting the inlet and the outlet, and at least one well formed in an outward direction of the bridge channel, and the cells are cultured in the well,
wherein the microfluidic chip includes:
a plate;
a bridge channel formed in intaglio on one side of the plate;
an inlet formed through the plate to communicate with one end of the bridge channel;
an outlet formed through the plate to communicate with another end of the bridge channel; and
a plurality of wells extending in an outward direction of the plate from the bridge channel to provide a space,
wherein a portion between said one end of the bridge channel and said the other end of the bridge channel has a circular shape, and
wherein the plurality of wells extend radially outward from the circular shaped portion of the bridge channel and are disposed opposite side of a center of the circular shaped portion with respect to the bridge channel, and each of the plurality of wells has a largest width at a radial inner edge thereof so that different types of cells injected into the microfluidic chip are placed in the plurality of wells when a centrifugal force is generated by a rotation of the microfluidic chip.

10. The method for culturing cells of claim 9, further comprising:
injecting a biomimetic cell support into the microfluidic chip after rotating the microfluidic chip.

11. The method for culturing cells of claim 10, wherein the biomimetic cell support is at least one selected from a group consisting of collagen, matrigel, fibrin, gelatin, and hyaluronic acid hydrogel.

12. A method for evaluating an activity of a physiologically active substance, comprising:
injecting cells into a microfluidic chip;
rotating the microfluidic chip to supply the cells to a well of the microfluidic chip;
injecting a biomimetic cell support into the microfluidic chip; and
injecting a physiologically active candidate substance into the microfluidic chip,
wherein the microfluidic chip is provided with an inlet, an outlet, a bridge channel connecting the inlet and the outlet, and at least one well formed in an outward direction of the bridge channel,
wherein the microfluidic chip includes:
a plate;
a bridge channel formed in intaglio on one side of the plate;
an inlet formed through the plate to communicate with one end of the bridge channel;
an outlet formed through the plate to communicate with another end of the bridge channel; and
a plurality of wells extending in an outward direction of the plate from the bridge channel to provide a space,
wherein a portion between said one end of the bridge channel and said the other end of the bridge channel has a circular shape, and
wherein the plurality of wells extend radially outward from the circular shaped portion of the bridge channel and are disposed opposite side of a center of the circular shaped portion with respect to the bridge channel, and each of the plurality of wells has a largest width at a radial inner edge thereof so that different types of cells injected into the microfluidic chip are placed in the plurality of wells when a centrifugal force is generated by a rotation of the microfluidic chip.

13. The method of claim 12, wherein the physiologically active candidate substance includes at least one selected from the group consisting of a compound, an anticancer medicine, and a neurotransmitter.

14. A method for preparing an organoid, comprising:
injecting cells into a microfluidic chip;
rotating the microfluidic chip; and
culturing the cells in the microfluidic chip,
wherein the microfluidic chip is provided with an inlet, an outlet, a bridge channel connecting the inlet and the outlet, and at least one well formed in an outward direction of the bridge channel,
wherein the cells include at least one selected from tumor cells, organ cells, stem cells, or a combination thereof, and
wherein the cells are cultured in the well,
wherein the microfluidic chip includes:
a plate;
a bridge channel formed in intaglio on one side of the plate;
an inlet formed through the plate to communicate with one end of the bridge channel;
an outlet formed through the plate to communicate with another end of the bridge channel; and
a plurality of wells extending in an outward direction of the plate from the bridge channel to provide a space,
wherein a portion between said one end of the bridge channel and said the other end of the bridge channel has a circular shape, and
wherein the plurality of wells extend radially outward from the circular shaped portion of the bridge channel and are disposed opposite side of a center of the circular shaped portion with respect to the bridge channel, and each of the plurality of wells has a largest width at a radial inner edge thereof so that different types of cells injected into the microfluidic chip are placed in the plurality of wells when a centrifugal force is generated by a rotation of the microfluidic chip.

* * * * *